(12) United States Patent
Forrester

(10) Patent No.: US 11,052,214 B2
(45) Date of Patent: Jul. 6, 2021

(54) HEATED RESPIRATORY HOSE WIRING

(71) Applicant: Martin E Forrester, Trenton (CA)

(72) Inventor: Martin E Forrester, Trenton (CA)

(73) Assignee: GlobalMed, Inc., Trenton (CA)

( * ) Notice: Subject to any disclaimer, the term of this patent is extended or adjusted under 35 U.S.C. 154(b) by 426 days.

(21) Appl. No.: 15/882,257

(22) Filed: Jan. 29, 2018

(65) Prior Publication Data

US 2018/0214657 A1    Aug. 2, 2018

Related U.S. Application Data

(60) Provisional application No. 62/499,623, filed on Jan. 30, 2017.

(51) Int. Cl.
*B29C 53/58*    (2006.01)
*B29C 53/62*    (2006.01)
(Continued)

(52) U.S. Cl.
CPC .... *A61M 16/1045* (2013.01); *A61M 16/0816* (2013.01); *A61M 16/0833* (2014.02);
(Continued)

(58) Field of Classification Search
CPC .......... A61M 16/1045; A61M 16/0833; A61M 16/0875; A61M 16/1095; A61M 16/0816; A61M 25/0014; A61M 2205/3368; A61M 16/04; A61M 16/0841; A61M 2016/0039; A61M 16/0465; A61M 16/06; A61M 2205/18; A61M 2039/1077; A61M 16/0054; A61M 2016/0018; A61M 2039/1022; A61M 2039/1033; A61M 2207/00; B29C 48/131; B29C 45/14614; B29C 53/827; B29C 53/582; B29C 53/62; B29C 48/09; B29C 53/78; B29C 53/586; B29C 48/0021; B29C 65/02; B29C 65/561; B29C 66/30321; B29C 66/30325; B29C 66/5344; B29C 45/14491;
(Continued)

(56) References Cited

U.S. PATENT DOCUMENTS

| 511,188 A | 12/1893 | Barnard ........................ 439/192 |
| 1,397,682 A | 11/1922 | Geier et al. ..................... 174/46 |

(Continued)

FOREIGN PATENT DOCUMENTS

| DE | 3312434 A1 | 3/1983 | ............... A47L 9/28 |
| DE | 3835248 A1 | 10/1988 | ............. B29C 55/10 |

(Continued)

*Primary Examiner* — Jeffrey M Wollschlager
(74) *Attorney, Agent, or Firm* — David A. Burge; Benjamin D. Burge

(57) ABSTRACT

Helically winding an extruded web to form a wall of a heated hose about a central axis, extruding a bead of plastics material around a heating wire such that the extruded bead comprises the heating wire at a first location within a cross-section of the extruded bead, helically winding the extruded bead onto the wall of the hose to provide a support helix, and exerting tension on the heating wire to draw down the heating wire toward the central axis such that the heating wire migrates radially inward from the first location to a second location within the cross-section of the extruded bead.

20 Claims, 32 Drawing Sheets

(51) Int. Cl.

| | | |
|---|---|---|
| *B29C 53/78* | (2006.01) | |
| *B29C 48/03* | (2019.01) | |
| *B29C 48/09* | (2019.01) | |
| *A61M 16/10* | (2006.01) | |
| *A61M 16/08* | (2006.01) | |
| *B29D 23/00* | (2006.01) | |
| *B29C 45/14* | (2006.01) | |
| *B29C 53/82* | (2006.01) | |
| *B29C 48/00* | (2019.01) | |
| *A61M 25/00* | (2006.01) | |
| *B29C 65/02* | (2006.01) | |
| *B29C 65/56* | (2006.01) | |
| *B29C 65/00* | (2006.01) | |
| *A61M 16/04* | (2006.01) | |
| *A61M 16/00* | (2006.01) | |
| *F16L 53/35* | (2018.01) | |
| *A61M 16/06* | (2006.01) | |
| *A61M 39/10* | (2006.01) | |
| *B29L 23/00* | (2006.01) | |
| *F16L 15/00* | (2006.01) | |
| *F16L 33/24* | (2006.01) | |

(52) U.S. Cl.
CPC .... *A61M 16/0875* (2013.01); *A61M 16/1095* (2014.02); *A61M 25/0014* (2013.01); *B29C 45/14614* (2013.01); *B29C 48/0021* (2019.02); *B29C 48/09* (2019.02); *B29C 48/131* (2019.02); *B29C 53/582* (2013.01); *B29C 53/586* (2013.01); *B29C 53/62* (2013.01); *B29C 53/78* (2013.01); *B29C 53/827* (2013.01); *B29C 65/02* (2013.01); *B29C 65/561* (2013.01); *B29C 66/30321* (2013.01); *B29C 66/30325* (2013.01); *B29C 66/5344* (2013.01); *B29D 23/00* (2013.01); *A61M 16/0054* (2013.01); *A61M 16/04* (2013.01); *A61M 16/0465* (2013.01); *A61M 16/06* (2013.01); *A61M 16/0841* (2014.02); *A61M 2016/0018* (2013.01); *A61M 2016/0039* (2013.01); *A61M 2039/1022* (2013.01); *A61M 2039/1033* (2013.01); *A61M 2039/1077* (2013.01); *A61M 2205/18* (2013.01); *A61M 2205/3368* (2013.01); *A61M 2207/00* (2013.01); *B29C 45/14491* (2013.01); *B29C 2045/14524* (2013.01); *B29L 2023/007* (2013.01); *F16L 15/006* (2013.01); *F16L 33/24* (2013.01); *F16L 53/35* (2018.01)

(58) Field of Classification Search
CPC .......... B29C 2045/14524; B29C 53/56; B29C 53/562; B29C 53/566; B29C 53/58–785; B29D 23/00; B29L 2023/007; F16L 53/35; F16L 15/006; F16L 33/24
See application file for complete search history.

(56) References Cited

U.S. PATENT DOCUMENTS

| | | | | |
|---|---|---|---|---|
| 1,474,528 A | 11/1923 | Hurst | 219/208 | |
| 1,995,302 A | 3/1935 | Goldstein | 128/254 | |
| 2,073,335 A | 3/1937 | Connell | 138/49 | |
| 2,330,651 A | 9/1943 | Welger | 138/56 | |
| 2,396,059 A | 3/1946 | Roberts | 138/56 | |
| 2,398,876 A | 4/1946 | Bailey | 156/194 | |
| 2,430,081 A | 11/1947 | Roberts et al. | 156/144 | |
| 2,486,387 A | 11/1949 | Bringolf | 138/122 | |
| 2,508,774 A | 5/1950 | Roberts | 138/56 | |
| 2,516,864 A | 9/1950 | Gilmore et al. | 154/8 | |
| 2,560,369 A | 7/1951 | Roberts | 154/8 | |
| 2,625,979 A | 1/1953 | Harris et al. | 154/6 | |
| 2,634,311 A | 4/1953 | Darling | 439/311 | |
| 2,641,302 A | 6/1953 | Martin et al. | 154/8 | |
| 2,661,025 A | 12/1953 | Brace | 138/56 | |
| 2,713,381 A | 7/1955 | Seck | 154/8 | |
| 2,731,040 A | 1/1956 | Warburton | 138/49 | |
| 2,731,070 A | 1/1956 | Meissner | B29C 53/785 138/132 | |
| 2,734,616 A | 3/1956 | Duff | 138/122 | |
| 2,739,616 A | 3/1956 | Duff | 138/56 | |
| 2,740,427 A | 4/1956 | Swan | 138/122 | |
| 2,745,074 A | 5/1956 | Darling | 339/16 | |
| 2,793,280 A | 5/1957 | Harvey | 219/39 | |
| 2,819,400 A | 10/1957 | Hewitt | 138/56 | |
| 2,874,723 A | 2/1959 | Kahn | 138/56 | |
| 2,895,001 A | 7/1959 | Noyes et al. | 174/47 | |
| 2,901,024 A | 8/1959 | Marsden, Jr. | 154/8 | |
| 2,913,011 A | 11/1959 | Noyes et al. | 138/56 | |
| 2,914,790 A | 12/1959 | Warburtbn | 15/327 | |
| 2,917,568 A | 12/1959 | Moorman et al. | 174/47 | |
| 2,936,812 A | 5/1960 | Roberts | 154/7 | |
| 2,940,126 A | 6/1960 | Sheridan | 18/55 | |
| 2,954,802 A | 10/1960 | Duff | 138/56 | |
| 2,961,007 A | 11/1960 | Martin | 138/56 | |
| 2,963,750 A | 12/1960 | Pavlic | 18/59 | |
| 2,994,104 A | 8/1961 | Mittag | 18/12 | |
| 2,998,474 A | 8/1961 | Pavlic | 174/47 | |
| 3,034,065 A | 5/1962 | Pauler et al. | 339/16 | |
| 3,034,088 A | 5/1962 | Pauler et al. | 339/16 | |
| 3,047,026 A | 7/1962 | Kahn | 138/122 | |
| 3,058,493 A | 10/1962 | Muller | 138/122 | |
| 3,076,737 A | 2/1963 | Roberts | 156/48 | |
| 3,080,891 A | 3/1963 | Duff | 138/122 | |
| 3,082,394 A | 3/1963 | Hann et al. | 339/16 | |
| 3,112,771 A | 12/1963 | Bringolf | 138/129 | |
| 3,114,172 A | 12/1963 | Coste | 18/19 | |
| 3,122,171 A | 2/1964 | Britton et al. | 138/129 | |
| 3,127,227 A | 3/1964 | Edwards | 339/15 | |
| 3,138,511 A | 6/1964 | Cadwallader | 156/431 | |
| 3,152,202 A | 10/1964 | Murphy, Jr. | 264/167 | |
| 3,155,559 A | 11/1964 | Hall | 156/195 | |
| 3,157,543 A | 11/1964 | Roberts et al. | 156/143 | |
| 3,163,707 A | 12/1964 | Darling | 174/47 | |
| 3,169,552 A | 2/1965 | Fawick | 138/133 | |
| 3,173,822 A | 3/1965 | Rigaut | 156/429 | |
| 3,184,793 A | 5/1965 | Plourde | 18/14 | |
| 3,188,690 A | 6/1965 | Zieg | 18/14 | |
| 3,189,053 A | 6/1965 | Parr | 138/133 | |
| 3,199,541 A | 8/1965 | Richitelli | 138/129 | |
| 3,211,823 A | 10/1965 | Brown et al. | 174/47 | |
| 3,216,458 A | 11/1965 | Sabe | 138/122 | |
| 3,243,328 A | 3/1966 | Britton et al. | 156/195 | |
| 3,248,272 A | 4/1966 | Sawada | 156/143 | |
| 3,255,780 A | 6/1966 | Sguirrell | 138/122 | |
| 3,271,064 A | 9/1966 | Hall | 264/93 | |
| 3,272,678 A | 9/1966 | Swan | 156/429 | |
| 3,273,600 A | 9/1966 | Swan | 138/122 | |
| 3,280,410 A | 10/1966 | Antrobus | 18/14 | |
| 3,286,305 A | 11/1966 | Seckel | 18/19 | |
| 3,297,122 A | 1/1967 | Beck | 138/122 | |
| 3,300,571 A | 1/1967 | Downey et al. | 174/47 | |
| 3,301,734 A | 1/1967 | Britton et al. | 156/425 | |
| 3,314,039 A | 4/1967 | Opper | 339/15 | |
| 3,336,172 A | 8/1967 | Hall et al. | 156/143 | |
| 3,339,168 A | 8/1967 | Belicka et al. | 339/5 | |
| 3,378,673 A | 4/1968 | Hopper | 219/301 | |
| 3,486,532 A | 12/1969 | Sawada | A47L 9/24 138/122 | |
| 3,530,536 A | 9/1970 | Thorman et al. | B29D 23/04 18/14 | |
| 3,536,559 A | 10/1970 | Palley et al. | B65H 81/00 156/429 | |
| 3,564,087 A | 2/1971 | Ruckberg | B29C 17/07 264/89 | |
| 3,567,101 A | 3/1971 | Ranne | B23K 1/20 228/15 | |
| 3,582,968 A | 6/1971 | Buiting et al. | H05B 3/40 219/300 | |

(56) References Cited

U.S. PATENT DOCUMENTS

| | | | | |
|---|---|---|---|---|
| 3,585,361 A | 6/1971 | Rosen et al. | ............ | F27B 11/06 219/421 |
| 3,603,403 A | 9/1971 | Horwimski | ............ | A62C 35/00 169/5 |
| 3,635,255 A | 1/1972 | Kramer | ................... | F16L 11/06 138/122 |
| 3,636,285 A | 1/1972 | Wickham et al. | ............... | 200/51 |
| 3,640,312 A | 2/1972 | Bauman et al. | .......... | A47L 9/24 138/121 |
| 3,674,056 A | 7/1972 | D'Aprile | ................ | F16L 11/16 138/134 |
| 3,677,676 A | 7/1972 | Hegler | ................... | B29D 23/04 425/109 |
| 3,679,531 A | 7/1972 | Wienand et al. | ...... | A44B 21/00 161/48 |
| 3,706,624 A | 12/1972 | Rinker | ................... | B29D 17/00 156/432 |
| 3,739,815 A | 6/1973 | Rejeski | ................... | F16L 11/06 138/122 |
| 3,743,456 A | 7/1973 | Cini | ...................... | B29D 23/04 425/112 |
| 3,751,541 A | 9/1973 | Hagler | ................... | B29C 17/07 264/90 |
| 3,847,001 A | 11/1974 | Thamasett | ............. | B21D 51/01 72/96 |
| 3,856,051 A | 12/1974 | Bain | ...................... | F16L 11/12 138/114 |
| 3,858,615 A | 1/1975 | Weigl | ..................... | F16L 11/06 138/121 |
| 3,861,424 A | 1/1975 | Mizutani | ................ | F16L 11/08 138/119 |
| 3,886,029 A | 5/1975 | Paulsen | ................ | B86L 181/00 156/429 |
| 3,889,716 A | 6/1975 | Linhart | ................... | F16L 11/00 138/129 |
| 3,890,181 A | 6/1975 | Stent et al. | ............... | B31C 3/00 156/143 |
| 3,910,608 A | 10/1975 | Steward | ................ | B29D 23/04 156/143 |
| 3,912,795 A | 10/1975 | Jackson | ............... | A61L 115/00 261/36 |
| 3,916,953 A | 11/1975 | Nagayoshi et al. | .... | F16L 11/08 138/129 |
| 3,919,367 A | 11/1975 | Maroschak | ............... | B29C 5/06 264/40 |
| 3,920,787 A | 11/1975 | McDowell et al. | | |
| 3,928,715 A | 12/1975 | Holden | ............ | 174/47 |
| 3,962,019 A | 6/1976 | Rejeski | ................ | B65H 81/00 156/428 |
| 3,963,856 A | 6/1976 | Carlson et al. | .......... | F16L 11/12 174/47 |
| 3,964,476 A | 6/1976 | Palleni | ................... | A61M 16/00 128/145.6 |
| 3,965,526 A | 6/1976 | Doubleday | ............... | A47L 5/00 15/377 |
| 3,966,525 A | 6/1976 | Steward | ................ | B65H 81/00 156/195 |
| 4,007,737 A | 2/1977 | Paluch | ................... | F10M 17/00 128/188 |
| 4,010,054 A | 3/1977 | Bradt | ..................... | B65H 81/00 156/173 |
| 4,010,748 A | 3/1977 | Dobritz | ................ | A61M 16/00 128/192 |
| 4,012,272 A | 3/1977 | Tiner | ..................... | B65H 81/04 156/429 |
| 4,013,122 A | 3/1977 | Long | ...................... | F28D 7/10 165/154 |
| 4,038,519 A * | 7/1977 | Foucras | ................ | A61M 5/44 392/472 |
| 4,043,856 A | 8/1977 | Steward | ................ | B31C 1/00 156/195 |
| 4,048,993 A | 9/1977 | Dobritz | ................ | A61M 16/00 128/212 |
| 4,063,790 A | 12/1977 | Kleykamp et al. | .............. | 339/16 |
| 4,063,988 A | 12/1977 | Choiniere et al. | ...... | B65H 81/00 156/429 |
| 4,098,298 A | 7/1978 | Vohrer | .................... | F16L 11/08 138/122 |
| 4,104,097 A | 8/1978 | Gregory et al. | .......... | B31C 1/00 156/143 |
| 4,121,624 A | 10/1978 | Chen | ........................ | F16L 11/11 138/122 |
| 4,140,154 A | 2/1979 | Kanao | ..................... | F16L 11/08 138/132 |
| 4,162,370 A | 7/1979 | Dunn et al. | ................ | A47L 9/24 174/47 |
| 4,167,645 A | 9/1979 | Carey | ..................... | F16L 11/12 174/47 |
| 4,172,474 A | 10/1979 | Stahl | ........................ | F16L 11/08 138/132 |
| 4,186,778 A | 2/1980 | Carey | ..................... | F16L 11/12 138/103 |
| 4,194,081 A | 3/1980 | Medford et al. | .......... | F16L 11/11 174/47 |
| 4,196,031 A | 4/1980 | Lalikos et al. | ............ | B32B 1/08 156/143 |
| 4,203,476 A | 5/1980 | Vitellaro | ................. | F16L 11/08 138/122 |
| 4,211,457 A | 7/1980 | Meadows | ........................ | 339/15 |
| 4,213,811 A | 7/1980 | Hall et al. | ................ | B65H 8/00 156/195 |
| 4,224,463 A | 9/1980 | Koerber et al. | ........... | A47L 9/24 174/47 |
| 4,224,965 A | 9/1980 | Suchor | .................... | F16L 11/04 138/154 |
| 4,227,640 A | 10/1980 | Roccaforte | ................ | A47L 9/24 174/47 |
| 4,229,613 A | 10/1980 | Braun | ..................... | F16L 11/12 174/47 |
| 4,232,667 A | 11/1980 | Chalon et al. | ........ | A61M 16/00 120/203.26 |
| 4,233,097 A | 11/1980 | Stahl | ........................ | B31C 13/00 156/143 |
| 4,259,139 A | 3/1981 | Stahl | ........................ | B31C 81/00 156/428 |
| 4,265,235 A | 5/1981 | Fukunaga | .............. | A61M 16/00 128/200.24 |
| 4,294,636 A | 10/1981 | Vitellaro | ................. | B65H 81/00 156/143 |
| 4,304,266 A | 12/1981 | Kutnyak et al. | ......... | F16L 11/08 138/129 |
| 4,327,718 A | 5/1982 | Croneberg | ............ | A61M 16/00 128/205.12 |
| 4,336,798 A | 6/1982 | Beran | ................... | A61M 16/00 128/200.14 |
| 4,337,800 A | 7/1982 | Carlson et al. | .......... | F16L 11/11 138/122 |
| 4,342,612 A | 8/1982 | Lalikos et al. | ............ | F16L 11/11 138/122 |
| 4,343,672 A | 8/1982 | Kanao | ....................... | B31C 1/00 156/428 |
| 4,345,805 A | 8/1982 | Finley et al. | ............ | H01R 3/04 339/1.6 |
| 4,350,547 A | 9/1982 | Kanao | ....................... | D20D 23/12 156/143 |
| 4,354,051 A | 10/1982 | Kutnyak | ................... | A47L 9/24 174/47 |
| 4,375,381 A | 3/1983 | Carlson et al. | ......... | B65H 81/00 156/195 |
| 4,383,555 A | 5/1983 | Finley | ..................... | F16L 11/08 138/129 |
| 4,394,057 A | 7/1983 | Williams et al. | ................ | 339/15 |
| 4,422,702 A | 12/1983 | Nordeen | ................ | H01R 4/64 339/15 |
| 4,423,311 A | 12/1983 | Varney, Sr. | ............. | H05B 3/56 219/306 |

(56) References Cited

U.S. PATENT DOCUMENTS

| | | | | |
|---|---|---|---|---|
| 4,456,034 A | 6/1984 | Bixby | | F16L 55/00 138/122 |
| 4,459,168 A | 7/1984 | Anselm | | B65H 81/00 156/143 |
| 4,462,397 A | 7/1984 | Suzuki | | A61M 16/00 128/200.14 |
| 4,471,813 A | 9/1984 | Cothran | | F16L 11/04 138/122 |
| 4,489,759 A | 12/1984 | Yamamura | | F16L 11/00 138/122 |
| 4,490,200 A | 12/1984 | Dillon | | F16L 11/11 156/143 |
| 4,490,575 A * | 12/1984 | Kutnyak | | A47L 9/24 138/129 |
| 4,501,948 A | 2/1985 | Yampolsky et al. | | B23K 27/00 219/121 |
| 4,521,270 A | 6/1985 | Lupke | | B29D 23/04 156/429 |
| 4,542,280 A | 9/1985 | Simons | | F16L 11/00 138/131 |
| 4,543,951 A | 10/1985 | Phue | | A61M 16/00 128/204.25 |
| 4,547,029 A | 10/1985 | Kutnyak et al. | | 339/16 |
| 4,553,923 A | 11/1985 | Jameson et al. | | H05B 3/58 219/301 |
| 4,575,400 A | 3/1986 | Ueda et al. | | B65H 81/00 156/428 |
| 4,587,145 A | 5/1986 | Kanao | | F16L 11/08 428/36 |
| 4,599,784 A | 7/1986 | Canu, Jr. et al. | | B23P 11/02 29/450 |
| 4,613,389 A | 9/1986 | Tanaka | | F16L 11/08 156/143 |
| 4,616,894 A | 10/1986 | Baker | | H01R 4/64 339/15 |
| 4,618,195 A | 10/1986 | Keane | | H01R 13/73 339/16 |
| 4,621,632 A | 11/1986 | Bartels et al. | | A61M 16/00 128/203.27 |
| 4,629,590 A | 12/1986 | Bagwell | | B01F 3/04 261/78.2 |
| 4,637,384 A | 1/1987 | Schroeder | | A61M 16/00 128/204.18 |
| 4,639,055 A | 1/1987 | Keane | | H01R 3/00 339/16 |
| 4,652,063 A | 3/1987 | Genoa et al. | | H01R 4/64 339/15 |
| 4,667,084 A | 5/1987 | Regge | | H05B 3/58 219/301 |
| 4,686,354 A | 8/1987 | Makin | | A61M 16/15 219/301 |
| 4,693,324 A | 9/1987 | Choiniere et al. | | A47L 9/24 174/47 |
| 4,708,831 A | 11/1987 | Elsworth et al. | | A61M 16/16 261/130 |
| 4,714,508 A | 12/1987 | Chivens et al. | | B23K 27/00 156/195 |
| 4,722,334 A | 2/1988 | Blackmer et al. | | A61M 16/00 128/203.16 |
| 4,773,410 A | 9/1988 | Blackmer et al. | | A61M 16/00 128/203.26 |
| 4,780,261 A | 10/1988 | Vajtay | | B29C 53/00 264/285 |
| 4,787,117 A | 11/1988 | Westergren | | A47L 9/24 15/339 |
| 4,826,423 A | 5/1989 | Kemp et al. | | B29C 47/06 425/505 |
| 4,829,998 A | 5/1989 | Jackson | | A61M 15/00 128/203.12 |
| 4,838,258 A | 6/1989 | Dryden et al. | | A61M 16/00 128/204.18 |
| 4,867,671 A | 9/1989 | Nagayoshi et al. | | B29C 47/08 425/391 |
| 4,917,539 A | 4/1990 | de la Salle | | F16L 1/00 405/154 |
| 4,941,469 A | 7/1990 | Adahan | | A61M 16/16 128/205.18 |
| 4,955,372 A | 9/1990 | Blackmer et al. | | A61M 15/00 128/203.16 |
| 4,967,744 A | 11/1990 | Chua | | A61M 16/01 128/204.18 |
| 4,969,837 A | 11/1990 | Genoa et al. | | H01R 4/64 439/191 |
| 5,031,612 A | 7/1991 | Clementi | | A61M 16/16 128/204.14 |
| 5,101,820 A | 4/1992 | Christopher | | A61M 16/00 128/204.18 |
| 5,121,746 A | 6/1992 | Sikora | | A61M 15/00 128/203.12 |
| 5,218,970 A | 6/1993 | Turnbull et al. | | A61B 5/00 128/748 |
| 5,284,160 A | 2/1994 | Dryden | | A61M 15/00 128/203.12 |
| 5,295,489 A | 3/1994 | Bell et al. | | A61B 5/02 128/715 |
| 5,357,948 A | 10/1994 | Eilentropp | | A61M 15/00 128/204.17 |
| 5,377,670 A | 1/1995 | Smith | | A61M 16/00 128/204.17 |
| 5,387,117 A | 2/1995 | Moyher, Jr. et al. | | H01R 4/60 439/191 |
| 5,392,770 A | 2/1995 | Clawson et al. | | A61M 16/00 128/203.77 |
| 5,404,873 A | 4/1995 | Leagre et al. | | A61M 16/00 128/204.18 |
| 5,416,270 A | 5/1995 | Kanao | | F16L 11/11 174/47 |
| 5,454,061 A | 9/1995 | Carlson | | H04B 3/40 392/478 |
| 5,485,870 A | 1/1996 | Kraik | | F16L 11/10 138/122 |
| 5,526,849 A | 6/1996 | Gray | | F16L 11/08 138/133 |
| 5,537,996 A | 7/1996 | McPhee | | A61M 16/16 128/204.17 |
| 5,555,915 A | 9/1996 | Kanao | | F16L 11/11 138/133 |
| 5,568,944 A | 10/1996 | Kawasaki | | |
| 5,600,752 A | 2/1997 | Lopatinsky | | A61M 16/00 392/488 |
| 5,601,119 A | 2/1997 | Kanao | | F16L 11/118 138/133 |
| 5,636,806 A | 5/1997 | Inagaki et al. | | A61M 25/00 604/282 |
| 5,637,168 A | 6/1997 | Carlson | | B29C 47/02 156/143 |
| 5,640,951 A | 6/1997 | Huddart et al. | | A61M 16/00 128/204.77 |
| 5,701,887 A | 12/1997 | Rustad et al. | | A61M 16/00 128/204.17 |
| 5,715,815 A | 2/1998 | Lorenzen et al. | | A62B 7/10 128/207.14 |
| 5,791,377 A | 8/1998 | LaRochelle | | E03B 7/10 138/33 |
| 5,792,401 A * | 8/1998 | Burnham | | A61M 25/0012 264/103 |
| 5,819,518 A | 10/1998 | Kanao | | D02G 3/36 57/3 |
| 5,848,223 A * | 12/1998 | Carlson | | B29C 48/12 392/478 |
| 5,859,953 A | 1/1999 | Nickless | | F16L 53/00 392/489 |
| 5,894,839 A | 4/1999 | Rosenkoetter et al. | | A61M 16/00 128/200.24 |
| 5,974,227 A | 10/1999 | Schave | | F24H 1/10 392/478 |

(56) References Cited

U.S. PATENT DOCUMENTS

| | | | | |
|---|---|---|---|---|
| 5,983,896 | A | 11/1999 | Fukunaga et al. | A61M 16/00 128/207.14 |
| 5,988,164 | A | 11/1999 | Paluch | A61M 16/00 128/203.26 |
| 6,000,435 | A | 12/1999 | Patel et al. | F16L 9/16 138/122 |
| 6,024,132 | A | 2/2000 | Fujimoto | F16L 11/11 138/122 |
| 6,024,134 | A | 2/2000 | Akedo et al. | F16L 11/04 138/129 |
| 6,029,660 | A | 2/2000 | Calluaud et al. | A61M 15/00 128/203.12 |
| 6,050,260 | A | 4/2000 | Daniell et al. | A61M 16/00 128/204.22 |
| 6,078,730 | A | 6/2000 | Huddart et al. | F24H 1/10 392/480 |
| 6,103,971 | A | 8/2000 | Sato et al. | F16L 11/04 174/47 |
| 6,105,576 | A | 8/2000 | Clawson et al. | A62B 7/10 128/205.12 |
| 6,125,847 | A | 10/2000 | Lin | A61M 16/00 128/204.17 |
| 6,129,082 | A | 10/2000 | Leagre | A62B 7/10 128/205.29 |
| 6,148,818 | A | 11/2000 | Pagan | A61M 16/00 128/207.15 |
| 6,152,186 | A | 11/2000 | Arney et al. | F16L 11/08 138/129 |
| 6,167,883 | B1 | 1/2001 | Beran et al. | A61M 16/00 128/203.17 |
| 6,186,183 | B1 | 2/2001 | Lepoutre | F16L 11/12 138/125 |
| 6,190,480 | B1 | 2/2001 | Carlson | B65H 81/00 156/143 |
| 6,209,539 | B1 | 4/2001 | Loescher et al. | |
| 6,219,490 | B1* | 4/2001 | Gibertoni | A61M 16/0875 392/472 |
| 6,237,643 | B1 | 5/2001 | Lepoutre | F16L 11/04 138/129 |
| 6,240,921 | B1 | 6/2001 | Brydon et al. | A62B 7/00 128/205.23 |
| 6,272,933 | B1 | 8/2001 | Gradon et al. | G01F 1/00 73/861 |
| 6,305,428 | B1 | 10/2001 | Nakamura et al. | F16L 11/10 138/126 |
| 6,347,646 | B2 | 2/2002 | Fukui | F16L 11/00 138/129 |
| 6,349,722 | B1 | 2/2002 | Gradon et al. | A61M 15/00 128/203.17 |
| 6,363,930 | B1 | 4/2002 | Clawson et al. | A62B 18/08 128/201.13 |
| 6,367,510 | B1* | 4/2002 | Carlson | A61M 16/08 138/121 |
| 6,378,520 | B1 | 4/2002 | Davenport | A61M 16/00 128/204.26 |
| 6,394,084 | B1 | 5/2002 | Nitta | A62B 18/08 128/201.13 |
| 6,394,143 | B1 | 5/2002 | Diels et al. | F16L 11/11 138/121 |
| 6,397,841 | B1 | 6/2002 | Kenyon et al. | A62B 18/00 128/202.27 |
| 6,536,428 | B1 | 3/2003 | Smith et al. | A61M 16/00 128/203.17 |
| 6,554,260 | B1 | 4/2003 | Lipscombe et al. | B01F 3/04 261/142 |
| 6,584,972 | B2 | 7/2003 | McPhee | A61M 15/00 128/203.17 |
| 6,659,136 | B2 | 12/2003 | Fukui et al. | F16L 11/00 138/125 |
| 6,662,802 | B2 | 12/2003 | Smith et al. | A61M 15/00 128/203.16 |
| 6,694,974 | B1 | 2/2004 | GeorgeGradon et al. | A61M 15/00 128/203.17 |
| 6,718,973 | B2 | 4/2004 | Koch | A61M 15/00 128/203.16 |
| 6,769,431 | B2 | 8/2004 | Smith et al. | B01D 53/22 128/203.16 |
| 6,827,109 | B2 | 12/2004 | McCaughtry | F16L 11/08 138/134 |
| 6,874,500 | B2 | 4/2005 | Fukunaga et al. | A61M 16/00 128/204.18 |
| 6,918,389 | B2 | 7/2005 | Seakins et al. | H05B 13/00 128/203.27 |
| 6,932,119 | B2 | 8/2005 | Carlson | F16L 11/12 138/121 |
| 6,935,337 | B2 | 8/2005 | Virr et al. | A61M 15/00 128/203.16 |
| 6,939,424 | B1 | 9/2005 | Takala et al. | B65B 81/00 156/191 |
| 6,948,527 | B2 | 9/2005 | Ragner et al. | F16L 11/00 138/119 |
| 6,953,354 | B2 | 10/2005 | Edirisuriya et al. | H01R 4/60 439/191 |
| 7,086,422 | B2 | 8/2006 | Huber et al. | F16L 9/14 138/149 |
| 7,096,864 | B1 | 8/2006 | Mayer et al. | A62B 9/04 128/202.27 |
| 7,120,354 | B2 | 10/2006 | Mackie et al. | F24H 1/10 392/480 |
| 7,137,388 | B2 | 11/2006 | Virr et al. | A61M 11/00 128/203.17 |
| 7,144,473 | B2 | 12/2006 | Baecke | B01D 1/00 159/47.1 |
| 7,156,127 | B2 | 1/2007 | Moulton et al. | F16L 11/112 138/122 |
| 7,178,521 | B2 | 2/2007 | Burrow et al. | A62B 9/04 128/202.27 |
| 7,275,541 | B2 | 10/2007 | Fukunaga et al. | A61M 16/00 128/204.18 |
| 7,291,240 | B2* | 11/2007 | Smith | A61M 11/08 156/195 |
| 7,383,745 | B2 | 6/2008 | Eiteneer et al. | G01N 1/00 73/863.12 |
| 7,418,965 | B2 | 9/2008 | Fukunaga et al. | A61M 16/00 128/204.18 |
| 7,418,980 | B2 | 9/2008 | Lee | F16L 11/08 138/121 |
| 7,431,054 | B2 | 10/2008 | Kramer, Jr. et al. | F16L 9/14 138/133 |
| 7,468,116 | B2 | 12/2008 | Smith et al. | B32B 37/00 156/344 |
| 7,469,719 | B2 | 12/2008 | Gray | F16L 53/00 138/33 |
| 7,478,635 | B2 | 1/2009 | Wixey et al. | A61M 11/00 128/203.17 |
| 7,520,302 | B2 | 4/2009 | Smith | F16L 11/118 138/118 |
| 7,575,005 | B2 | 8/2009 | Mumford et al. | A62B 9/00 128/205.23 |
| 7,588,029 | B2 | 9/2009 | Smith et al. | A61M 15/00 128/203.17 |
| 7,597,119 | B2 | 10/2009 | Boettner | F16L 11/12 138/119 |
| 7,637,288 | B2 | 12/2009 | KresslerHuber et al. | F16L 9/14 138/149 |
| 7,721,766 | B2 | 5/2010 | Sawada | F16L 53/00 138/32 |
| 7,735,523 | B2 | 6/2010 | Smith et al. | F16L 11/118 138/118 |
| 7,856,981 | B2 | 12/2010 | NcAnley et al. | A61M 15/00 128/207.13 |
| 7,958,891 | B2 | 6/2011 | Smith et al. | A62B 18/08 128/203.16 |
| 7,962,018 | B2 | 6/2011 | Hunt et al. | F24F 6/00 392/394 |

(56) References Cited

U.S. PATENT DOCUMENTS

| | | | |
|---|---|---|---|
| 7,965,930 B2 | 6/2011 | Carlson et al. | F24H 1/10 392/478 |
| 7,991,273 B2 | 8/2011 | Sonderegger et al. | F24H 1/10 392/478 |
| 8,006,691 B2 | 8/2011 | Kenyon et al. | A61M 16/00 128/200.24 |
| 8,015,971 B2 | 9/2011 | Kwok | A61M 16/00 128/204.17 |
| 8,020,557 B2 | 9/2011 | Bordewick et al. | A61M 11/00 128/206.18 |
| 8,028,721 B2 | 10/2011 | Koskey, Jr. | F16L 53/00 138/33 |
| 8,063,343 B2 | 11/2011 | McGhin et al. | H05B 1/02 219/497 |
| 8,078,040 B2 | 12/2011 | Forrester | F24H 1/10 392/481 |
| 8,186,345 B2 | 5/2012 | Payton et al. | A61M 11/00 128/204.17 |
| 8,210,173 B2 | 7/2012 | Vandine | A61B 5/08 128/204.21 |
| 8,238,733 B2 | 8/2012 | Sawada et al. | F24H 1/10 392/488 |
| 8,291,939 B2 | 10/2012 | Ferrone | F16L 53/00 138/33 |
| 8,333,195 B2 | 12/2012 | Cortez, Jr. et al. | F23D 11/00 128/203.26 |
| 8,360,059 B2 | 1/2013 | Koulechov et al. | A61M 16/00 128/204.17 |
| 8,453,641 B2 | 6/2013 | Payton et al. | A61M 11/00 128/204.17 |
| 8,453,681 B2 | 6/2013 | Forrester et al. | F16L 11/118 138/122 |
| 8,529,719 B2 | 9/2013 | Pingleton et al. | B32B 37/00 156/173 |
| 8,544,504 B2 | 10/2013 | Castro | F16L 11/00 138/121 |
| 8,550,075 B2 | 10/2013 | Virr | A61M 16/16 128/203.27 |
| 8,563,863 B2 * | 10/2013 | Carlson | F16L 11/081 156/187 |
| 8,563,864 B2 | 10/2013 | Carlson | H01B 7/18 174/108 |
| 8,631,789 B2 | 1/2014 | Virr et al. | A61M 15/00 128/204.18 |
| 8,691,035 B2 | 4/2014 | Pingleton et al. | A61M 25/01 156/172 |
| 8,709,187 B2 | 4/2014 | Smith et al. | B31C 1/00 156/184 |
| 8,715,441 B2 | 5/2014 | Brustad et al. | B29C 65/02 156/143 |
| 8,726,901 B2 | 5/2014 | Jassell et al. | A61M 16/08 128/204.17 |
| 8,739,780 B2 | 6/2014 | Tang et al. | A61M 11/00 128/203.14 |
| 8,776,836 B2 | 7/2014 | Ragner et al. | F16L 11/00 138/119 |
| 8,833,367 B2 | 9/2014 | Kwok | A61M 16/10 128/206.22 |
| 8,863,782 B2 | 10/2014 | Ferrone | A01L 7/027 138/33 |
| 8,890,039 B2 | 11/2014 | Etschead et al. | G05D 23/1912 219/492 |
| 8,893,715 B2 | 11/2014 | Payton et al. | F23D 14/00 128/204.18 |
| 8,905,082 B2 | 12/2014 | Gray | F16L 11/00 138/109 |
| 8,965,187 B2 | 2/2015 | Borgmeier et al. | F16L 11/12 392/480 |
| 8,985,105 B2 | 3/2015 | Burton et al. | F16K 31/02 128/203.12 |
| 9,022,036 B2 | 5/2015 | Graham et al. | A61M 16/00 128/207.14 |
| 9,077,134 B2 | 7/2015 | Ferrone | H01R 43/00 29/507 |
| 9,186,477 B2 | 11/2015 | Hunt et al. | F24F 6/00 128/203 |
| 9,206,934 B2 | 12/2015 | Reusche et al. | F16L 53/008 138/33 |
| 9,272,114 B2 | 3/2016 | Herron | A61M 16/0875 138/33 |
| 9,295,801 B2 | 3/2016 | Graham et al. | A61M 16/0875 128/203.26 |
| 9,308,698 B2 | 4/2016 | Forrester et al. | B29D 23/18 156/143 |
| 9,322,501 B2 | 4/2016 | Carlson | F16L 53/004 392/478 |
| 9,358,316 B2 | 6/2016 | Leyva | A61L 2/202 422/28 |
| 9,365,004 B2 | 6/2016 | Forrester | F16L 11/115 156/143 |
| D761,422 S | 7/2016 | Row et al. | D24/129 |
| D762,843 S | 8/2016 | Formica et al. | D24/110 |
| 9,464,747 B2 | 10/2016 | Eckardt et al. | F16L 53/008 |
| 9,505,164 B2 | 11/2016 | Garrett et al. | B29C 53/582 156/244.11 |
| 9,506,595 B2 | 11/2016 | Eckardt et al. | F16L 53/008 |
| 9,533,117 B2 | 1/2017 | Gray | A61M 16/0883 138/33 |
| 9,556,978 B2 | 1/2017 | Garrett et al. | F16L 11/24 138/122 |
| 9,566,408 B2 | 2/2017 | Henry | A61M 16/00 128/205.25 |
| 9,664,086 B2 | 3/2017 | Birman et al. | F24H 1/10 |
| 9,624,806 B2 | 4/2017 | Mann | F01N 3/208 |
| 9,625,066 B2 | 4/2017 | Carlson et al. | F16L 11/24 138/122 |
| 9,638,359 B2 | 5/2017 | Rothfuss | F16L 11/16 138/134 |
| 9,642,979 B2 | 5/2017 | Korneff et al. | A61M 16/1095 |
| 9,656,038 B2 | 5/2017 | Rummery et al. | A61M 16/0675 138/121 |
| 9,671,053 B2 | 6/2017 | Eckardt et al. | F16L 53/00 392/485 |
| 9,702,492 B2 | 7/2017 | Borgmeier et al. | F16L 39/00 |
| 9,707,370 B2 | 7/2017 | Smith et al. | A61M 16/16 |
| 9,717,874 B2 | 8/2017 | Smith et al. | A61M 16/0875 428/139 |
| RE46,543 E | 9/2017 | TrevorWilson et al. | A61M 16/00 |
| D798,428 S | 9/2017 | Cork et al. | B01D 46/02 D23/360 |
| 9,750,916 B2 | 9/2017 | Magee | A61M 16/10 261/142 |
| 9,765,909 B2 | 9/2017 | Ashcroft | F16L 11/12 138/118 |
| RE46,571 E | 10/2017 | Virr et al. | A61M 16/16 |
| 9,784,387 B2 | 10/2017 | Kaye et al. | F16L 138/109 |
| 9,802,015 B2 | 10/2017 | Virr et al. | A61M 16/00 128/204.23 |
| 9,821,135 B2 | 11/2017 | Tang et al. | A61M 16/16 128/202.22 |
| 9,964,238 B2 | 5/2018 | Forrester et al. | F16L 11/112 156/143 |
| 9,982,810 B2 | 5/2018 | Carlson et al. | F16L 11/115 156/244.13 |
| 9,987,460 B2 | 6/2018 | Brustad et al. | A61M 25/00 |
| 9,989,174 B2 | 6/2018 | Garrett et al. | F16L 11/24 138/122 |
| 10,010,693 B2 | 7/2018 | Sims | F24H 1/10 |
| 10,252,017 B2 | 4/2019 | Smith et al. | A61M 16/08 |
| 10,279,141 B2 | 5/2019 | Virr et al. | A61M 16/16 |
| 10,293,121 B2 | 5/2019 | Blackhurst et al. | A61B 1/100 |
| 10,307,560 B2 | 6/2019 | Martin et al. | A61M 16/16 |
| 2002/0148522 A1 | 10/2002 | Hupertz et al. | F16L 11/16 138/135 |
| 2003/0059213 A1 | 3/2003 | Mackie et al. | |

(56) References Cited

U.S. PATENT DOCUMENTS

| | | | |
|---|---|---|---|
| 2003/0098084 A1 | 5/2003 | Ragner et al. | F16L 11/00 138/129 |
| 2004/0007278 A1 | 1/2004 | Williams | A47L 9/24 138/121 |
| 2004/0079371 A1 | 4/2004 | Gray | A61M 16/00 128/204.17 |
| 2004/0081784 A1 | 4/2004 | Smith et al. | B32B 1/08 428/36.9 |
| 2004/0100093 A1 | 5/2004 | Leigh-Monstevens | |
| 2006/0011249 A1 | 1/2006 | Arima et al. | F16L 11/00 138/100 |
| 2006/0051547 A1 | 3/2006 | Lim | B29C 53/582 428/204.17 |
| 2006/0070679 A1 | 4/2006 | Ragner | F16L 11/00 138/119 |
| 2006/0165829 A1 | 7/2006 | Smith et al. | B29C 47/00 425/113 |
| 2006/0252292 A1 | 11/2006 | Sonderegger et al. | H01R 4/60 439/191 |
| 2007/0283958 A1 | 12/2007 | Naghavi | A61M 16/00 128/204.18 |
| 2008/0000474 A1 | 1/2008 | Jochle et al. | A61M 16/00 128/204.18 |
| 2008/0035229 A1 | 2/2008 | Kramer et al. | F16L 11/00 138/132 |
| 2008/0202512 A1 | 8/2008 | Kressierer | A61M 16/00 |
| 2009/0050227 A1 | 2/2009 | Smith | F16L 11/00 138/122 |
| 2009/0078259 A1 | 3/2009 | Kooij et al. | A62B 18/02 128/205.25 |
| 2009/0078440 A1 | 3/2009 | Carlson et al. | F16L 11/12 171/17 |
| 2009/0277525 A1 | 11/2009 | Jourdan et al. | A47L 9/248 138/122 |
| 2010/0108170 A1 | 5/2010 | Chudkosky et al. | F16L 11/11 138/122 |
| 2010/0139661 A1 | 6/2010 | Landis | A62B 18/02 128/205.25 |
| 2010/0148500 A1 | 6/2010 | Uehara et al. | |
| 2010/0215351 A1* | 8/2010 | Forrester | F16L 11/12 392/481 |
| 2010/0224276 A1 | 9/2010 | Forrester | A47L 9/248 138/122 |
| 2011/0005661 A1 | 1/2011 | Brustad et al. | B29D 23/20 156/143 |
| 2011/0006513 A1 | 1/2011 | Lechner et al. | F16L 41/00 285/122.1 |
| 2011/0108031 A1 | 5/2011 | Korneff et al. | A61M 16/16 128/203.27 |
| 2011/0151008 A1 | 6/2011 | Jackson et al. | F16L 53/00 |
| 2012/0247619 A1 | 10/2012 | Obayashi et al. | 128/204.18 |
| 2012/0291783 A1 | 11/2012 | Peiris et al. | A61M 16/00 128/204.21 |
| 2013/0068334 A1 | 3/2013 | Diels | F16L 11/24 138/129 |
| 2013/0073013 A1 | 3/2013 | Pujol | A61F 7/00 607/104 |
| 2013/0098260 A1 | 4/2013 | Hurmez et al. | A61M 16/16 128/203.12 |
| 2013/0098360 A1 | 4/2013 | Hurmez et al. | |
| 2013/0152931 A1 | 6/2013 | Sims et al. | A61M 16/08 128/204.17 |
| 2013/0233318 A1 | 9/2013 | Graham et al. | A61M 16/08 128/205.27 |
| 2013/0306075 A1 | 11/2013 | Payton et al. | A61M 16/00 128/205.23 |
| 2014/0053939 A1 | 2/2014 | Kaye et al. | |
| 2014/0076605 A1 | 3/2014 | Diels et al. | F16L 11/16 174/98 |
| 2014/0102452 A1 | 4/2014 | Forrester | A61M 16/08 128/204.18 |
| 2014/0130931 A1 | 5/2014 | Forrester | F16L 11/112 |
| 2014/0158125 A1 | 6/2014 | O'Donnell et al. | A61L 2/24 128/203.14 |
| 2014/0158130 A1 | 6/2014 | Coleman et al. | |
| 2014/0202462 A1 | 7/2014 | Stoks et al. | A61M 25/00 128/204.18 |
| 2014/0236083 A1 | 8/2014 | Sims | A61M 16/10 604/114 |
| 2014/0238397 A1 | 8/2014 | Buechi et al. | A61M 16/1095 128/203.27 |
| 2014/0311487 A1 | 10/2014 | Buechi et al. | A61M 16/08 128/203.14 |
| 2014/0326395 A1 | 11/2014 | Forrester | B29D 23/18 156/195 |
| 2014/0332108 A1 | 11/2014 | Forrester et al. | F16L 11/112 138/122 |
| 2014/0366979 A1 | 12/2014 | Mollen | F16L 11/08 138/138 |
| 2014/0373843 A1 | 12/2014 | Gray | A61M 16/08 128/204.17 |
| 2015/0020801 A1 | 1/2015 | Frame et al. | A61M 16/00 128/202.22 |
| 2015/0020803 A1 | 1/2015 | Dunlop | |
| 2015/0059908 A1 | 3/2015 | Mollen | F16L 11/08 138/132 |
| 2015/0108670 A1 | 4/2015 | Magee | A61M 16/1045 |
| 2015/0128944 A1 | 5/2015 | Buechi | A61M 16/10 |
| 2015/0165157 A1 | 6/2015 | Payton et al. | A61M 16/16 |
| 2015/0202402 A1 | 7/2015 | Kat | A61M 16/16 |
| 2015/0217079 A1 | 8/2015 | Meauley et al. | A61M 16/10 |
| 2015/0276097 A1* | 10/2015 | Carlson | F16L 11/24 138/129 |
| 2015/0276098 A1 | 10/2015 | Garrett et al. | F16L 11/24 |
| 2015/0283350 A1 | 10/2015 | Miller et al. | A61M 16/08 |
| 2016/0101257 A1 | 4/2016 | Lee et al. | A61M 16/1095 |
| 2016/0175551 A9 | 6/2016 | Forrester | A61M 16/08 |
| 2016/0186898 A9 | 6/2016 | Garrett et al. | F16L 11/24 |
| 2016/0193437 A1 | 7/2016 | Bao et al. | A61M 16/00 |
| 2016/0347012 A9 | 12/2016 | Garrett et al. | F16L 11/00 |
| 2017/0000968 A1 | 1/2017 | Harrington et al. | A61M 16/16 |
| 2017/0082223 A1 | 3/2017 | Garrett et al. | F16L 11/16 |
| 2017/0099877 A1 | 4/2017 | Worm et al. | |
| 2017/0138514 A1 | 5/2017 | Garrett et al. | F16L 11/24 |
| 2017/0182280 A1 | 6/2017 | Leonard | A61M 16/145 |
| 2017/0197055 A1 | 7/2017 | Moody et al. | A61M 16/08 |
| 2017/0333663 A1 | 11/2017 | Huber et al. | A61M 16/20 |
| 2018/0214657 A1 | 8/2018 | Forrester | A61M 16/1045 |
| 2018/0214658 A1 | 8/2018 | Forrester | A61M 16/1045 |
| 2018/0214659 A1 | 8/2018 | Forrester | A61M 16/1095 |

FOREIGN PATENT DOCUMENTS

| | | | |
|---|---|---|---|
| DE | 4039215 A1 | 12/1990 | B29D 23/22 |
| DE | 29507806 U2 | 5/1995 | F16L 11/127 |
| DE | 69527528 T2 | 5/1995 | F24H 1/10 |
| DE | 19737676 C1 | 8/1997 | F16L 11/12 |
| DE | 19752008 A1 | 11/1997 | A47L 9/24 |
| DE | 19904864 A1 | 2/1999 | E21B 7/26 |
| DE | 19949283 A1 | 10/1999 | A61M 16/08 |
| DE | 202005013 786 | 12/2005 | F16L 11/24 |
| DE | 102006023459 A1 | 5/2006 | F16L 37/14 |
| DE | 102008022663.7 | 5/2008 | F16L 11/12 |
| DE | 102009009790 B3 | 2/2009 | F16L 11/11 |
| DE | 102013109362 A1 | 8/2013 | F16L 11/04 |
| DE | 102013106164 A1 | 12/2014 | F16L 11/127 |
| EP | 0097901 | 6/1983 | F16L 11/11 |
| EP | 0201985 | 2/1986 | A61M 16/08 |
| EP | 0742399 | 5/1996 | F16L 11/127 |
| EP | 0917851 | 11/1997 | A47L 9/24 |
| EP | 0950424 B1 | 3/1999 | A61M 25/00 |
| EP | 1181945 A1 | 9/2002 | A61M 16/10 |
| FR | 2303663 | 3/1975 | |
| FR | 2691519 A1 | 11/1993 | |
| WO | WO 2004/011072 | 5/1995 | A61M 16/00 |
| WO | WO 95/33163 | 12/1995 | F24H 1/10 |
| WO | 98/04311 A1 | 2/1998 | |
| WO | 02/38426 A1 | 5/2002 | |
| WO | WO 2004/024429 | 3/2004 | B29C 53/02 |
| WO | WO 2006/094576 | 1/2006 | A61M 16/10 |

(56) References Cited

FOREIGN PATENT DOCUMENTS

| WO | 2007/101298 A1 | 9/2007 |
| WO | 2009/103869 A2 | 8/2009 |
| WO | WO 2011/151008 | 12/2011 |
| WO | 2014/044499 A1 | 3/2014 |
| WO | 2016/007019 A1 | 1/2016 |

* cited by examiner

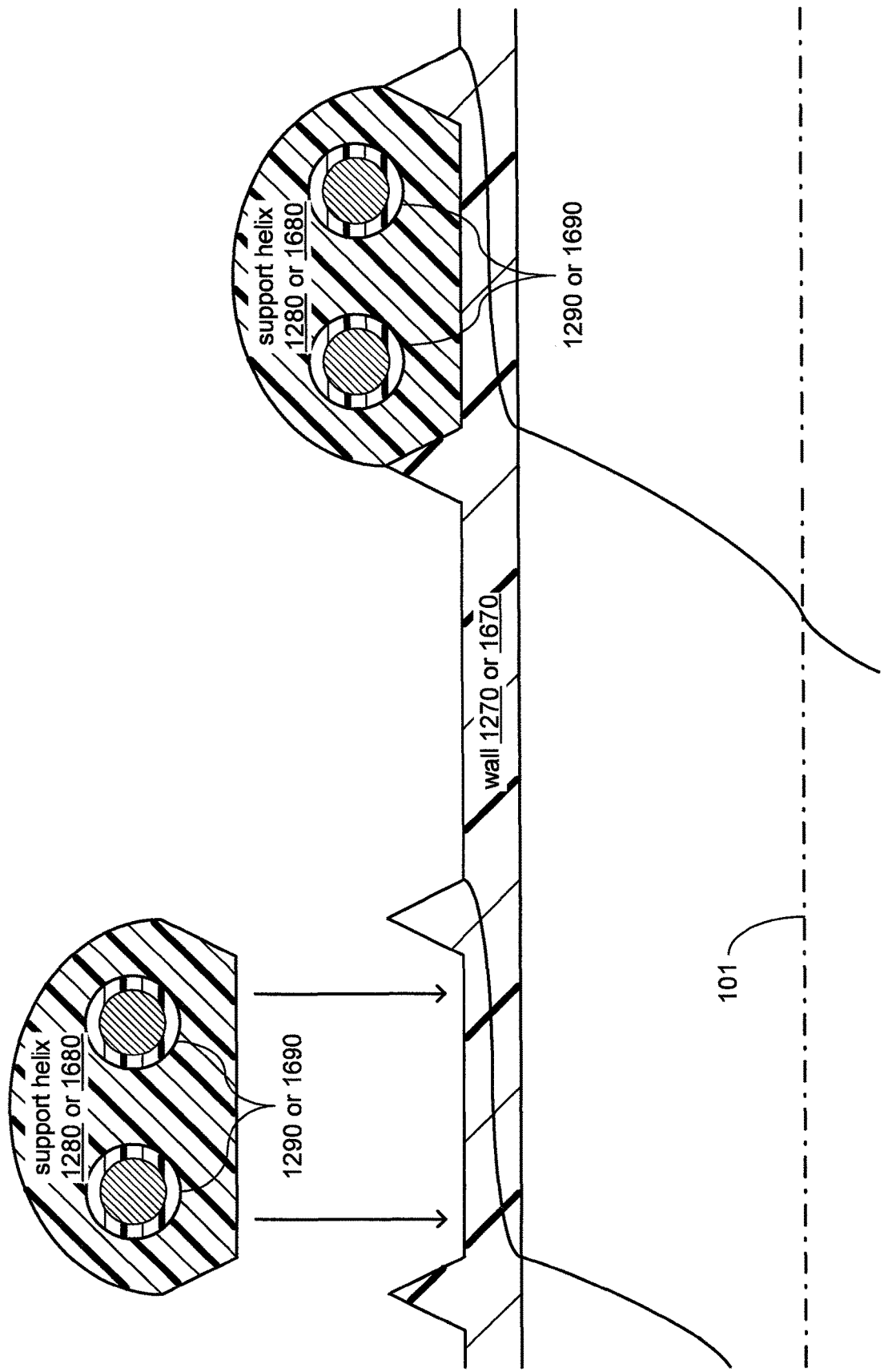

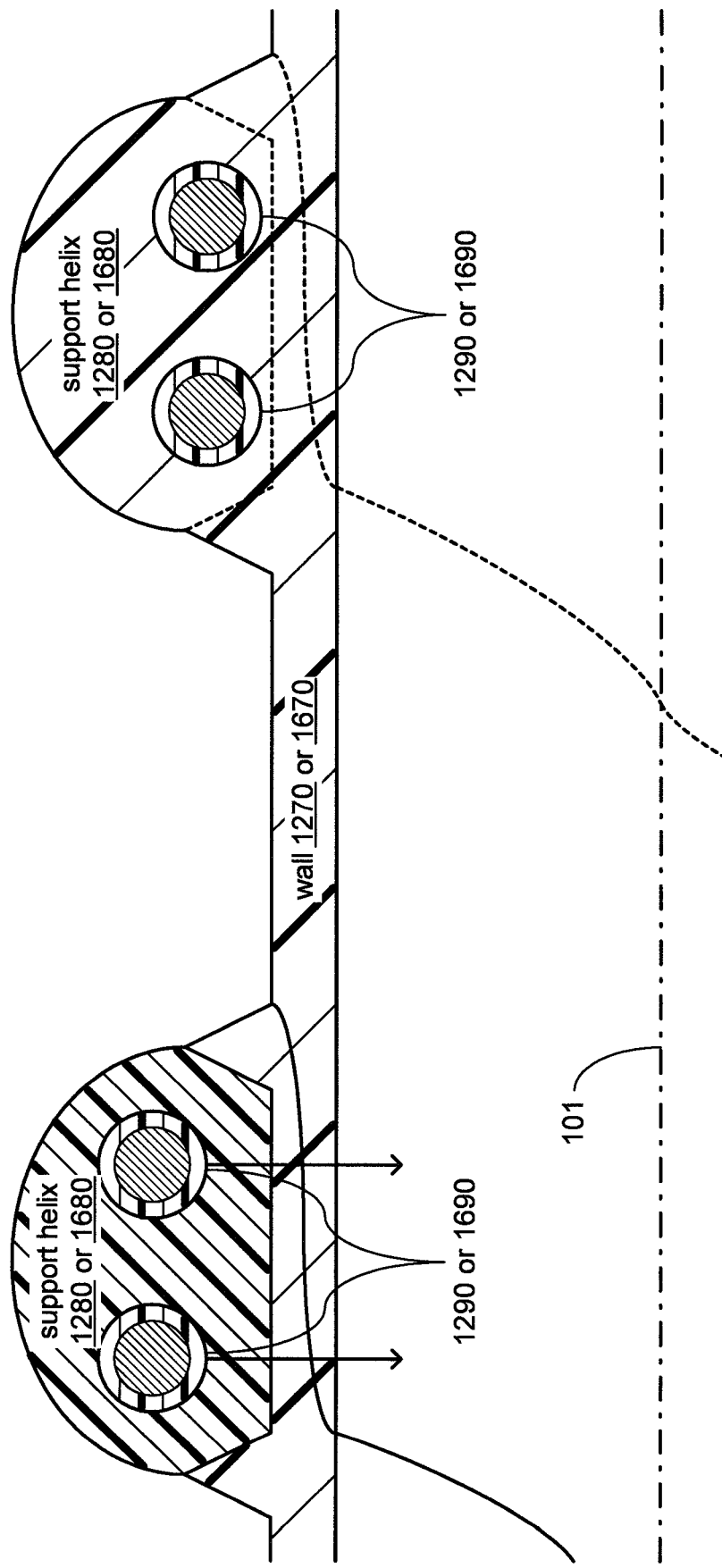

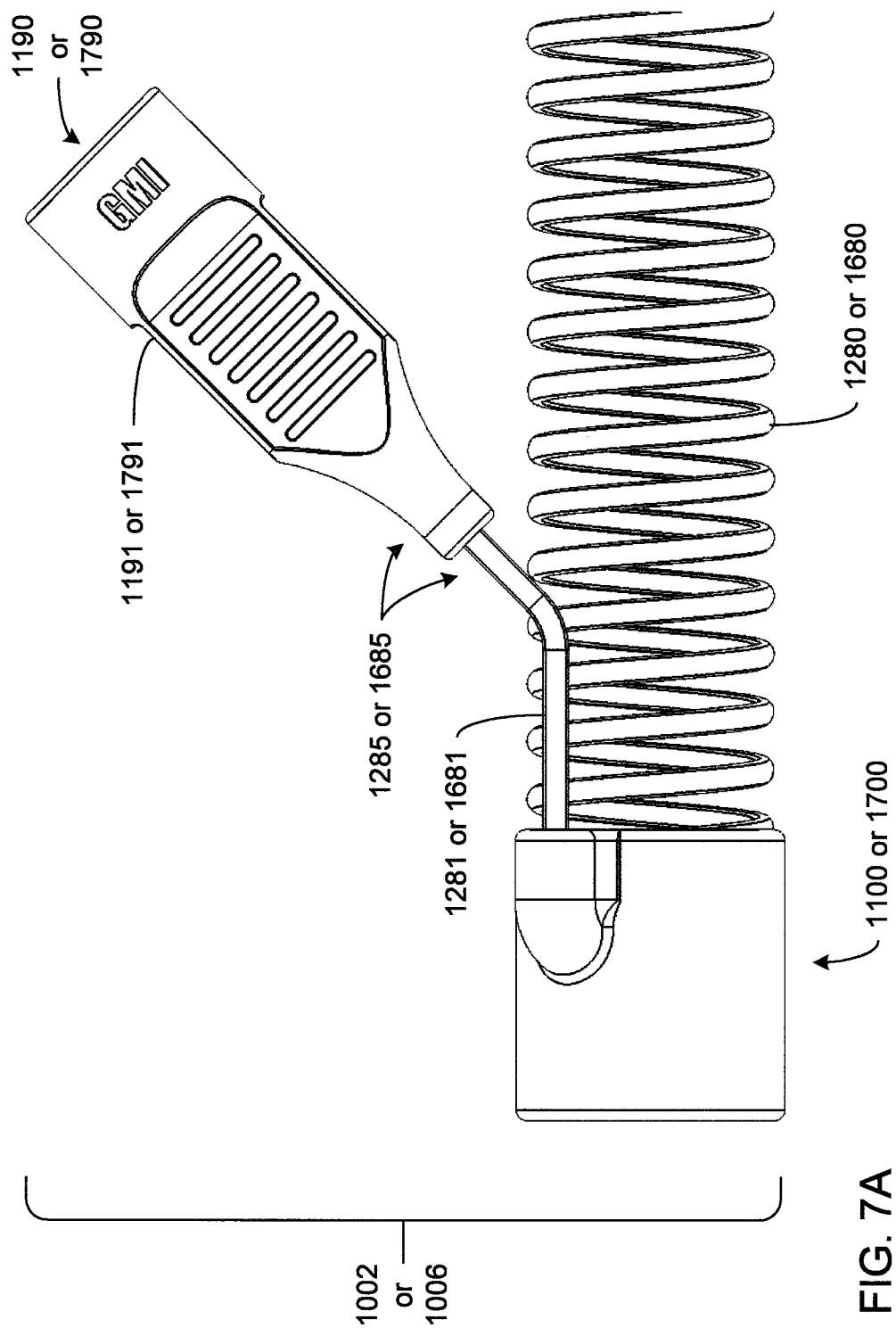

HEATED RESPIRATORY HOSE WIRING

REFERENCE TO PROVISIONAL APPLICATION

This Utility Patent Application claims the benefit of the filing date of Provisional Application Ser. No. 62/499,623 filed Jan. 30, 2017 by Martin E. Forrester, and entitled HEATED RESPIRATORY HOSE ASSEMBLY, the disclosure of which is incorporated herein by reference in its entirety.

BACKGROUND

The present invention relates to the field of hoses to convey respiratory gases to and from patients as part of treating various medical conditions, such as traumatic lung injury, sleep apnea, asthma, chronic obstructive pulmonary disease (COPD), hypoxemia and hypotension. Such hoses may be incorporated into assemblies of used to convey respiratory gases between a medical device, such as a ventilator or continuous positive airway pressure (CPAP) device, and a face mask, an endotracheal tube or tracheostomy stoma of a patient. Such equipment may be used in a hospital or other medical facility, or may be used at a patient's home, such as at a patient's bedside while sleeping.

It is usually deemed desirable for such gases conveyed to a patient include some degree of water vapor to avoid drying tissues of a patient's respiratory system. Also, the respiratory gases that a patient breathes out also typically include some amount of water vapor. An issue arising from the water vapor in the respiratory gases conveyed both to and from a patient is that of condensation within the hoses. If the temperature of the gases in one of the hoses falls below the dew point of the gases within that hose, then water vapor condenses within that hose, and possibly leads to pooling of liquid water within the lowest portion of the hose. As a result, the flow of gases through that hose may be constricted or even cut off entirely in a manner very much akin to the pooling of water within a sink drain trap. Alternatively or additionally, depending on where such pooling occurs within a hose, it is possible for a patient to be caused to breathe in pooled water from within a hose and/or for pooled water within a hose to be sent into the medical device. Such developments may be acutely and immediately harmful to the patient such that the patient may be caused to actually drown from inhalation of liquid water into the lungs, and/or the medical device may be damaged by the intake of liquid water, instead of gases breathed out by the patient.

Among prior art efforts to address such issues is the addition of water traps to each such hose. A water trap serves, in essence, as a designated location along the length of a hose where liquid water can be allowed to pool relatively harmlessly out of the path of flow of gases through the hose to at least minimize any possible obstruction to the passage of gases through the hose. Unfortunately, the use of water traps suffers various drawbacks. For a water trap to work effectively, it must be positioned at a point along its respective hose that is lowest in elevation such that any liquid water that is caused to condense from the respiratory gases is caused by the force of gravity to proceed toward the water trap, instead of pooling elsewhere within the hose. This requires some deliberate effort on the part of those who use such hoses and caregivers who prepare such hoses for use to ensure that the manner in which such hoses are installed and used does indeed result in the water traps being at the point of lowest elevation along the hoses. However, even if this is successful, each of the water traps holds a finite volume of liquid, and is therefore required to be opened and emptied on a regular basis to prevent overfilling. Also of concern is the possibility of the liquid within a water trap collecting and growing pathogens that may then propagate into the respiratory gases passing through the hoses, and thereby potentially infect the patient.

Another prior art effort to address such issues is to lay heating wires inside each of such hoses to raise the temperature of the gases therein to be higher than the dew point, thereby avoiding the occurrence of condensation altogether. Unfortunately, it has been found that simply laying heating wires within a hose results in uneven heating of the gases therein, thereby possibly leaving portions of the hose with a temperature that is still low enough relative to the dew point of the gases therein to allow condensation to occur.

Other issues exist in prior art heated respiratory hose assemblies beyond that of condensation. The heating of such assemblies often entails the use of a temperature sensor that must be inserted at the correct location among the circulatory flow of gases to and from the patient to be effective. Also, many medical devices also employ a gas flow sensor to provide continual confirmation of there being a flow of respiratory gases from the medical device to the patient, and this sensor must also be positioned at the correct location among the circulatory flow of gases to and from the patient to be effective. Unfortunately, many prior art heated respiratory hose assemblies use numerous individual fittings to connect the lengths of hose together to form the assembly, and to connect the assembly to both the medical device and the face mask, endotracheal tube or tracheostomy stoma at the patient end of the assembly. These numerous fittings often include separate fittings for the locations of the flow and temperature sensors, thereby providing opportunities for errors to occur in the connection and placement of these sensors.

SUMMARY

The present invention addresses such needs and deficiencies as are explained above by providing a heated respiratory hose assembly that includes a pair of heated hoses and various fittings to convey respiratory gases in a closed circuit between a medical device, such as a ventilator or CPAP device, and a patient. Such a hose assembly may be used in a medical environment, such as a hospital, outpatient care facility or other medical facility, or a non-medical environment, such as a patient's home or workplace. Such a hose assembly may incorporate a relatively minimal set of components to reduce opportunities for errors in assembling those components, as well as connecting various sensors thereto, as part of preparing the hose assembly for use.

Each hose of the heated respiratory hose assembly may incorporate heating wires into its support helix to enable even distribution of the heat generated by the heating wires within the interior of the hose. The heating wires may be positioned within the support helix at a location closer to the interior of the hose and in a manner that uses much of the material of the support helix as an insulator against the environment external to the hose to cause a greater proportion of the heat generated by the heating wires to radiated into the interior of the hose, rather than wastefully radiated into the environment external to the hose. To achieve such placement, a bead of plastics material that forms the support helix may be extruded around the heating wires as the heating wires are fed through the extruder that extrudes the bead of plastics material during formation of the hose. Additionally, tension may be exerted on the heating wires during formation of the hose to cause the heating wires to be drawn through plastics material of the bead, while still molten, and closer to the interior of the hose.

Each hose of the heated respiratory hose assembly may incorporate a pair of hose fittings, one at each end of each hose. Each such hose fitting may be formed of rigid plastics material and may be shaped and sized to enable connection of its corresponding end of a hose to a medical device or to a face mask, endotracheal tube, tracheostomy stoma or other component worn by or otherwise carried by a patient, and may do so directly or through at least one other component interposed therebetween. Each such hose fitting may be permanently coupled to its corresponding end of a hose by an undermold coupling formed of flexible plastics material to provide a gas-tight seal between the fitting and its corresponding end of the hose, and/or to provide a strain relief to prevent damage to the hose where the end of the hose is coupled to its corresponding fitting.

Each undermold coupling may be formed as a single piece of the flexible plastics material, and may include a generally cylindrical tubular portion and at least one ladder-like grating. Threads may be formed on the interior surface of the cylindrical tubular portion to enable the cylindrical tubular portion to be threaded onto the exterior of an end of a hose as part of coupling the undermold coupling to an end of a hose. Each hose fitting may be formed as a single piece of the rigid plastics material, and may include a generally cylindrical tubular portion. The cylindrical tubular portion may have a slightly larger diameter than the cylindrical tubular portion of its corresponding undermold coupling to receive and closely surround the cylindrical tubular portion of its corresponding undermold coupling therein.

A set of slots may be formed through a portion of the cylindrical wall of the cylindrical tubular portion of each hose fitting to interact with the at least one ladder-like grating of the corresponding undermold coupling as part of forming a permanent mechanical coupling between the fitting and the corresponding undermold coupling. As the cylindrical tubular portion of an undermold coupling is received within the cylindrical tubular portion of a hose fitting, a ladder-like grating of the undermold coupling may be hinged or may be otherwise partly pulled away from contact with the exterior of the cylindrical tubular portion of the undermold coupling to allow portions of the ladder-like grating to be positioned to overlie, and then extend into and through the slots formed through the cylindrical wall of the cylindrical tubular portion of the hose fitting. In so extending through the slots, those portions of the ladder-like grating are allowed to come back into contact with the exterior of the cylindrical tubular portion of the undermold coupling. Such an assembled combination of a hose fitting and a corresponding undermold coupling may then be heated to cause bonding of the flexible plastics material of the undermold coupling to the rigid plastics material of the hose fitting to form a gas-tight seal therebetween, and to cause bonding between the portions of the ladder-like grating that extend through the slots and the exterior surface of the cylindrical tubular portion of the undermold to aid in permanently mechanically interlocking the hose fitting to the undermold.

At one end of each hose, the support helix may be partially unwound, and the unwound end of the support helix may be extended at least partially within the corresponding hose fitting to an electrical connector through which the heating wires within the support helix may receive electrical power. At the electrical connector, the ends of the heating wires at the unwound end of the support helix may each be directly soldered to, or otherwise directly electrically connected to, an electrical contact of the electrical connector to. In embodiments in which the hose fitting is a Y-fitting, a T-fitting, or some other form of three-way fitting, such an electrical connector may be carried within a plug that may be carried within, and may entirely close, one of the three cylindrical connections of the hose fitting. In this way, one of the three cylindrical connections of the hose fitting through which gases may have otherwise been caused to flow may be repurposed to serve as an electrical connection point.

In other embodiments, the electrical connector may be located entirely outside of the hose fitting. In such embodiments, the unwound end of the support helix may be caused to further extend out of the hose fitting and to the location of the electrical connector in the environment external to the hose fitting and external to the corresponding hose. The portion of the unwound end of the support helix that extends out of the hose fitting may be sheathed in heat-shrink tubing or other material to provide a degree of physical protection to that portion of the unwound end of the support helix. Such heat-shrink tubing or other material providing such a sheath may also provide thermal insulation to prevent a patient or other person who comes into contact with that portion of the unwound end of the support helix being burned by the heat emitted by the heating wires extending therethrough. In this way, the portion of the unwound end of the support helix that extends outside of the hose fitting is repurposed to serve as a "pigtail" to enable an electrical connection to a medical device to provide electric power to the heating wires within the support helix.

BRIEF DESCRIPTION OF THE DRAWINGS

A fuller understanding of what is disclosed in the present application may be had by referring to the description and claims that follow, taken in conjunction with the accompanying drawings, wherein:

FIG. 4E is a cross-sectional view of a portion of the hose of FIG. 4A during the making thereof, and showing details of combining the support helix and wall thereof.

FIG. 4F is another cross-sectional view of the portion of the hose shown in FIG. 4E during the making thereof, and showing details of the bonding of the support helix to the wall thereof and of the drawing of the heating wires thereof toward the interior of the hose.

FIG. 7A is a partial elevational view of either the inspiratory hose assembly or the expiratory hose assembly of the embodiment of the heated respiratory hose assembly of FIG. 3B.

DETAILED DESCRIPTION

Figure 1A:
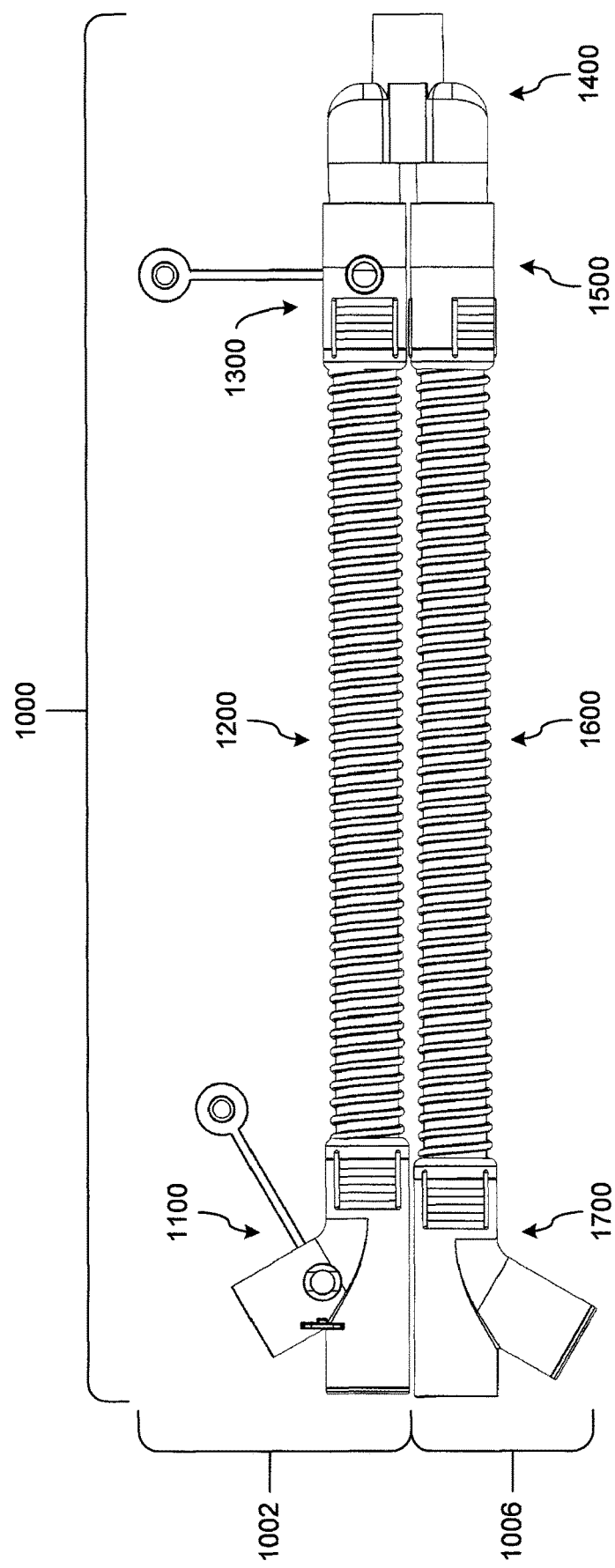
FIG. 1A is an elevational view of an example embodiment of a heated respiratory hose assembly.

FIGS. 1A through 1E, taken together, depict aspects of a novel heated respiratory hose assembly 1000 that addresses many of the shortcomings of prior art assemblies, including those discussed above. As depicted in FIG. 1A, the heated respiratory hose assembly 1000 may include two sub-assemblies, specifically an inspiratory hose assembly 1002 by which respiratory gases may be conveyed from a medical device to a patient to breathe in, and an expiratory hose assembly 1006 by which respiratory gases breathed out by the patient may be conveyed back to the medical device. This circular flow is also conceptually depicted in FIG. 2A.

The inspiratory hose assembly 1002 includes an inspiratory inlet fitting 1100 for connection to a medical device 990 (e.g., a ventilator or CPAP device), an inspiratory outlet fitting 1300 for connection to a parallel Y-fitting 1400 at the patient end, and an inspiratory hose 1200 to convey respiratory gases received by the inspiratory inlet fitting 1100 from the medical device 990 and to the inspiratory outlet fitting 1300 to be conveyed onward to the patient through the parallel Y-fitting 1400. Correspondingly, the expiratory hose assembly 1006 includes an expiratory inlet fitting 1500 for connection to the parallel Y-fitting 1400 at the patient end, an expiratory outlet fitting 1700 for connection to the medical device 990, and an expiratory hose 1600 to convey respiratory gases received by the expiratory inlet fitting 1500 from the patient through parallel Y-fitting 1400 and to the expiratory outlet fitting 1700 to be conveyed onward to the medical device 990. At the patient end, the parallel Y-fitting 1400 may connect the heated respiratory hose assembly 1000 to a face mask 940, an endotracheal tube 940, a tracheostomy stoma 940 (see FIG. 2A) or other component.

Figure 1B:
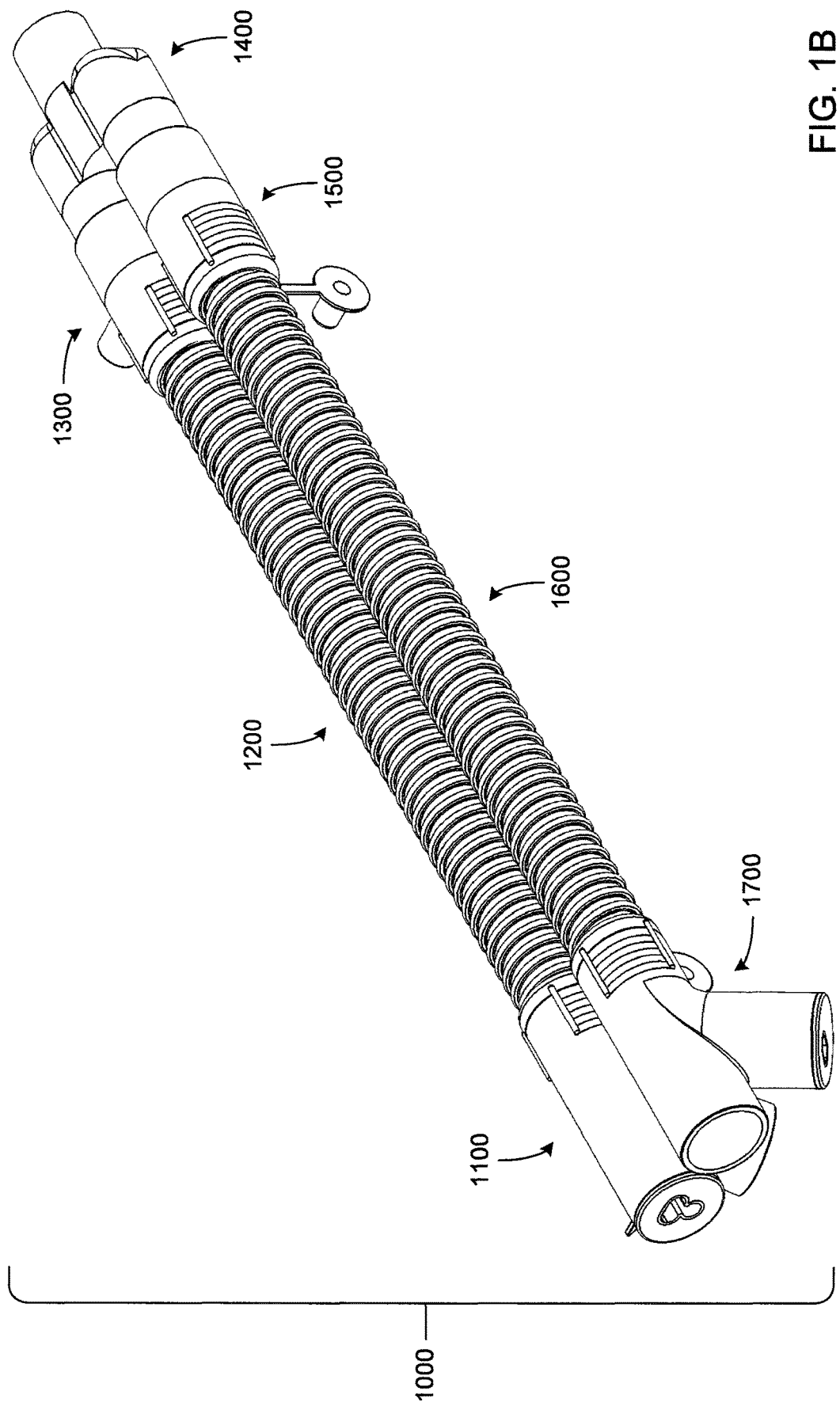
FIG. 1B is a perspective view of the heated respiratory hose assembly of FIG. 1A showing details of electrical connectors thereof.
Figure 1C:
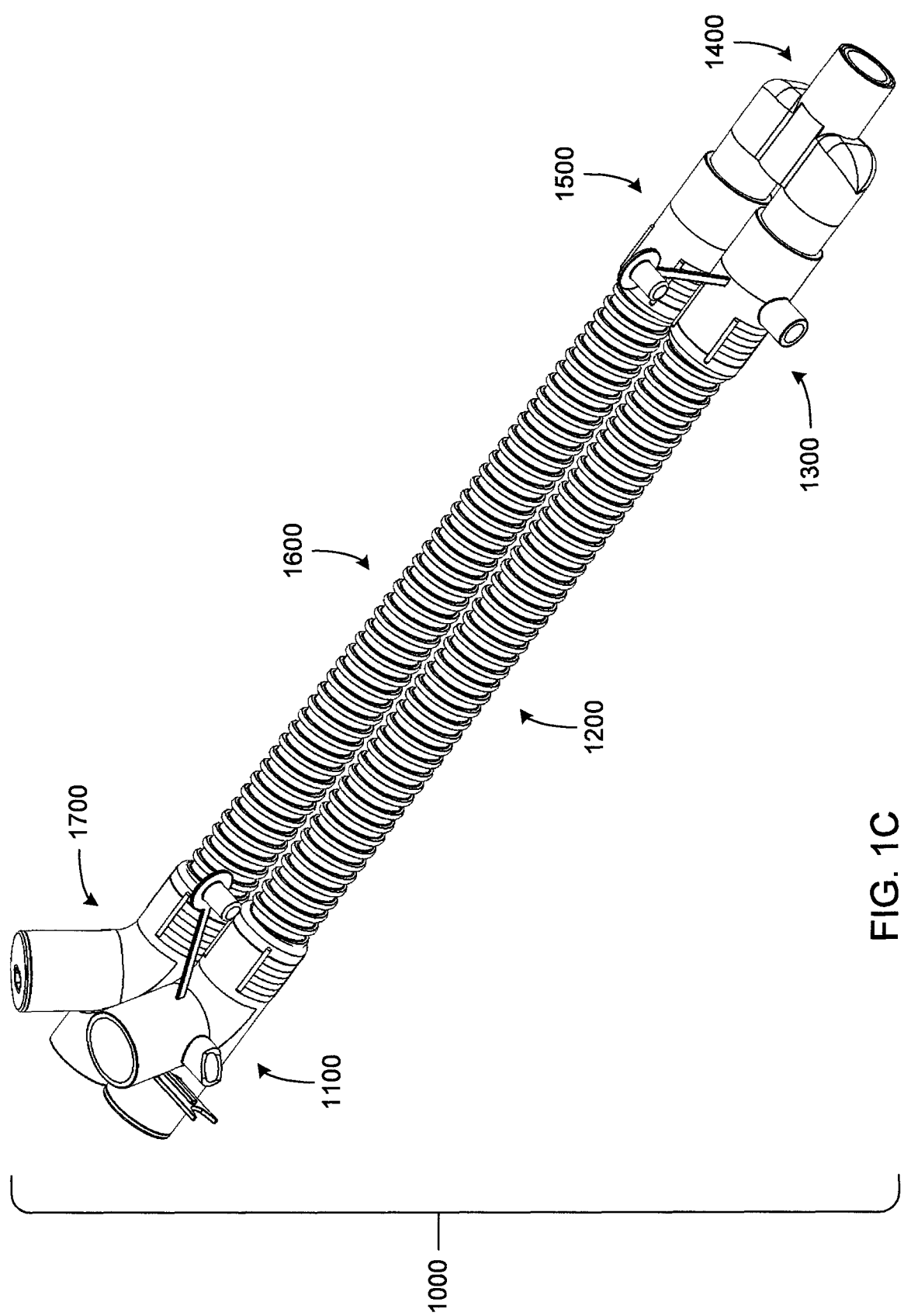
FIG. 1C is another perspective view of the heated respiratory hose assembly of FIG. 1A.
Figure 1D:
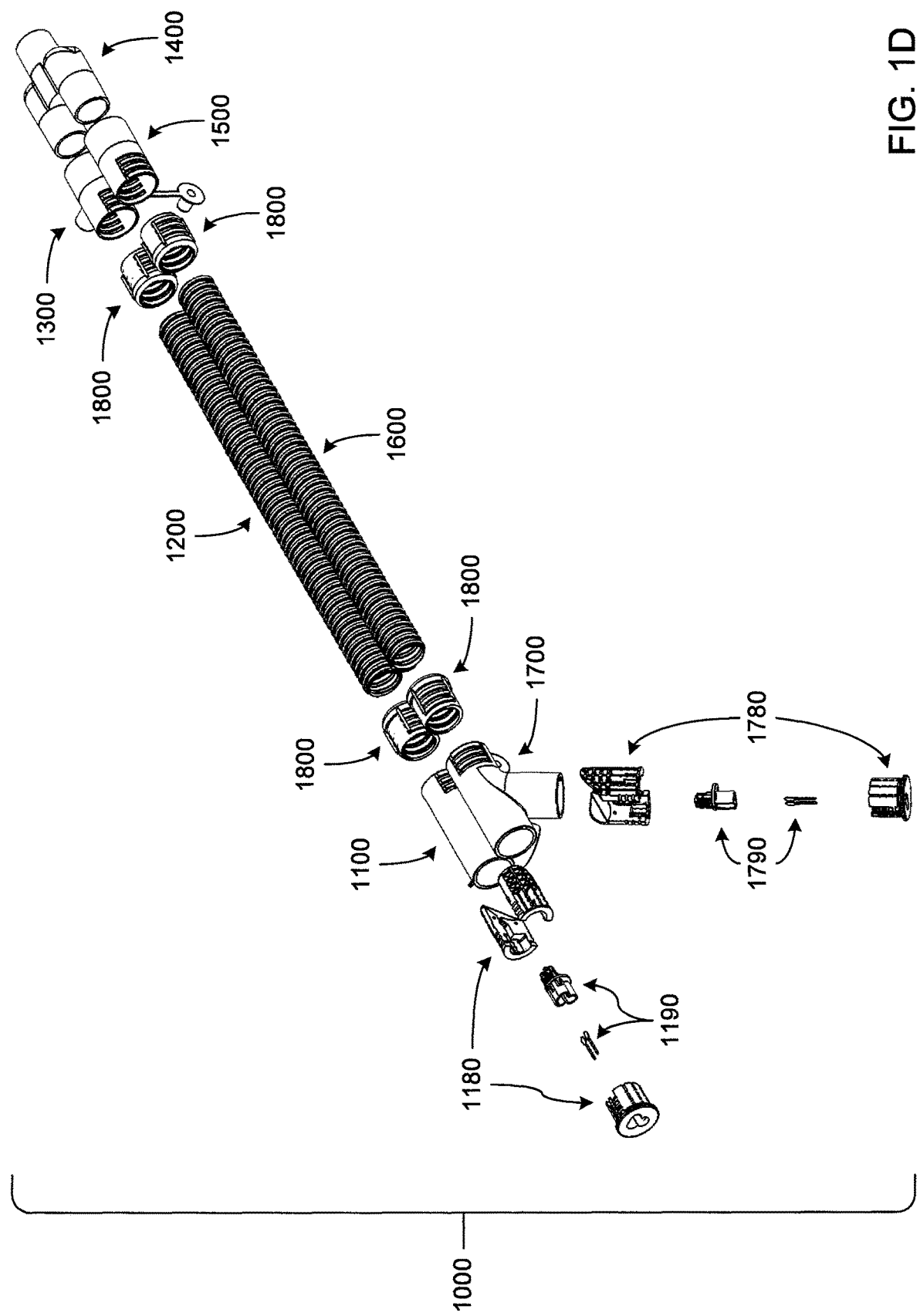
FIG. 1D is an exploded perspective view of the heated respiratory hose assembly of FIG. 1A showing details of the electrical connectors thereof and details of the coupling of hoses to hose fittings thereof.
Figure 1E:
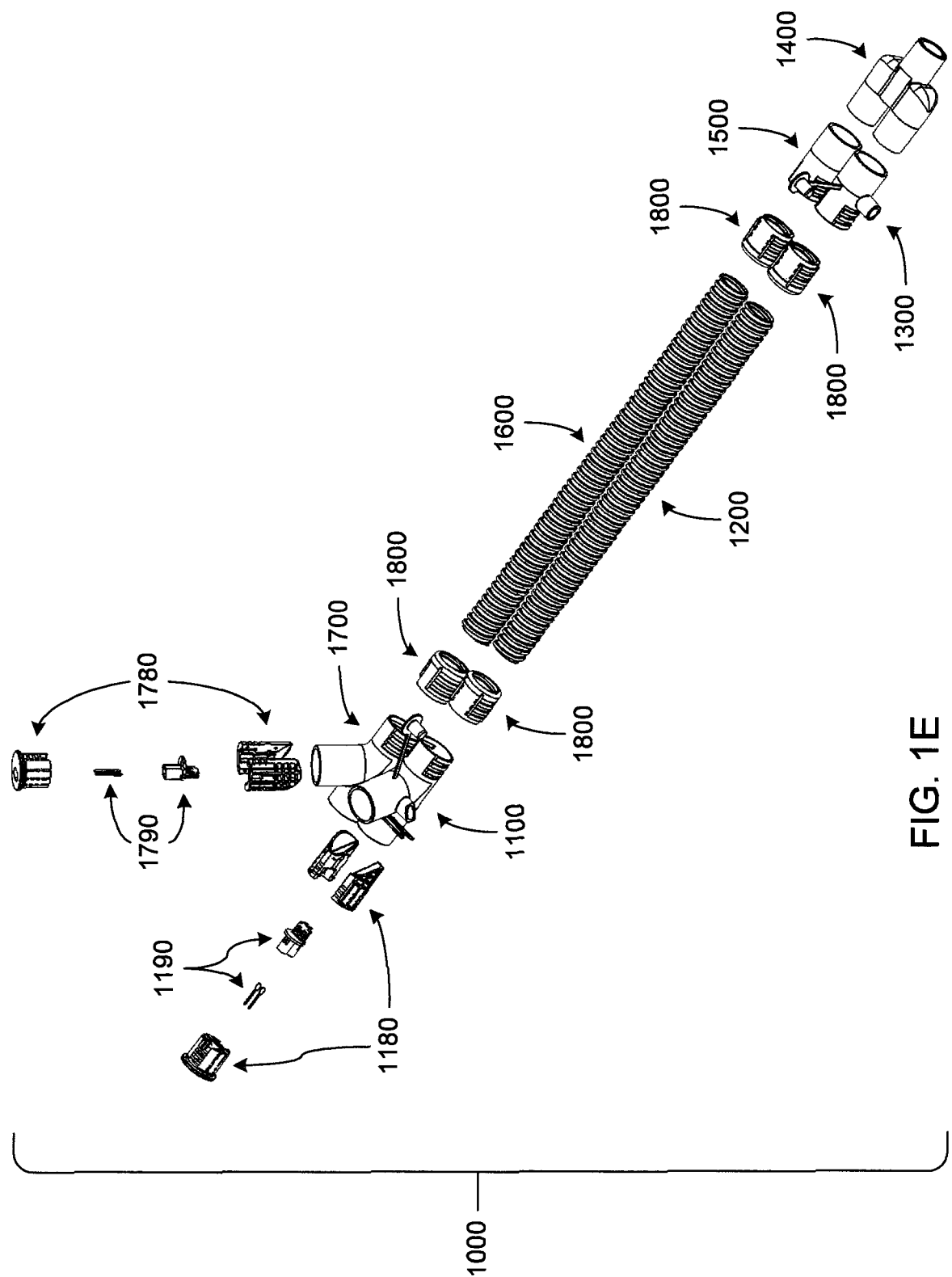
FIG. 1E is another exploded perspective view of the heated hose assembly of FIG. 1A.

Each of FIGS. 1B and 1C provide a perspective view of one embodiment of the heated respiratory hose assembly 1000 in which the inspiratory inlet fitting 1100 and the expiratory outlet fitting 1700 are both implemented with 120-degree Y-fittings in which there is both a straight-through path for either gases or wiring to pass from the hoses 1200 and 1600, respectively, and an angled path that branches off from the straight-through path at a 120-degree angle relative to the connections to the hoses 1200 and 1600, respectively. Each of FIGS. 1D and 1E provide an exploded perspective view of this embodiment. In this embodiment, one of the connections of each of the Y-fittings 1100 and 1700 is occupied by a plug 1180 and 1780 that carries an electrical connector 1190 and 1790, respectively. In the depicted variant of this embodiment, at the inspiratory inlet fitting 1100, the straight-through connection (relative to the connection to the inspiratory hose 1200) is occupied by the plug 1180 that carries the electrical connector 1190 by which electric power is able to be provided to a pair of heating wires incorporated into the support helix of the inspiratory hose 1200, as will be explained in greater detail. Correspondingly, in this depicted variant of this embodiment, at the expiratory outlet fitting 1700, the 120-degree connection (relative to the connection to the expiratory hose 1600) is occupied by the plug 1780 that carries the electrical connector 1790 by which electric power is able to be provided to a pair of heating wires incorporated into the helix of the expiratory hose 1600, as will also be explained in greater detail.

It should be noted that, despite such a depiction of the use of particular ones of the three connections of each of the Y-fittings 1100 and 1700 in FIGS. 1A-E as being occupied by plugs carrying electrical connectors, different connections of the Y-fittings 1100 and 1700 may be so occupied in other variants of the embodiment of the heated respiratory hose assembly 1000 of FIGS. 1A-E. Also, and as will be depicted in subsequent figures, it should be noted that other embodiments of the heated respiratory hose assembly 1000 may employ hose fitting(s) 1100 and/or 1700 of an entirely different type that may each provide a different selection of connections from which one may be chosen to be occupied by a plug carrying an electrical connector.

Figure 2A:
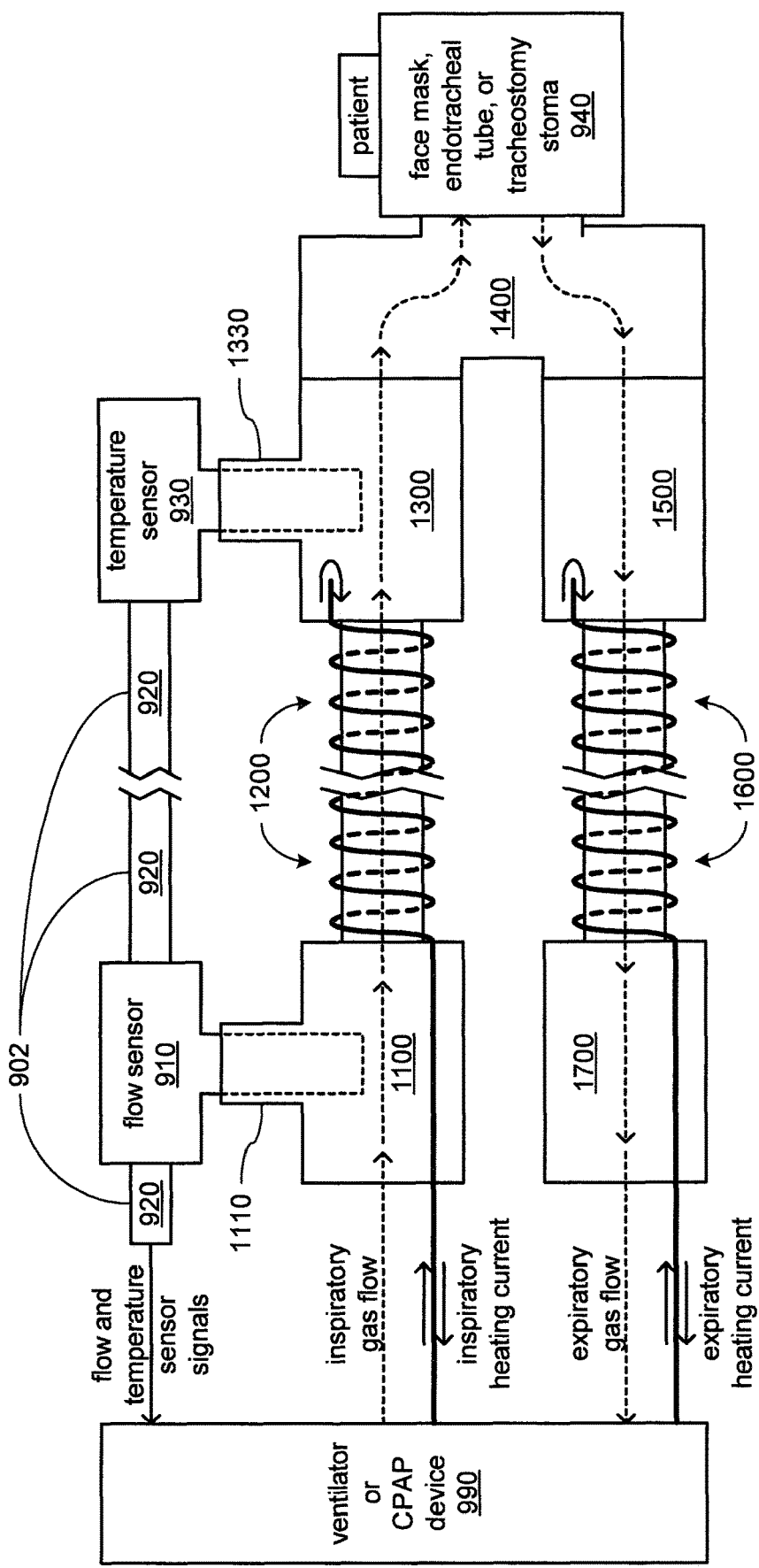
FIG. 2A is a block diagram of heated respiratory hose assembly of FIG. 1A showing details of the flow of respiratory gases therethrough and the monitoring of flow and temperature thereof.
Figure 2B:
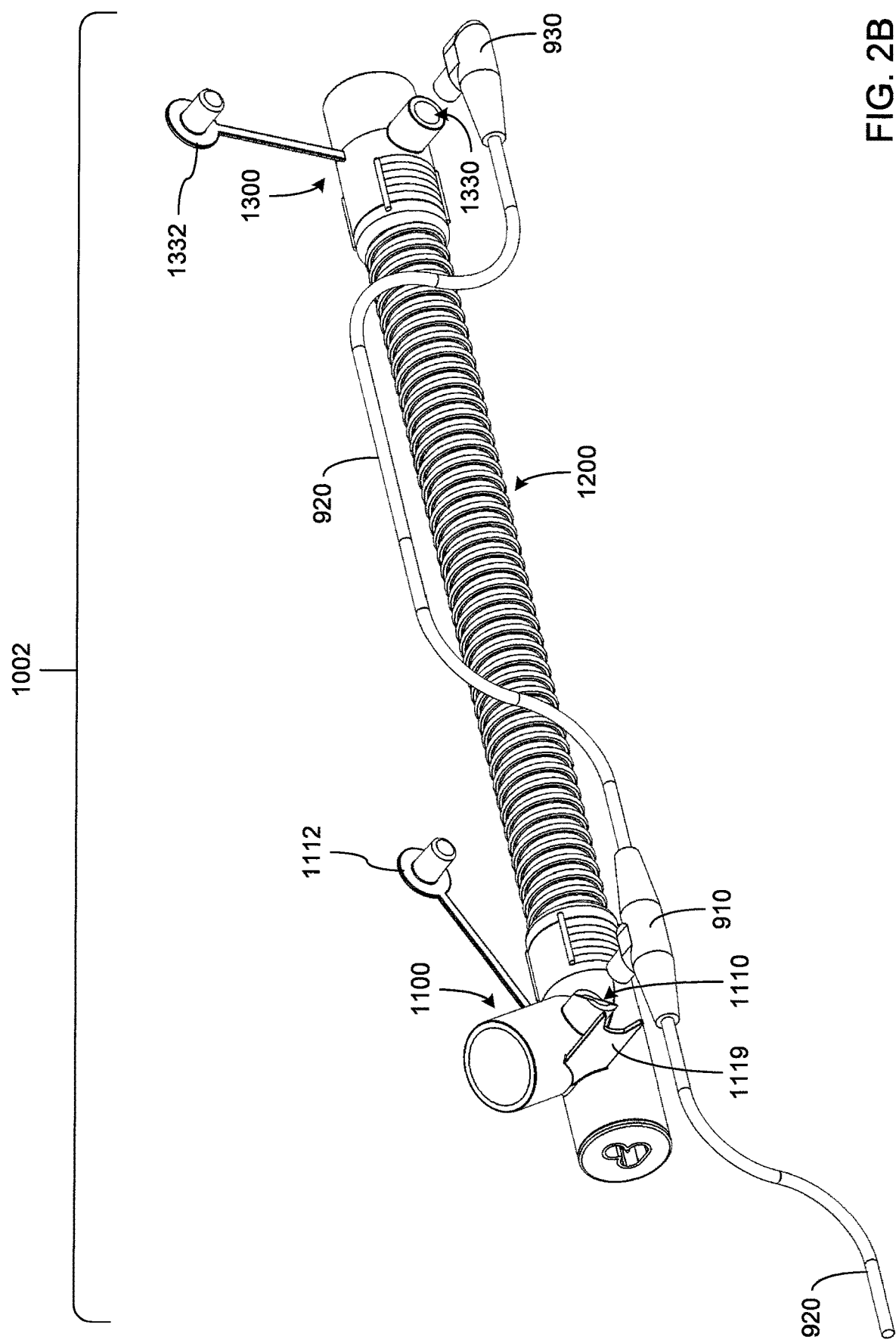
FIG. 2B is a perspective view of the inspiratory hose assembly of the heated respiratory hose assembly of FIG. 1A showing details of a sensor harness that is to be connected thereto.
Figure 2C:
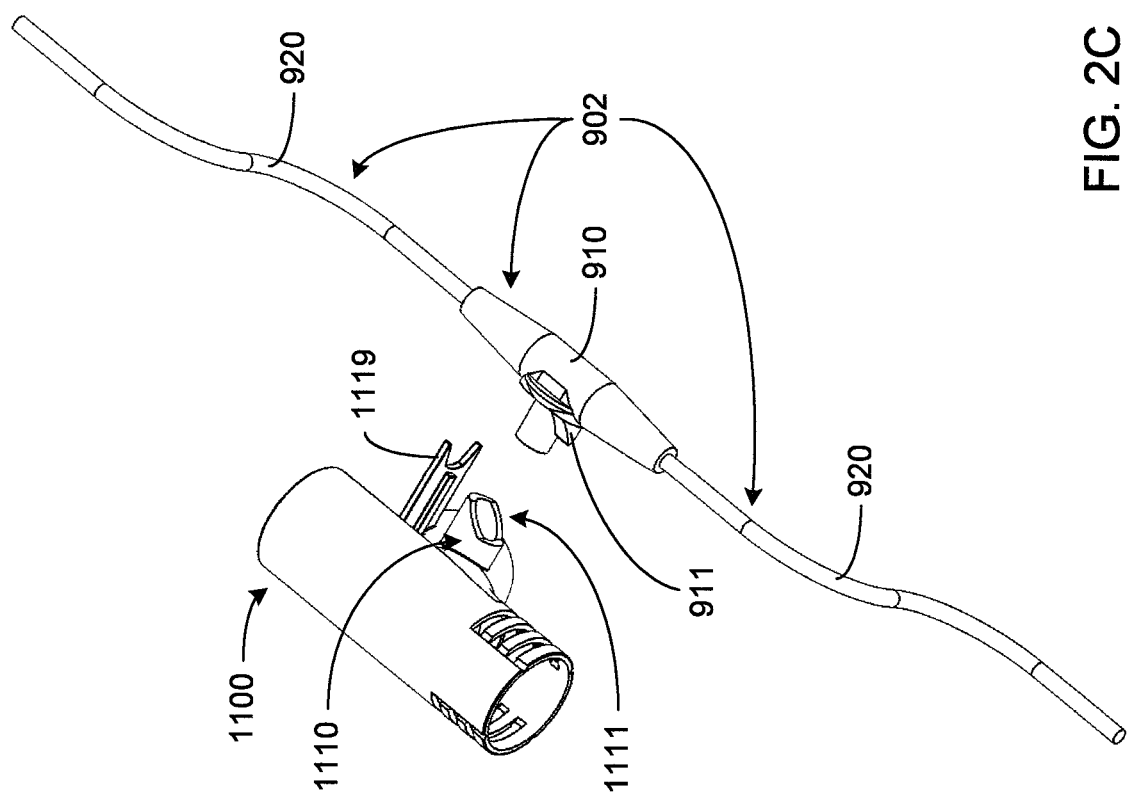
FIG. 2C is a perspective view of the inspiratory inlet fitting of the inspiratory hose assembly of FIG. 2B showing features of the inspiratory inlet fitting to aid in correctly connecting a flow sensor of the sensor harness to enable correct operation thereof.

FIGS. 2A through 2C, taken together, depict aspects of the use of sensors with at least the inspiratory hose assembly 1002 of the heated respiratory hose assembly 1000 to monitor the flow and/or temperature of at least respiratory gases from the medical device 990 to the patient. As depicted, the inspiratory inlet fitting 1100 may additionally include a flow sensor port 1110 formed through a portion of the wall of the inspiratory inlet fitting 1100. The flow sensor port 1110 provides an opening into the inspiratory interior of the inlet fitting 1100 through which a flow sensor 910 of a sensor harness 902 is able to be inserted to continually confirm the flow of respiratory gases from the medical device 990 and toward the patient at the patient end. As will be explained in greater detail, the flow sensor 910 is directional in nature such that it must be installed within the flow sensor port 1110 in a correct orientation to function properly.

As depicted, the inspiratory outlet fitting 1300 may additionally include a temperature sensor port 1330 formed through the wall of the inspiratory outlet fitting 1300. The temperature sensor port 1330 provides an opening into the interior of the inspiratory outlet fitting 1300 by which a temperature sensor 930 of the sensor harness 902 is able to be inserted to continually monitor the temperature of the respiratory gases output by the medical device 990 at a location towards the patient end (i.e., just before those respiratory gases are conveyed through the inspiratory outlet fitting 1300 and into the parallel Y-fitting 1400 to be conveyed onward to the patient).

In some embodiments, and as can best be seen in FIG. 2B, the inspiratory inlet fitting 1100 may carry a port plug 1112 that may be used to close and seal the flow sensor port 1110 in situations where at least the inspiratory hose assembly 1002 is used without the flow sensor 910 installed within the flow sensor port 1110. Alternatively or additionally, the inspiratory outlet fitting 1300 may carry a port plug 1332 that may similarly be used to close and seal the temperature sensor port 1330 in situations where at least the inspiratory hose assembly 1002 is used without the temperature sensor 930 installed within the temperature sensor port 1330. As depicted, the port plugs 1112 and 1332 may be carried by the hose fittings 1100 and 1300, respectively, by being attached thereto with elongate stretches of the rigid plastics material of the hose fittings 1100 and 1300 that are long and thin enough as to be sufficiently flexible that the port plugs 1112 and 1332 are able to be maneuvered to and from the ports 1110 and 1330, respectively, for a relatively limited number of times without the elongate stretches breaking.

As also depicted, the flow sensor 910 and the temperature sensor 930 may be physically connected by a length of cabling 920 of the sensor harness 902 that is meant to follow the length of the inspiratory hose 1200, and by which signals of the temperature sensor 930 are conveyed toward the location of the flow sensor 910. As can also be seen, there may also be another length of cabling 920 of the sensor harness 902 that extends from the flow sensor 910 and towards the medical device 990 to convey the signals of both sensors 910 and 930 to the medical device 990.

Referring more specifically to FIG. 2A, during operation of the medical device 990, respiratory gases to be breathed in by a patient are conveyed from the medical device 990, through the inspiratory inlet fitting 1100, then the inspiratory hose 1200, then the inspiratory outlet fitting 1300, then the parallel Y-fitting 1400, and then to the patient via still another component, such as a face mask 940, an endotracheal tube 940, a tracheostomy stoma 940 or other component. Also during operation of the medical device 990, respiratory gases breathed out by the patient are conveyed from the patient through such a component (e.g., the face mask 940, the tracheal tube 940, the tracheostomy stoma 940 or other component), then the parallel Y-fitting 1400, then the expiratory inlet fitting 1500, then the expiratory hose 1600, then the expiratory outlet fitting 1700, and onward to the medical device 990.

While this circular flow of respiratory gases goes on between the medical device 990 and the patient, the medical device 990 monitors the flow sensor 910 to ensure that respiratory gases to be breathed in by the patient are, in fact, output by the medical device 990 and into the inspiratory hose assembly 1002 of the heated respiratory hose assembly 1000 towards the patient. If a lack of flow and/or flow in a wrong direction is detected by the sensor 910, then the medical device 990 may sound an alarm and/or provide some other audio and/or visual indication of the lack of flow and/or the incorrect direction of flow. Also while this circular flow of respiratory gases goes on between the medical device 990 and the patient, the medical device monitors the temperature sensor 930 to ensure that the respiratory gases that reach the patient end of the inspiratory hose 1200 are of a correct temperature, both to prevent condensation within the inspiratory hose 1200, and for the health of the patient.

Referring more specifically to FIG. 2C, as just discussed, the directional nature of the flow sensor 910 requires correct installation of the flow sensor 910 within the interior of the inspiratory inlet fitting 1100 to ensure that it is caused to sense the flow of respiratory gases towards the patient with a correct orientation. Otherwise, it may be that the flow sensor 910 is caused to at least attempt to detect a flow of respiratory gases in a direction opposite of the correct direction towards the patient. The inspiratory inlet fitting 1100 may carry a flow sensor guide 1119 adjacent to the flow sensor port 1110 to cooperate with the shape of a portion of the exterior of the flow sensor 910 to aid in correctly positioning the flow sensor 910 relative to the flow sensor port 1110 and the interior of the inspiratory inlet fitting 1100. Alternatively or additionally, the flow sensor port 1110 may be formed to include a short tube-like portion with a bevel cut 1111 to interact with an orientation key 911 carried on a portion of the exterior of the flow sensor 910 to aid in correctly positioning the flow sensor 910 relative to the flow sensor port 1110 and the interior of the inspiratory inlet fitting 1100.

The medical device 990 may selectively turn on and off the provision of electric power to the heating wires within the inspiratory hose 1200 and the expiratory hose 1600 to selectively apply heat thereto based on the temperature sensed by the temperature sensor 930. More specifically, and as will be explained in greater detail, each of the hoses 1200 and 1600 may incorporate at least a pair of heating wires that may be connected to the medical device 990 at one end of each of the hoses 1200 and 1600, and that may be soldered, crimped or otherwise electrically connected at the other end of each of the hoses 1200 and 1600 to form a separate closed loop of electric current through each of the hoses 1200 and 1600.

Some medical devices 990 may turn on and off the provision of electric power to the heating wires of both hoses together. Indeed, some medical devices 990 may selectively provide the very same voltage from the very same power source to the heating wires of both hoses. However, it may be the case that each of the two hoses 1200 and 1600 are to be heated to different temperatures. Thus, the heating wires employed in the two hoses 1200 and 1600 may be of different resistances and/or have other differing characteristics to bring about such a difference in temperature. More specifically, it may be deemed desirable to heat the respiratory gases being conveyed to the patient through the inspiratory hose 1200 to a higher temperature than the respiratory gases being conveyed from the patient through the expiratory hose 1600. The heating of gases conveyed to the patient may be deemed of greater importance for such purposes as achieving a particular higher temperature to help the patient maintain a particular body temperature, aid in treating the patient for a particular respiratory illness, etc. Such heating of the gases conveyed to the patient would also be intended to prevent condensation from occurring within the inspiratory hose 1200. In contrast, the heating of gases conveyed from the patient may be solely for the purpose of preventing condensation from occurring within the expiratory hose 1600.

Figure 3A:
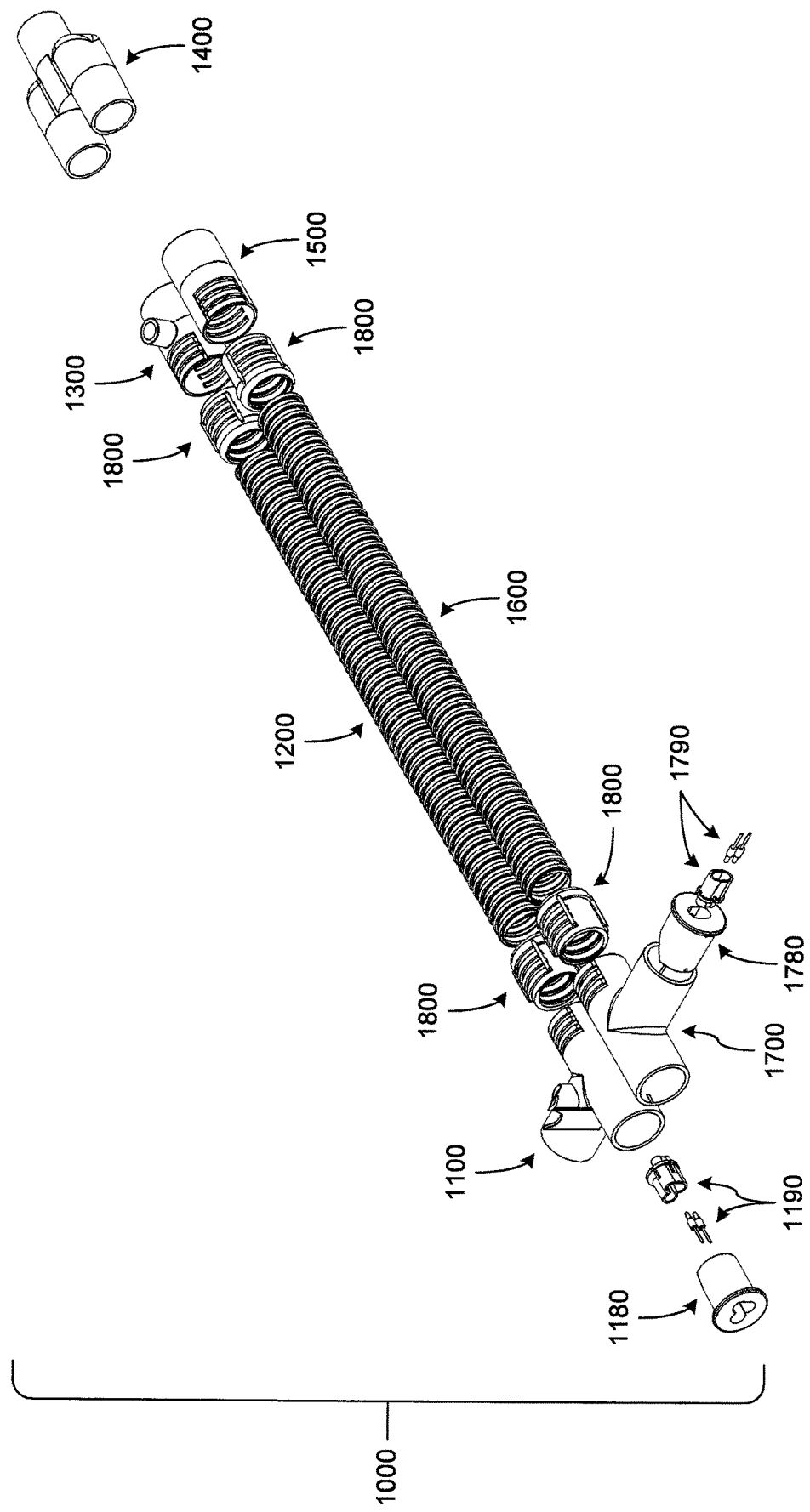
FIG. 3A is an exploded perspective view of an alternate embodiment of a heated respiratory hose assembly.
Figure 3B:
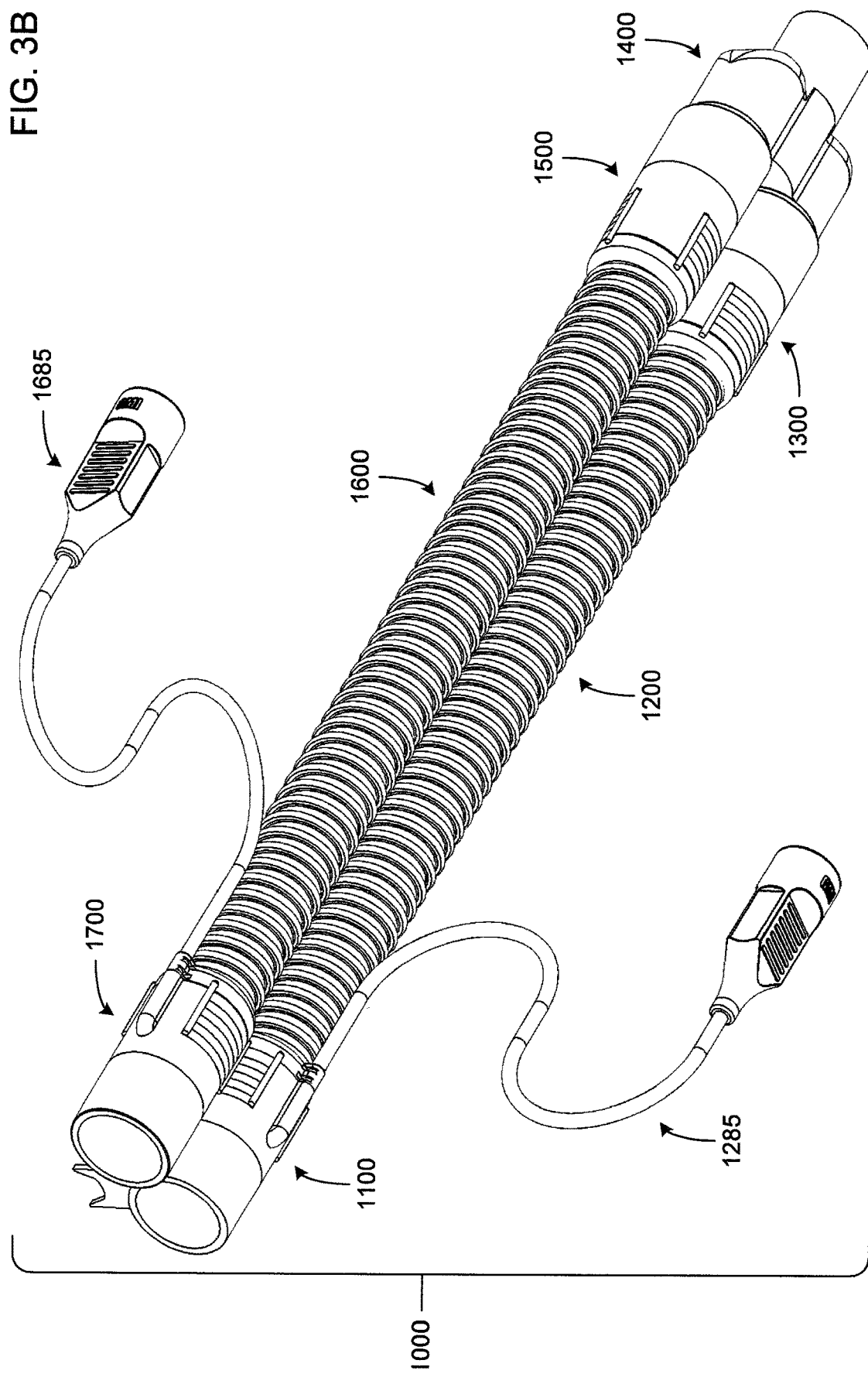
FIG. 3B is a perspective view of another alternate embodiment of a heated respiratory hose assembly.
Figure 3C:
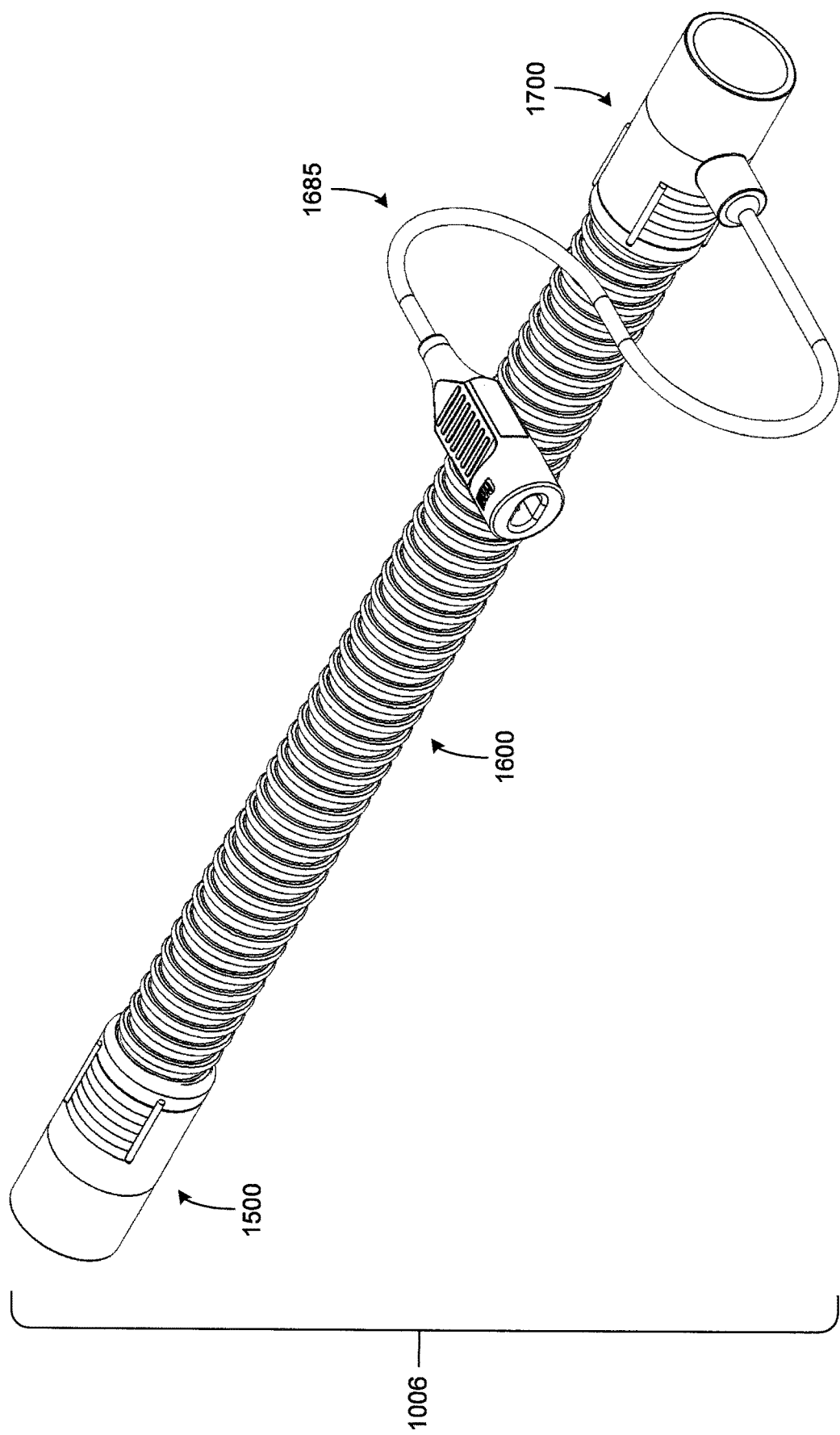
FIG. 3C is a perspective view of the inspiratory hose assembly of still another embodiment of a heated respiratory hose assembly.

Each of FIGS. 3A through 3C depict another possible embodiment of the heated respiratory hose assembly 1000 in which other possible different versions (or combinations of versions) of the inspiratory inlet fitting 1100 and the expiratory outlet fitting 1700 may be used. FIG. 3A provides an exploded perspective view of an alternate embodiment of the heated respiratory hose assembly 1000 in which the inspiratory inlet fitting 1100 and the expiratory outlet fitting 1700 are both T-fittings, instead of the 120-degree Y-fittings depicted in FIGS. 1A through 1E. FIG. 3B provides a perspective view of another alternate embodiment of the heated respiratory hose assembly 1000 in which the inspiratory inlet fitting 1100 and the expiratory outlet fitting 1700 are both through-fittings, and from each of which a pigtail 1285 and 1685 emerges by which the electrical connection to the heating wires of the hoses 1200 and 1600, respectively, are separately made. FIG. 3C provides a perspective view of the expiratory hose assembly 1006 of still another embodiment of the heated respiratory hose assembly 1000 in which at least the expiratory outlet fitting 1700 is a through-fitting from which the pigtail 1685 by which electrical connection is made to the heating wires of the expiratory hose 1600 emerges in a direction perpendicular to the direction from which the expiratory hose 1600 emerges. In contrast, the pigtails 1285 and/or 1685 depicted in the embodiment of FIG. 3B emerge from the hose respective fittings 1100 and/or 1700 in a direction that is parallel to (and alongside) the hoses 1200 and/or 1600, respectively.

It should be noted that, despite such depictions of particular alternate embodiments, still other alternate embodiments of the heated respiratory hose assembly 1000 are possible in which still other types of fittings are employed as one or both of the inspiratory inlet fitting 1100 and the expiratory outlet fitting 1700. Further, it should be noted that, despite the depictions of the inspiratory outlet fitting 1300 and of the expiratory inlet fitting 1500 being unchanged throughout these multiple depicts of differing embodiments of the heated respiratory hose assembly 1000, other embodiments are possible in which other types of fittings may be employed as one or both of the inspiratory outlet fitting 1300 and the expiratory inlet fitting 1500. Further, it should be noted that, despite the depictions of the inspiratory inlet fitting 1100 and the expiratory outlet fitting 1700 being of the same type, still other embodiments of the heated respiratory hose assembly 1000 are possible in which the inspiratory inlet fitting 1100 and the expiratory outlet fitting 1700 are of different types (e.g., one may be a Y-fitting and the other may be a T-fitting, or one may be a Y-fitting or T-fitting that carries a plug with an electrical connector and the other may be a through-fitting with a pigtail that carries another plug).

FIGS. 4A through 4F, taken together, depict various aspects of the making of the inspiratory hose 1200 and the expiratory hose 1600, including aspects of forming the support helixes 1280 and 1680 thereof to include a pair of heating wires 1290 and 1690, respectively. It should be noted that, although the helixes 1280 and 1680 are depicted as each incorporating a pair of heating wires 1290 and 1690, respectively, other embodiments of the hoses 1200 and/or 1600 are possible in which different numbers of wires (whether heating wires, or not) may be incorporated into the helixes 1280 and/or 1680, respectively, as well as other embodiments in which there may be multiple helixes that each carry one or more different wires (whether heating wires, or not).

As depicted, each of the hoses 1200 and 1600 may include a wall 1270 and 1670, respectively, that is physically supported by a corresponding one of the support helixes 1280 and 1680. As also depicted, the support helixes 1280 and 1680 may spirally wrap around the exterior of the walls 1270 and 1670, respectively, in a manner that leaves a continuous helical stretch of the walls 1270 and 1670 between adjacent coils of the support helixes 1280 and 1680 that enable the hoses 1200 and 1600, respectively, to be flexible enough to bend. Additionally, such spacing between adjacent coils of the support helixes 1280 and 1680 may be of a distance selected to allow fold(s), curve(s) and/or convolution(s) to be formed in the continuous helical stretch of the walls 1270 and 1670 therebetween to enable the hoses 1200 and 1600, respectively, to be axially stretched and compressed (i.e., lengthened or shortened along the depicted axis 101), as well as to bend.

Figure 4A:
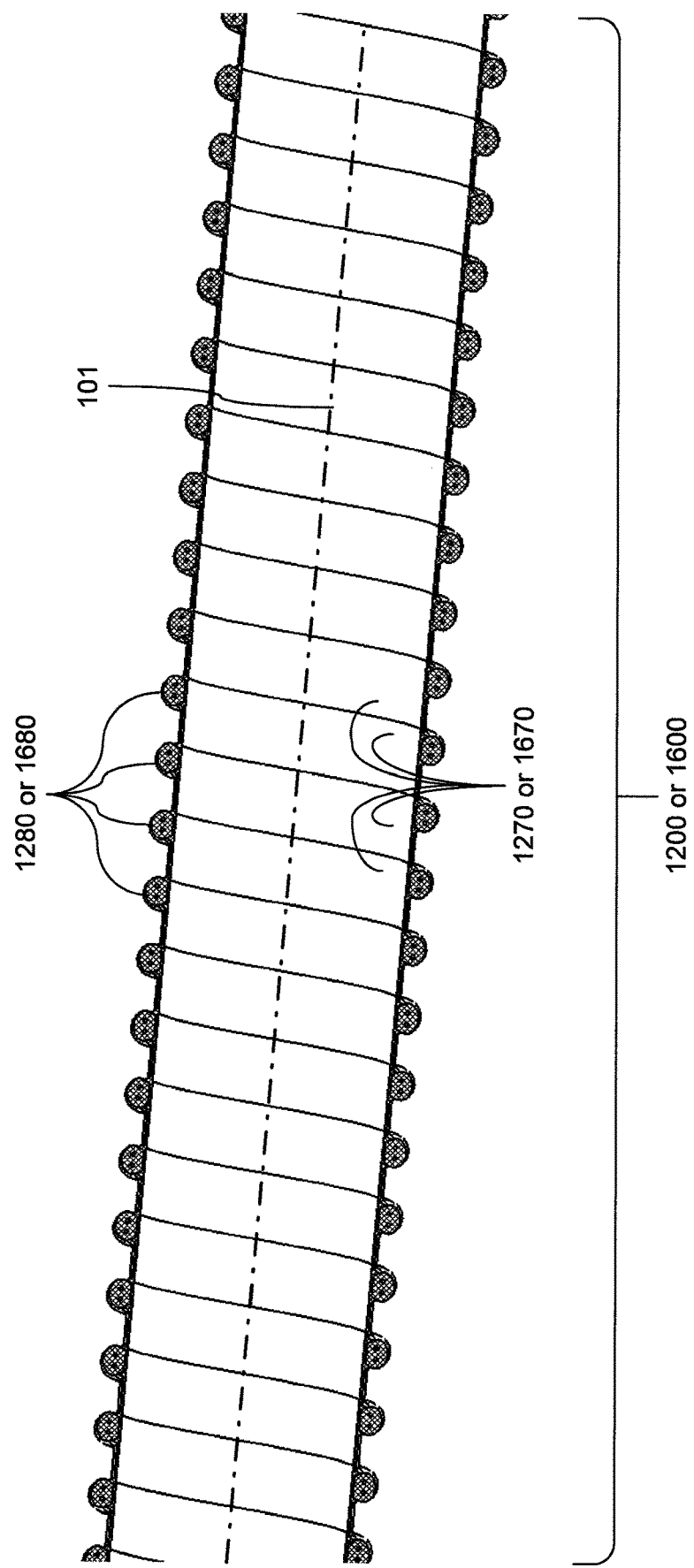
FIG. 4A is a cross-sectional view of a portion of one of the hoses of any of the embodiments of heated respiratory hose assembly of any of FIG. 1A, 3A, 3B or 3C showing details of the wall and support helix thereof.
Figure 4B:
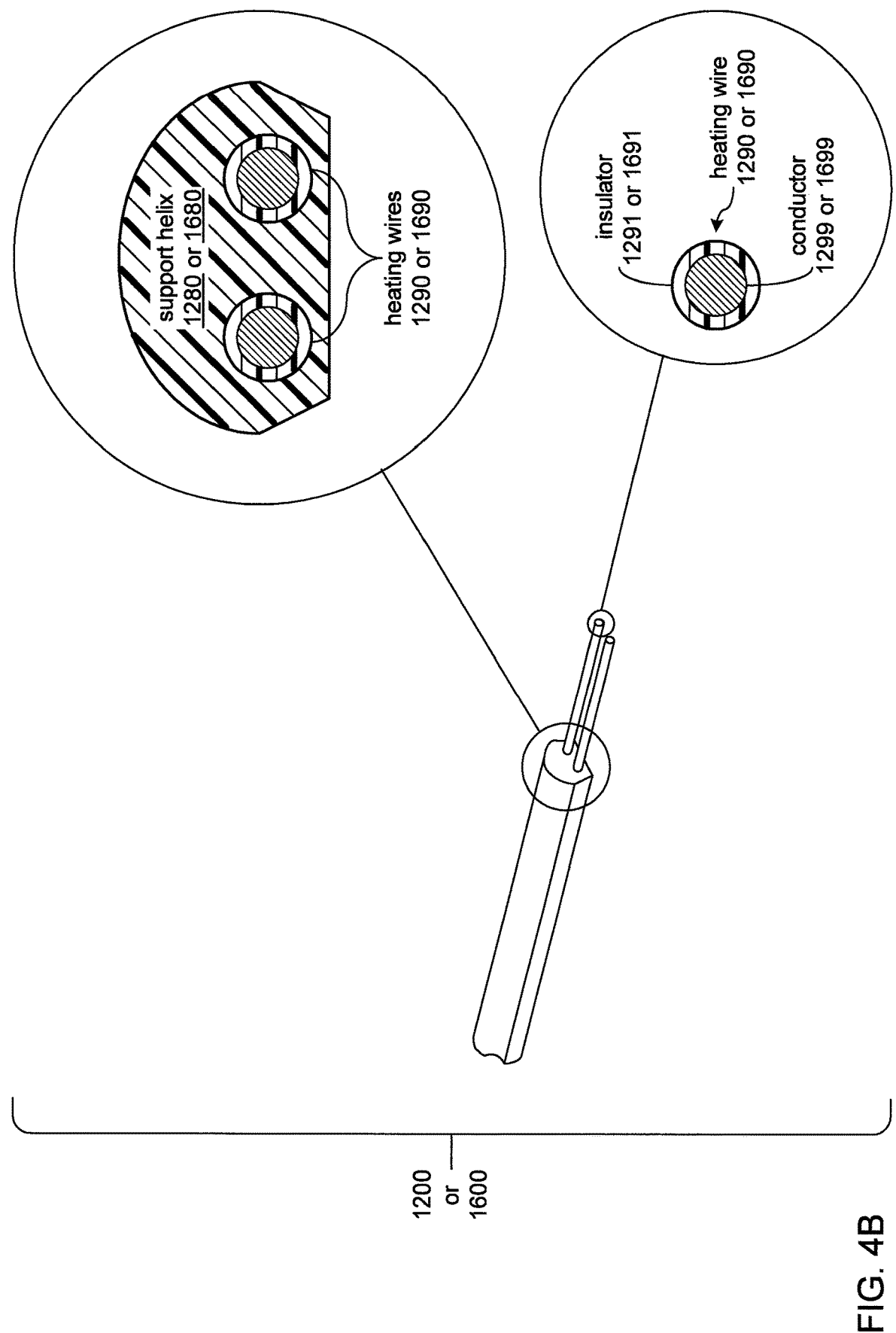
FIG. 4B is a combination of perspective and cross-sectional views of a portion of the support helix of the hose of FIG. 4A showing details of the heating wires incorporated therein.

As depicted most clearly in FIG. 4B, the heating wires 1290 and 1690 may be positioned within the flexible plastics material of the support helixes 1280 and 1680 to bring them closer to the interior of the hoses 1200 and 1600, respectively, than to the environment external thereto. In this way, much of the flexible plastics material that makes up the support helixes 1280 and 1680 is used as insulation to tend to cause the heat generated by the heating wires 1290 and 1690 to be radiated into the interiors of the hoses 1200 and 1600, respectively, instead of being wasted by being radiated into the environment external to the hoses 1200 and 1600.

As also depicted most clearly in FIG. 4B, each individual heating wire 1290 and 1690 may incorporate a conductor 1291 and 1691, and an individual insulator 1292 and 1692 in addition to the insulation provided by the flexible plastics material of the support helix 1280 and 1680, respectively. In some embodiments, the heating wire 1290 and 1690 may be a variant of magnet wire or similar wire with a selected resistance where the insulator 1292 and 1692, respectively, may be one or more layers of polymer or other type of film. As will be recognized by those skilled in the art, the insulators 1292 and 1692 may be selected to be capable of resisting temperatures expected to be encountered during heating of the hoses 1200 and 1600, respectively, but to not be capable resisting temperatures typically encountered during soldering such that electrical connections may be made to the wires 1290 and 1690 using any of a variety of soldering techniques without requiring stripping of the insulation 1292 and 1692, respectively, in preparation therefor.

Figure 4C:
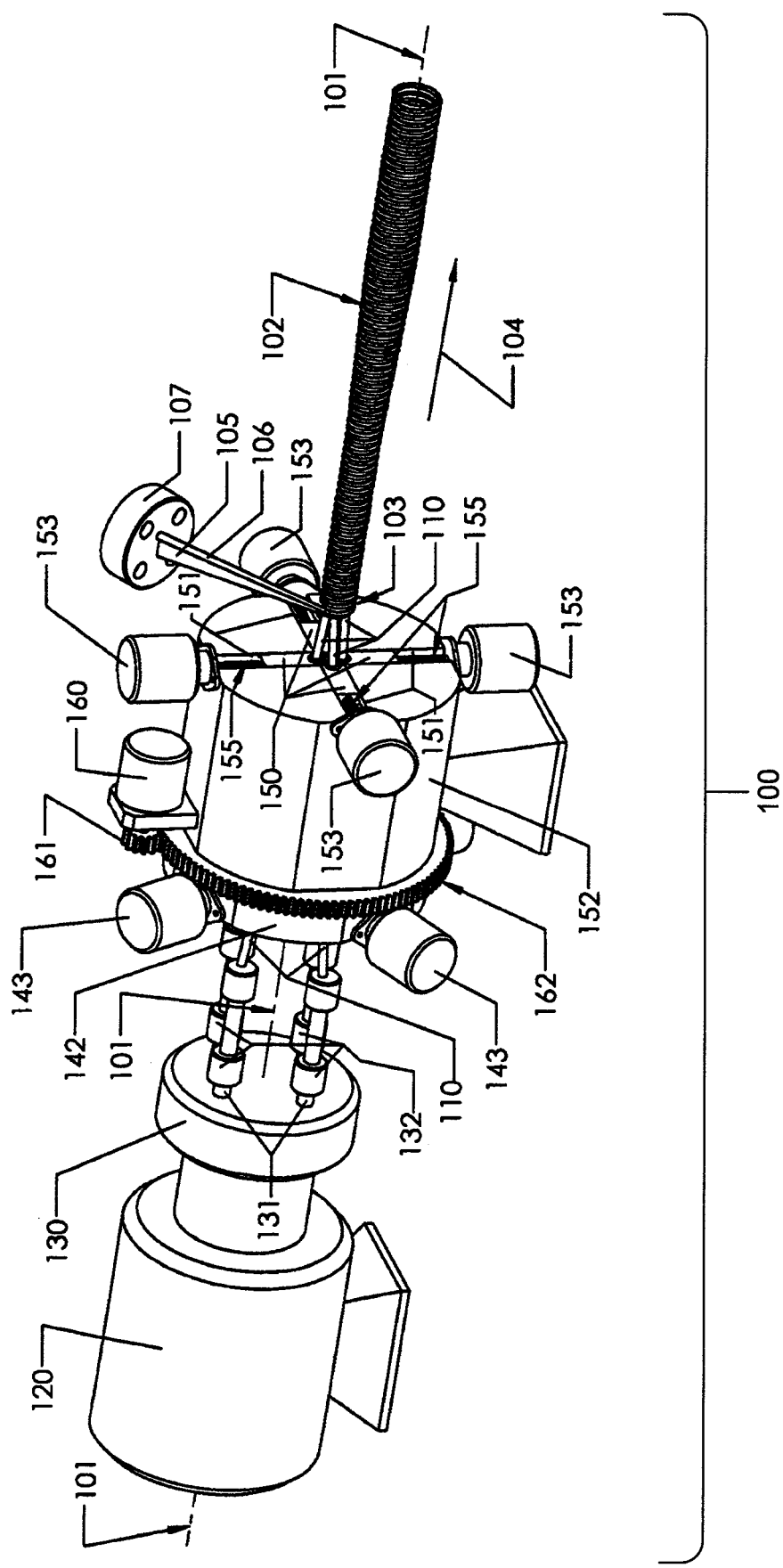
FIG. 4C is a perspective view of components of a hose making apparatus that may be adapted to make the hose of FIG. 4A.
Figure 4D:
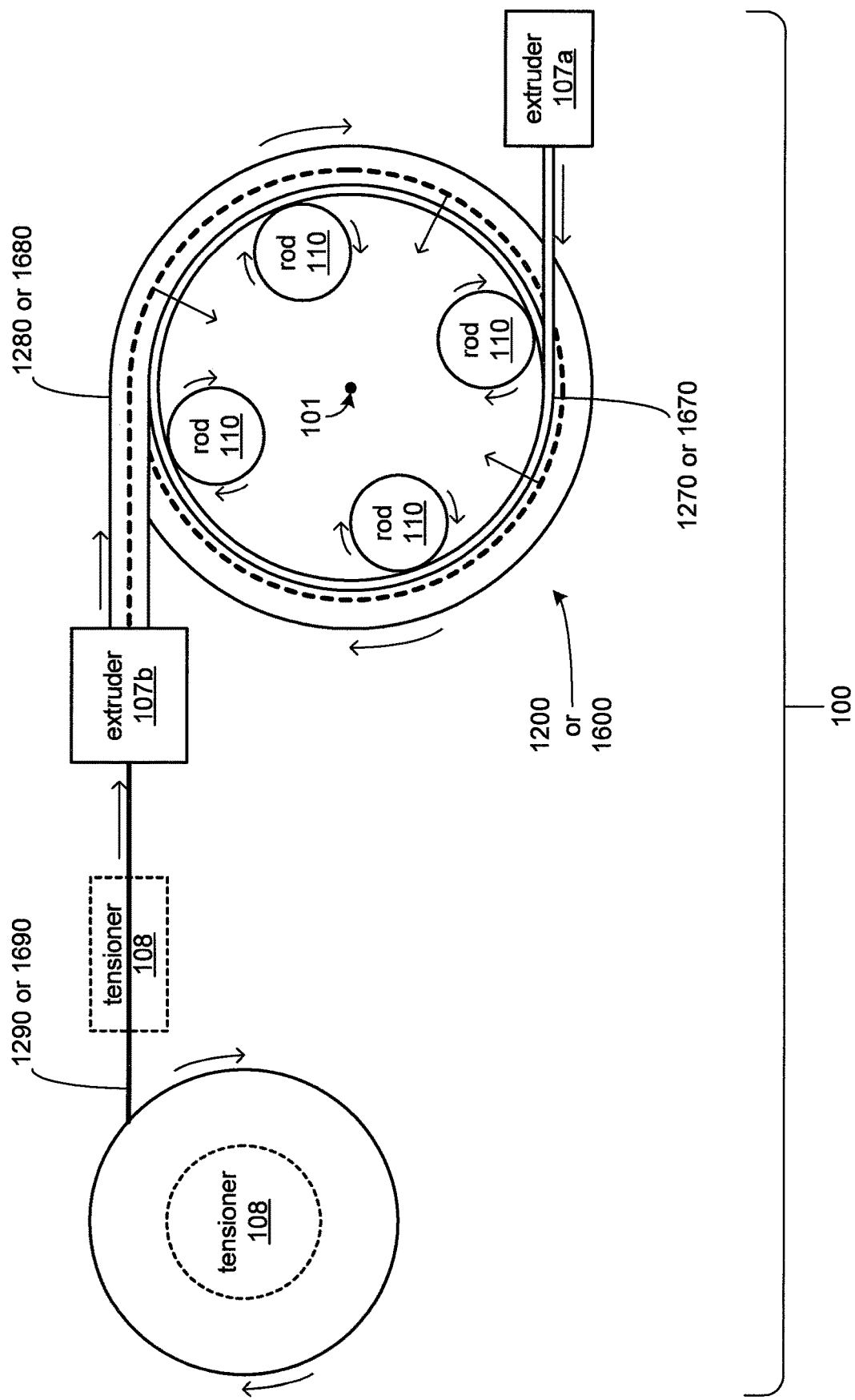
FIG. 4D is a block diagram of components of a hose making apparatus that has been adapted to make the hose of FIG. 4A.

As depicted most clearly in FIGS. 4C and 4D, each of the hoses 1200 and 1600 may be formed using a modified variant of a typical hose manufacturing apparatus 100. As will be familiar to those skilled in the art, such a hose manufacturing apparatus 100 may incorporate a set of rotating rollers 110 that may be canted in adjustable orientations relative to each other and relative to the axis 100 to form a hose therearound from one or more spirally wound extruded lengths of plastics material. As will also be familiar to those skilled in the art, such hose forming typically entails wrapping at least one extruded length of webbing material for the wall of the hose and at least one extruded length of a support bead for at least one support helix of the hose. Alternatively, a single extrusion of material that combines the webbing and support bead may be used, as will also be familiar to those skilled in the art. An example of such hose manufacturing apparatus is disclosed in U.S. Pat. No. 9,505,164 issued Nov. 29, 2016 to Carl J. Garrett, which is incorporated herein by reference in its entirety, and from which FIG. 1 was copied to provide 4C of this present application. Additional aspects of hose making on which the making of the hoses 1200 or 1600 may also be based are disclosed in U.S. Pat. No. 9,308,698 issued Apr. 12, 2016 to Martin E. Forrester, and U.S. Pat. No. 9,556,878 issued Jan. 31, 2017 to Carl J. Garrett, each of which is incorporated herein by reference in their entireties. However, to enable the forming of the hoses 1200 and 1600, such a typical hose making apparatus 100 may be modified to enable the extrusion of the flexible plastics material of the support helixes 1280 and 1680 around the heating wires 1290 and 1690, respectively, prior to the winding of the support helixes 1280 and 1680 onto the rollers 110.

As depicted most clearly in FIGS. 4D and 4F, as part of such modifications to the hose making apparatus 100, each of the heating wires 1290 and/or 1690 around which the plastic material of the helixes 1280 and/or 1680, respectively, is extruded may be tensioned (either at the spool from which each of the heating wires 1290 and/or 1690 are unwound, or with a separate tensioning device between the spool and the extruder 107b) to cause a "drawing down" of each of the heating wires 1290 and/or 1690 through the material of the support helixes 1280 and/or 1680, and closer towards the wall 1270 and/or 1670 as the hoses 1200 and/or 1600, respectively, are made. Stated differently, when the flexible material of each of the support helixes 1280 or 1680 is extruded around the heating wires 1290 or 1690 that are to be embedded therein, the heating wires 1290 or 1690 may initially centered within the extruded plastics material. However, as the freshly extruded (and still somewhat molten and compliant) plastics material of the support helix 1280 or 1680 is wound about a set of rotating rods 110 of hose making apparatus 100, the tensioner(s) 108 may exert tension on the heating wires 1290 or 1690 to cause the heating wires 1290 or 1690 to be pulled radially inwardly toward the central axis 101 of the hose 1200 or 1600 being formed. This may cause the heating wires 1290 or 1690 to migrate within the flexible plastics material of the support helix 1280 or 1680 (again, while still somewhat molten and compliant) to a position within that plastics material that is closer to the interior of the hose 1200 or 1600, respectively, being formed than their initially centered position.

Turning more specifically to FIG. 4E, as the wall 1270 or 1670 of one of the hoses 1200 or 1600 is formed on the rollers 110 of the hose making apparatus 100, a portion of the support helix 1280 or 1680 is laid down upon the external surface of the wall 1270 or 1670, respectively. As depicted, the cross-section of the length of extruded material from which the wall 1270 or 1670 is formed may include a pair of radially outwardly projecting guides to aid in guiding the support helix 1280 or 1680 into its proper position on the exterior surface of the wall 1270 or 1670, respectively. Turning more specifically to FIG. 4F, and regardless of whether such guide projections are provided, following the laying down of the portion of the support helix 1280 or 1680 onto the external surface of the wall 1270 or 1670, the aforedescribed tension causes inward migration of the heating wires 1290 or 1690 within the flexible (and still somewhat molten and compliant) plastics material of that portion of the support helix 1280 or 1680 toward the external surface of the wall 1270 or 1670 (which may be less molten or no longer molten, which may be used to stop the migration at the external surface of the wall 1270 or 1670), toward the interior of the hose 1200 or 1600, and toward the central axis 101 of the hose 1200 or 1600, respectively.

This technique of causing a radially inward draw down may be deemed preferable to attempting to position the heating wires 1290 and/or 1690 within the cross-sections of the extrusions of the helixes 1280 and/or 1680 at such locations during extrusion. This technique of causing a radially inward draw down may also provide the flexibility to allow variations in placement of the heating wires 1290 and/or 1690 further radially inward and/or further radially outward within the cross-sections of the helixes 1280 and/or 1680, respectively, as part of creating different variants of the hoses 1200 and/or 1600 that may have different heating characteristics (and/or other characteristics that may be influenced by placement of the heating wires 1290 and/or 1690 within the helixes 1280 and/or 1680, respectively).

FIGS. 5A through 5E, taken together, depict various aspects of coupling the expiratory inlet fitting 1500 to an undermold coupling 1800, and thereby, to one end of the expiratory hose 1600. Stated differently, and as earlier depicted in the exploded perspective views in each of FIGS. 1D, 1E and 3A, the expiratory inlet fitting 1500 may be coupled to one end of the expiratory hose 1600 via the depicted undermold coupling 1800 interposed between a portion of the outer surface of that end of the expiratory hose 1600 and a portion of the inner surface of a hose interface 1580 of the expiratory inlet fitting 1500.

The undermold coupling 1800 may include a tubular portion 1881 having a cylindrical tubular shape that defines a passage therethrough. At one end of the tubular shape of the tubular portion 1881 may be a ring 1883 that extends radially outward from the cylindrical tubular shape of the tubular portion 1881. Extending from the ring 1883 (or form another portion of the external surface of the tubular portion 1881) may be one or more gratings 1885 that may be defined by one or more parallel elongate portions of the flexible plastics material of the undermold coupling 1800 that define one or more parallel slots 1886. Each of the elongate portions of the material that define one of the one or more gratings 1885 may be curved to allow each to extend in a manner that follows the curve of the cylindrical shape of the tubular portion 1881.

Each grating 1885 may be supported by, and attached to, the rest of the structure of the undermold coupling 1800 (e.g., connected to the ring portion 1883, as depicted) by a pair of grating supports 1884 that may cooperate with the grating 1885 to create what may visually resemble a ladder. The grating supports may tend to support the one or more gratings 1885 at a location and in an orientation that causes each grating 1885 to extend alongside and in parallel with a portion of the external surface of the tubular portion 1881. While each grating 1885 is so positioned by one or more of the grating supports 1884, inwardly facing surfaces 1888 of each of the one or more curved elongate portions of flexible plastics material that defines each of the gratings 1885 may tend to be positioned in contact with the portion of the external surface of the tubular portion 1881 that its corresponding grating 1885 overlies. Being formed of the flexible plastics material of the undermold coupling 1800, the grating supports 1884 may each be flexible enough to allow each of the gratings 1885 to be pulled away from its position extending alongside and parallel with a portion of the external surface of the tubular portion 1881 (thereby pulling the inwardly facing surfaces thereof out of contact with the external surface of the tubular portion 1881.

The hose interface of the expiratory inlet fitting 1500 may incorporate one or more gratings 1586 that are meant to correspond to the one or more gratings 1885 carried by the undermold coupling 1800. Each of the one or more gratings 1586 may be defined by one or more parallel elongate portions of the rigid plastics material of the expiratory inlet fitting 1500 that define one or more parallel slots 1585 that may have the appearance of a set of one or more vent slots formed through the wall of the expiratory inlet fitting 1500. Each of the elongate portions of the material that define one of the one or more gratings 1586 may be curved to allow each to extend in a manner that parallels the curve of the cylindrical shape of the tubular portion 1881. Additionally, the one or more parallel elongate portions of the material of the expiratory fitting 1500 that define one of the one or more gratings 1586, and the one or more slots 1585 defined thereby, may be intersected by one or more troughs 1584 formed in the cylindrical external surface of the expiratory inlet fitting 1500 to receive a corresponding one or more of the grating supports 1884.

As depicted most clearly in FIGS. 5A, 5B, 5D and 5E, the undermold coupling 1800 may include threads 1882 formed on the inner surface of the tubular portion 1881 to receive and surround the external surface of one end of the expiratory hose 1600 in a manner that engages the wall 1670 and the support helix 1680 thereof as if the wall 1670 and helix 1680, together, formed matching threads as a mechanism by which the undermold coupling 1800 may grip that end of expiratory hose 1600 within the tubular portion 1881. In some embodiments, the tubular portion 1881 of the undermold coupling 1800 may be threaded onto an end of the expiratory hose 1600.

Figure 5A:
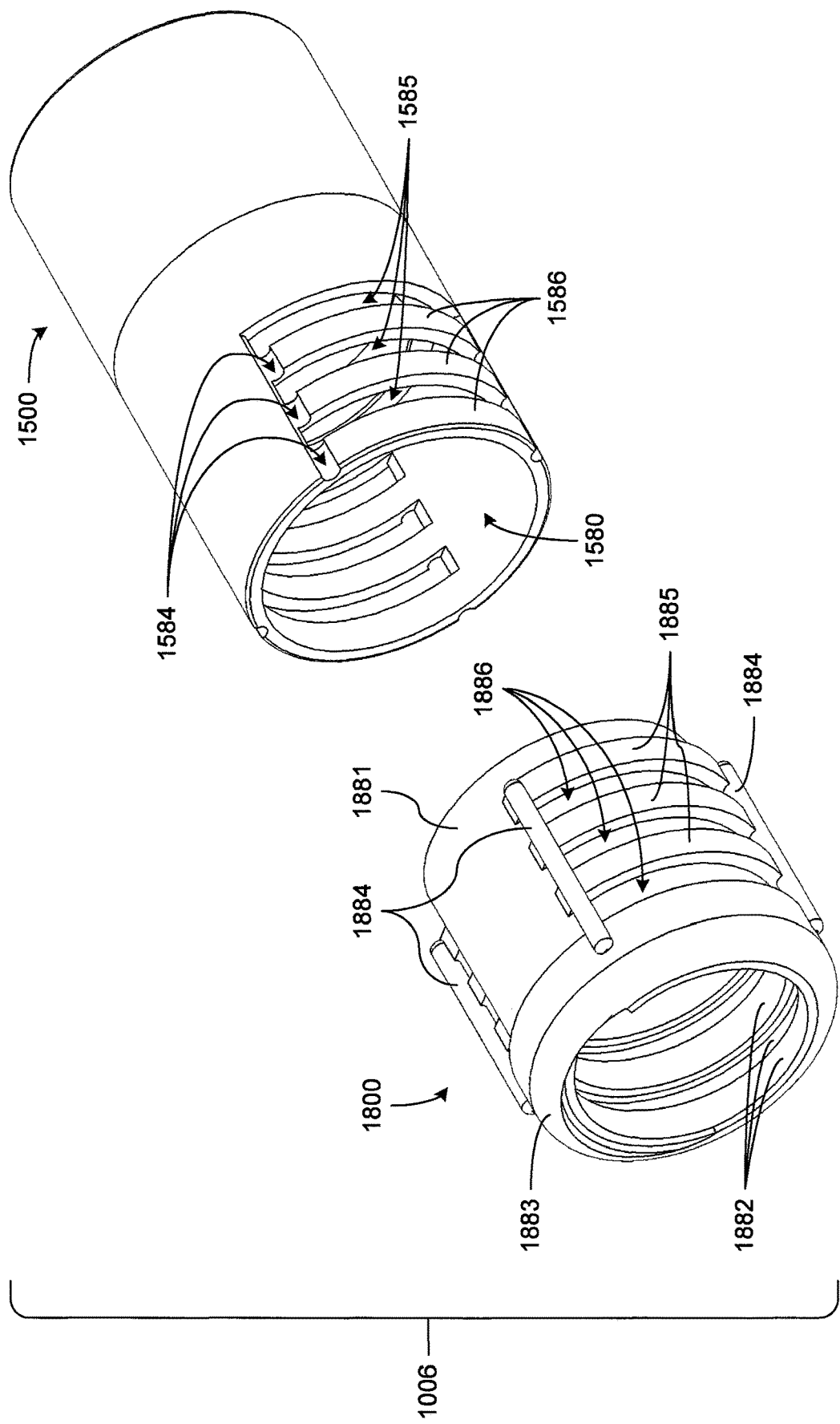
FIG. 5A is a perspective view a hose fitting and corresponding undermold coupling of any of the embodiments of heated respiratory hose assembly of any of FIG. 1A, 3A, 3B or 3C showing details of the features of one of the hose fittings and corresponding undermold coupling that are used to couple each to the other, and that are used to couple the undermold coupling to an end of one of the hoses.
Figure 5B:
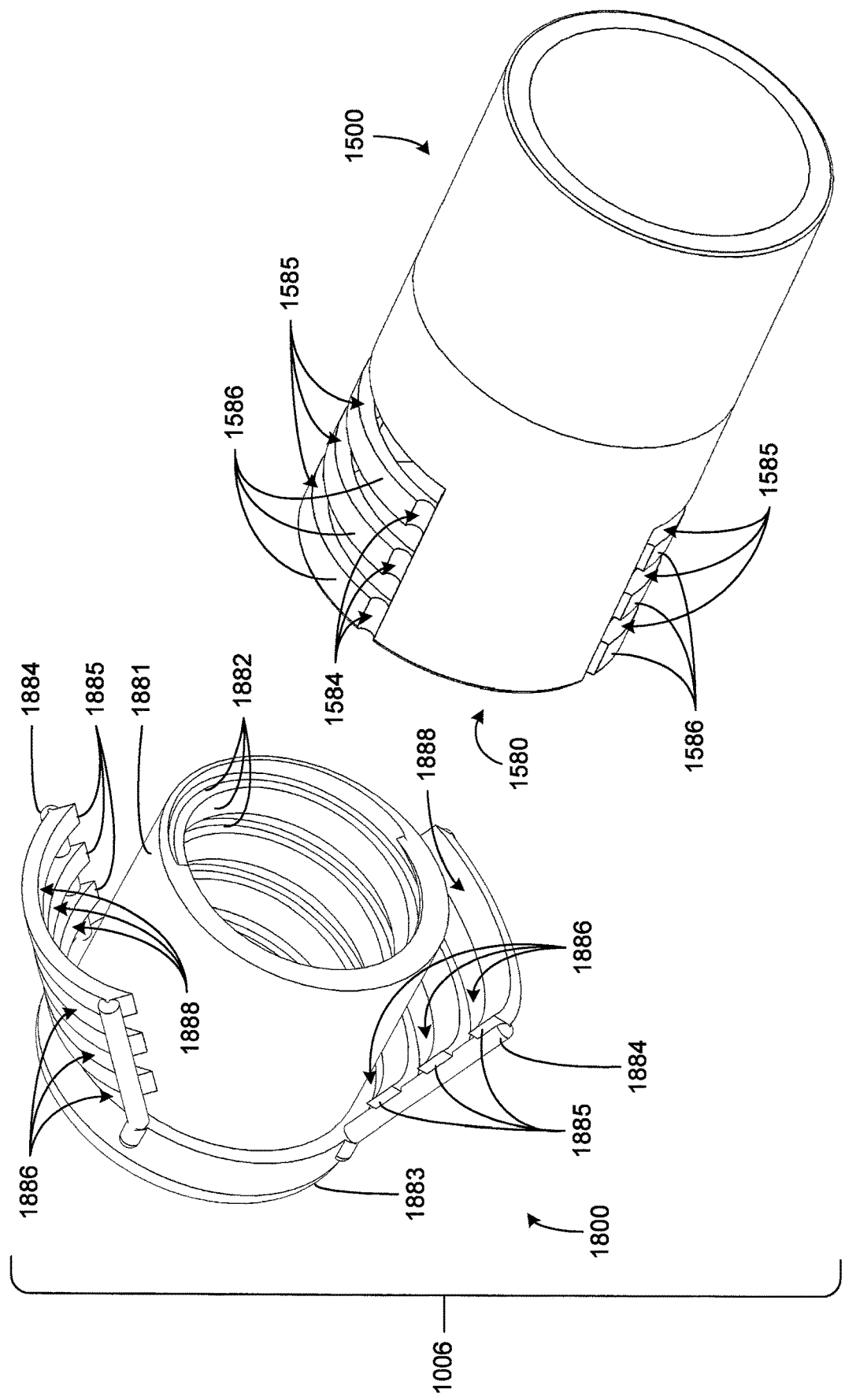
FIG. 5B is another perspective view of the hose fitting and corresponding undermold coupling of FIG. 5A showing details of the manner in which features of each are used to coupled each to the other.
Figure 5C:
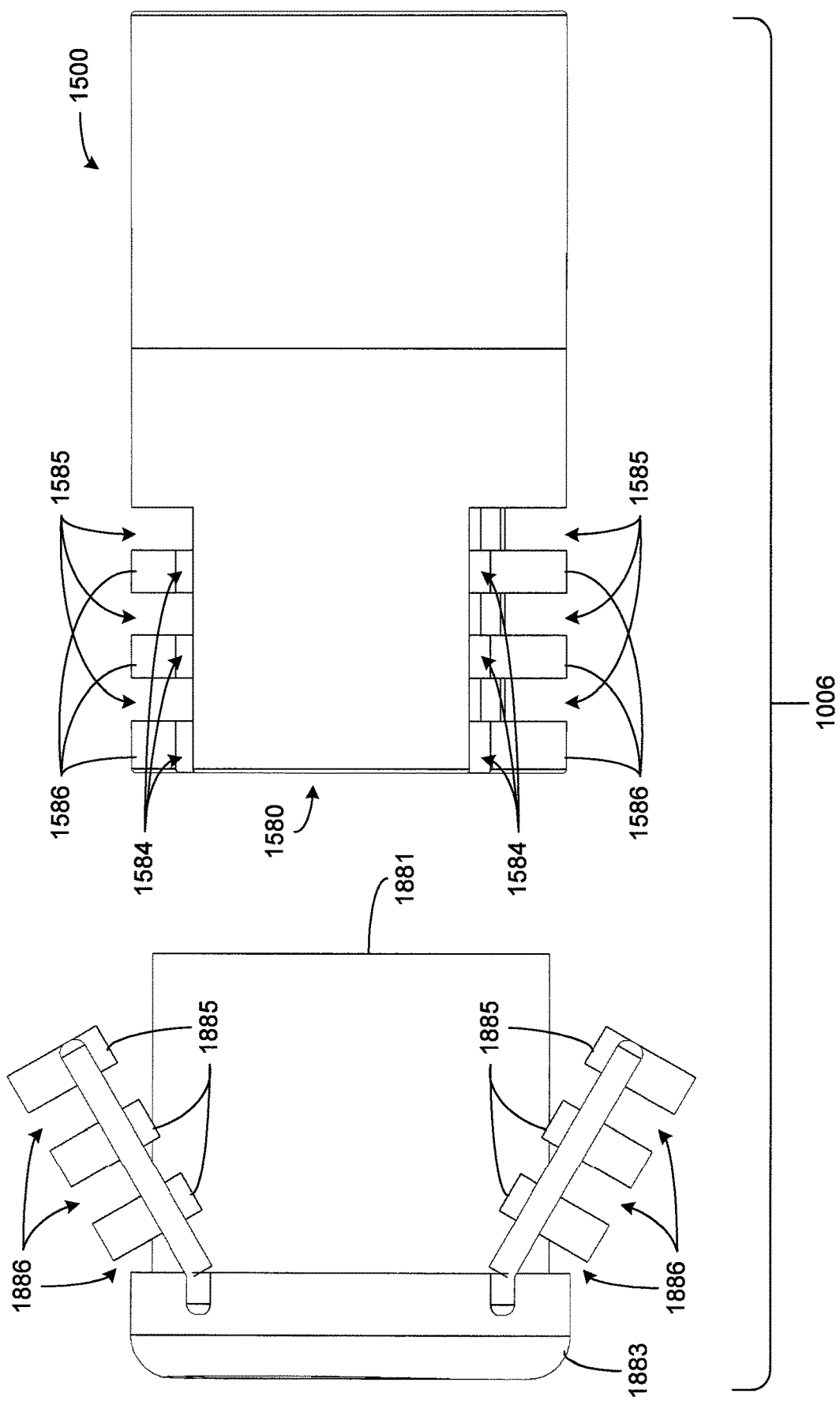
FIG. 5C is an elevational view of the hose fitting and corresponding undermold coupling of FIG. 5A prior to the coupling of each to the other.

Turning more specifically to FIGS. 5B and 5C, with the undermold coupling 1800 so threaded onto an end of the expiratory hose 1600, that end of the expiratory hose 1600 may be inserted into the hose interface 1580 of the expiratory inlet fitting 1500. As a result, the tubular portion 1881 of undermold coupling 1800 is inserted into the hose interface 1580 and becomes interposed between the external surface of that end of the expiratory hose 1600 and the internal surface of the hose interface 1580 of the expiratory inlet fitting 1500. As depicted in most clearly in FIGS. 5B and 5C, as such insertion occurs, each grating 1885 of the undermold coupling 1800 may be pulled away from the tubular portion 1881 (relying on the flexibility of the grating supports 1884 to act somewhat like hinges) and caused to extend over exterior portions of the expiration inlet fitting 1500 in the vicinity of the hose interface 1580. With each grating 1885 so positioned over its corresponding grating 1586, the grating 1885 may then be allowed to return to a position alongside and parallel to the external surface of the tubular portion 1881 of the undermold coupling 1800.

Figure 5D:
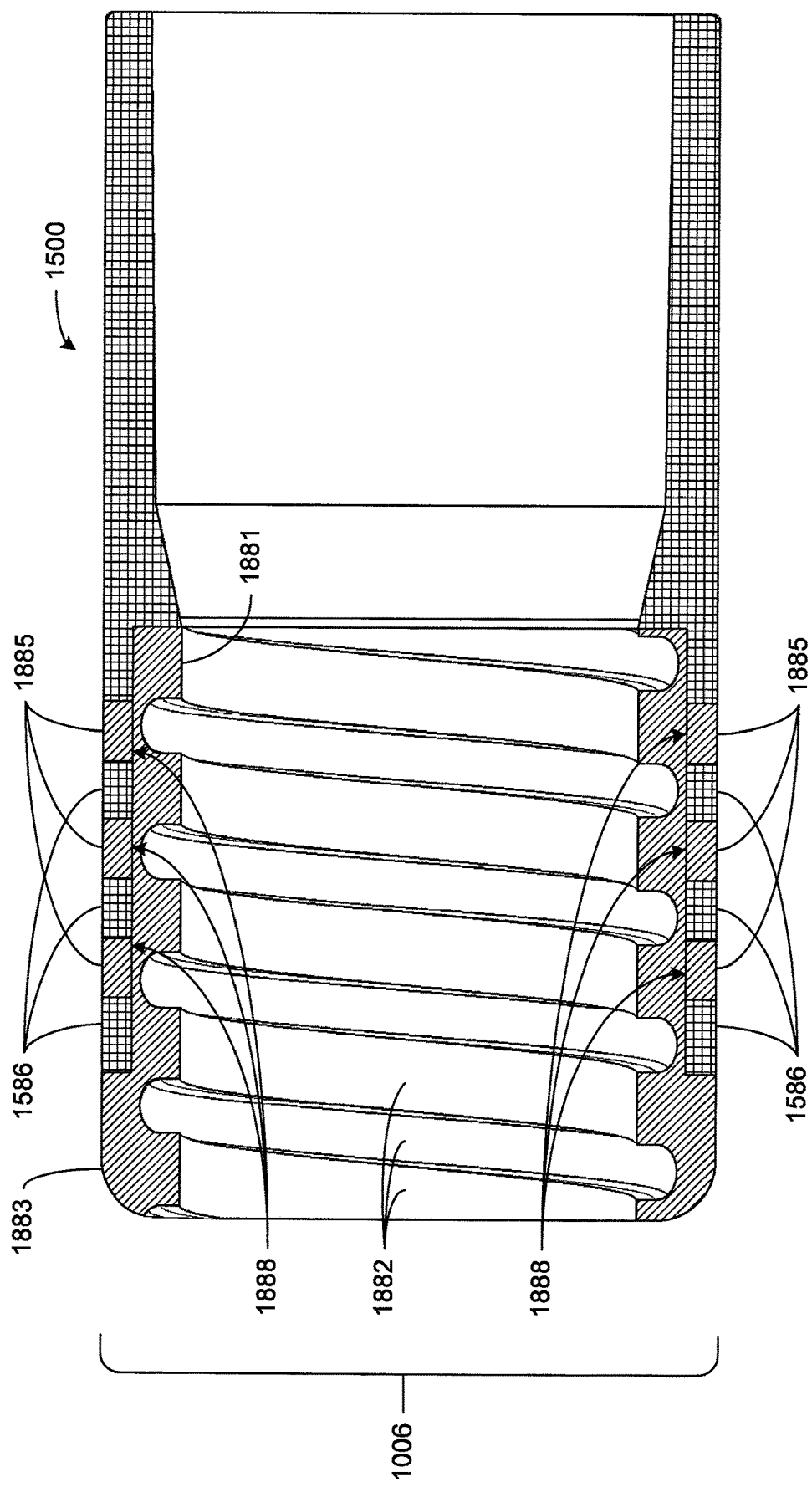
FIG. 5D is a cross-sectional view of the hose fitting and corresponding undermold coupling of FIG. 5A during the coupling of one to the other.
Figure 5E:
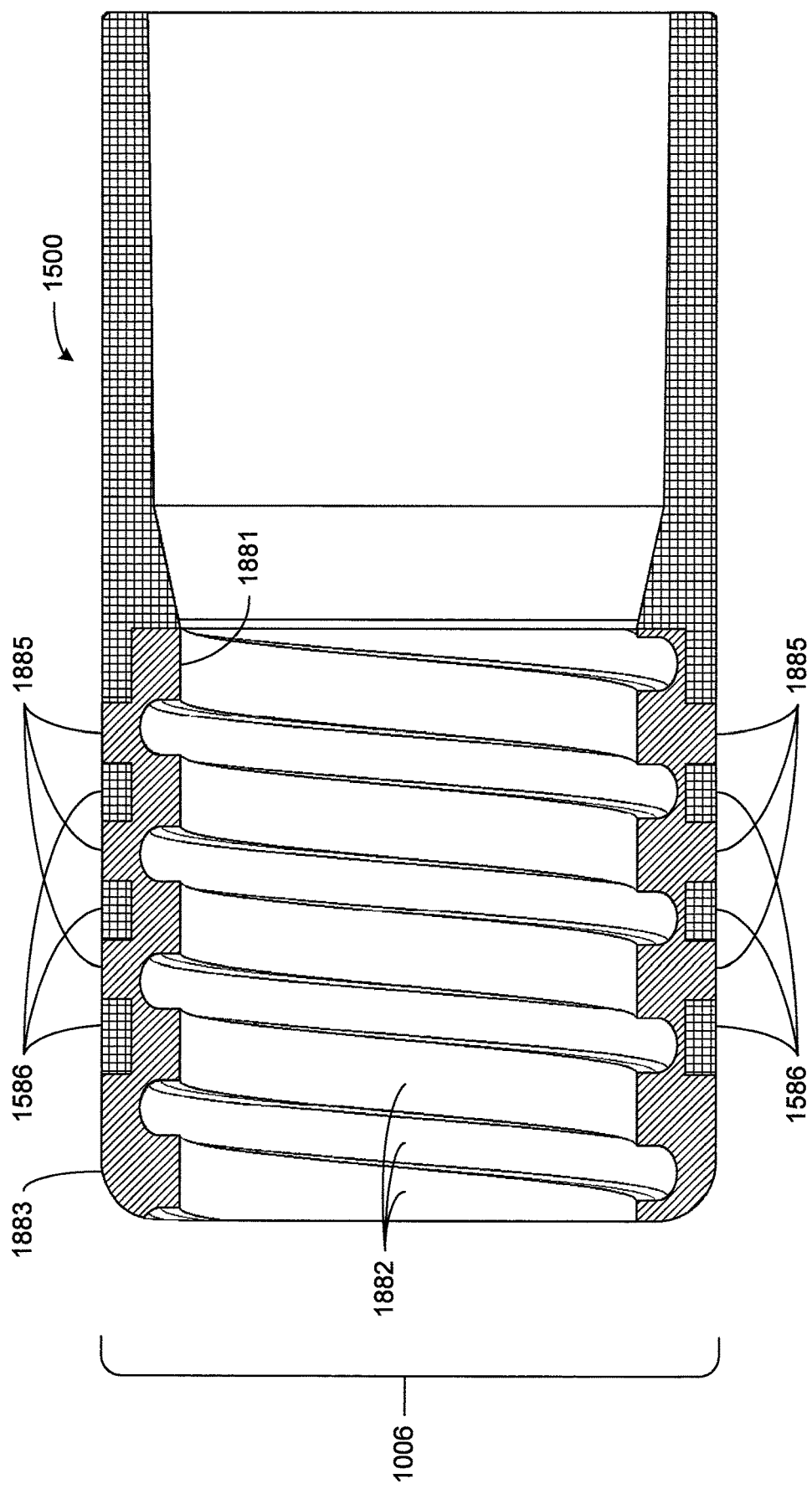
FIG. 5E is another cross-sectional view, similar to FIG. 5D, of the hose fitting and corresponding undermold coupling of FIG. 5A during the coupling of one to the other.

As depicted most clearly in FIG. 5D, with the each of the gratings 1885 allowed to return to a position alongside and parallel to the external surface of the tubular portion 1881 while each of the gratings 1885 is positioned over its corresponding grating 1586, the corresponding ones of the one or more gratings 1885 and 1586 are caused to intermesh in a manner that mechanically locks the undermold coupling 1800 within the hose interface 1580. More specifically, in each such interlock between a corresponding pair of gratings 1885 and 1586, each of the elongate portions of a grating 1885 of the undermold coupling 1800 extends into a corresponding slot 1585 defined by the corresponding grating 1586 of the expiratory inlet fitting 1500, and each of the elongate portions of that corresponding grating 1586 extends into a corresponding slot 1886 defined by the grating 1885.

As a result, the inwardly facing surfaces 1888 of each of the one or more curved elongate portions of the flexible plastics material of the undermold coupling that define each of the gratings 1885 is allowed to be brought back into contact with a portion of the external surface of the tubular portion 1881, as most clearly depicted in FIG. 5D. With such surface contacts once again made, while the one or more corresponding pairs of the gratings 1885 and 1586 are so intermeshed, heat may be applied to soften at least the undermold coupling 1800 to cause the inwardly facing surfaces 1888 of those portions of the one or more gratings 1885 that are once again in contact with the external surface of the tubular portion 1881 to become bonded to the exterior of the tubular portion 1881, as most clearly depicted in FIG. 5E. Such heating may also more broadly bond the materials of the thread-like exterior of the end of the expiratory hose 1600 (onto which the undermold coupling 1800 is threaded) to surfaces of the threads 1882 formed within the undermold coupling 1800, and such heating may also more broadly bond the material of the exterior surface of the tubular portion 1881 of the undermold coupling 1800 to the interior surface of the expiration inlet fitting 1500 into which the undermold coupling 1800 is inserted. As a result, gas-tight seals may be formed among these components.

In other embodiments, an end of the expiratory hose 1600 may be inserted into the hose interface 1580 of the expiratory inlet fitting 1500 without an undermold coupling 1800 threaded thereon. After such insertion, the flexible material of the undermold coupling 1800, in molten form, may be injected into one or more of the slots 1585 of one or more gratings 1586 of the hose interface 1580 to fill the space between the thread-like external surface of that end of the expiratory hose 1600 and the interior surface of the hose interface 1580 to form the undermold coupling 1800 in place therebetween, as well as to fill each of the slots 1585. Alternatively, the flexible material of the undermold coupling 1800, in molten form, may be injected therein between the expiratory hose 1600 and the edge of the interior surface of the hose interface 1580, where the expiratory hose 1600 enters into the hose interface 1580, to form the undermold coupling 1800 in place, as well as to fill each of the slots 1585 from within the interior of the hose interface 1580. Regardless of the exact manner in which the molten form of the material of the undermold coupling 1800 is injected to form the undermold coupling 1800 in place, in so forming the undermold coupling 1800 in place, the molten form of the undermold coupling 1800 may bond to the materials of thread-like external surface at the end of the expiratory hose 1600 and the interior surface of the hose interface 1580 to form a gas-tight seal therebetween.

It should be noted that although FIGS. 5A through 5E depict these features in a manner that is focused on the connection of an end of the expiratory hose 1600 to the expiratory inlet fitting 1500, the very same coupling arrangement just described may be employed to couple the other end of the expiratory hose 1600 to the expiratory outlet fitting 1700, and/or one or both ends of the inspiratory hose 1200 to one or both of the inspiratory inlet fitting 1100 and the inspiratory outlet fitting 1300. Stated differently, and as depicted most clearly in each of FIGS. 1D, 1E and 3A, multiple ones of the undermold coupling 1800 may be employed to couple each of the fittings 1100 and 1300 to opposite ends of the inspiratory hose 1200, and to couple each of the fittings 1500 and 1700 to opposite ends of the expiratory hose 1600.

FIGS. 6A through 6G, taken together, depict various aspects of incorporating the plug 1180 or 1780 incorporating the electrical connector 1190 or 1790 into one of the three connections provided by the inspiratory inlet fitting 1100 or the expiratory outlet fitting 1700, respectively. Also depicted are various aspects of the direct electrical coupling of the heating wires 1290 or 1690 to the electrical connector 1190 or 1790, respectively.

Figure 6A:
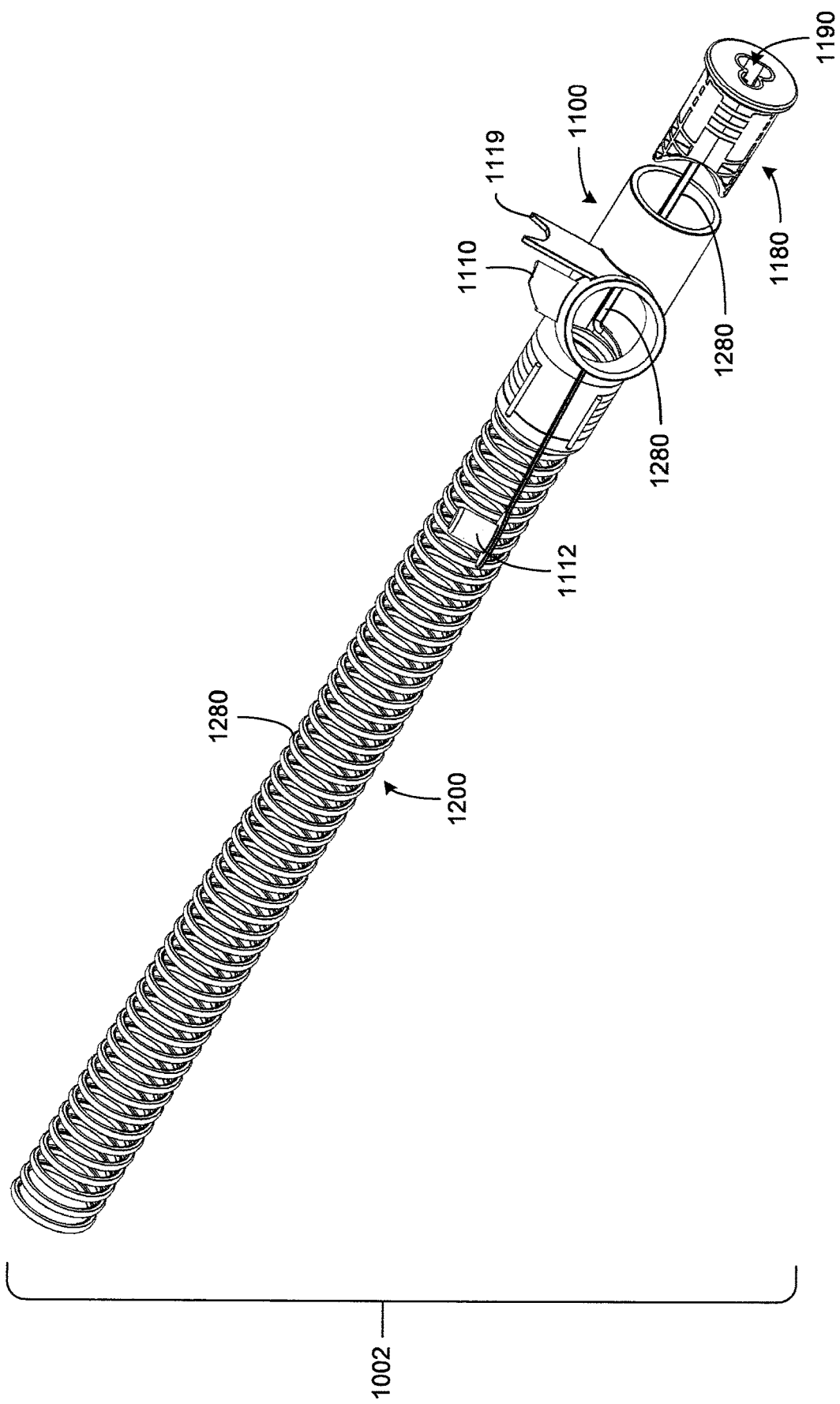
FIG. 6A is a partial perspective view of the inspiratory hose assembly of the heated respiratory hose assembly of FIG. 1A showing details of the electrical connection of an unwound end of the support helix of the hose thereof to an electrical connector carried within a plug within a hose fitting thereof.
Figure 6B:
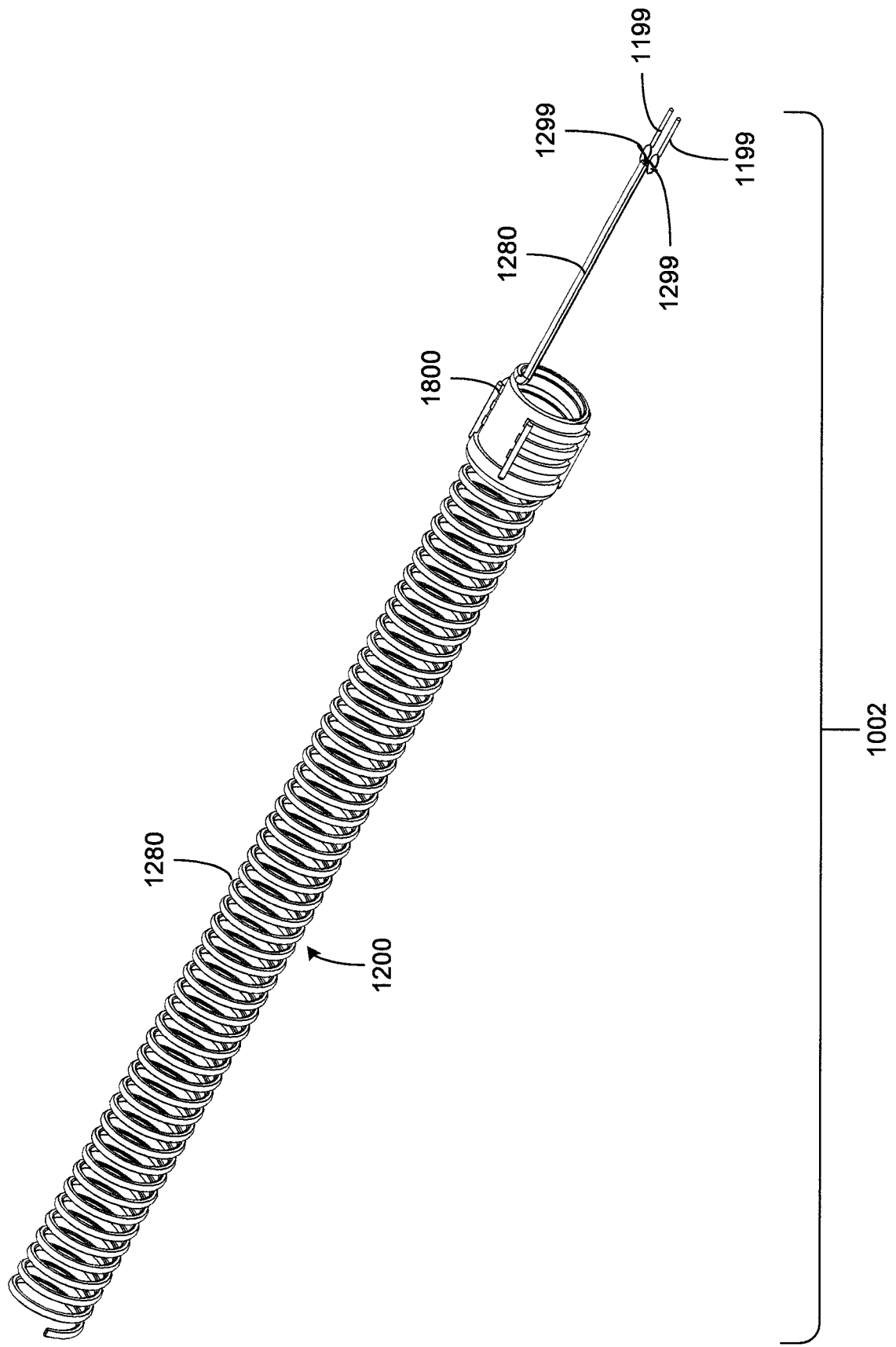
FIG. 6B is another partial perspective view of the inspiratory hose assembly of FIG. 6A showing further details of the electrical connection of the unwound end of the support helix to the electrical connector.

Each of FIGS. 6A and 6B depicts a subset of the components of the inspiratory hose assembly 1002 toward the end thereof that is to be connected to the medical device 990. More precisely, FIGS. 6A and 6B each depict the path followed by the support helix 1280 within the inspiratory hose 1200 and where an end of the inspiratory hose 1200 is coupled to the inspiratory inlet fitting 1100. The wall 1270 of the inspiratory hose 1200 has been omitted in both of these views for purposes of visual clarity. Additionally, in FIG. 6B, both the plug 1180 and the insulating shroud portion of the electrical connector 1190 have been omitted, also for purposes of visual clarity. As depicted, where an end of a portion of the inspiratory hose 1200 is inserted into a portion of the inspiratory inlet fitting 1100, a relatively short portion of the support helix 1280 is unwound from its helical path within the inspiratory hose 1200 and is employed as an electrical cable to bring the heating wires 1290 therein to the electrical connector 1190 within the plug 1180.

More specifically, a relatively short portion of the support helix 1280 is pulled out of the end of the inspiratory hose 1200 (i.e., unwound therefrom) where that end is inserted into the inspiratory inlet fitting 1100, and straightened to at least some degree for use as an electrical cable to bring the heating wires 1290 therein directly to the electrical connector 1190. This unwinding of the relatively short portion of the support helix 1280 may be performed prior to the threading of the depicted undermold coupling 1800 onto the end of the inspiratory hose 1200 that is to be inserted into the inspiratory inlet fitting 1100. As a result, the relatively short unwound portion of the support helix 1280 extends beyond the end of the inspiratory hose 1200 onto which the undermold coupling 1800 is threaded, thereby emerging from within the undermold coupling 1800 and extending further into the interior of the inspiratory inlet fitting 1100 than the end of the inspiratory hose 1200 onto which the undermold coupling 1800 is threaded.

The end of the relatively short portion of the support helix 1280 that extends toward the electrical connector 1190 may be partly stripped away to remove at least enough of the flexible plastics material of the support helix 1280 to expose enough of the heating wires 1290 therein to enable forming an electrical connection with the contacts 1199 of the electrical connector 1190. More precisely, the plastics material of the support helix 1280 may be stripped away in a manner that may be akin to procedures often used in preparing conventional multi-conductor cables for the connection of the individual wires therein to contacts of an electrical connector or other electrical device. Thus, typical wire stripping techniques may be employed to gain access to each of the heating wires 1290, and then the conductor 1299 (see FIG. 4B) within each of the heating wires 1290 may be soldered to a soldering tab of one of the electrical contacts 1199 of the electrical connector 1190. Additionally, if the relatively short unwound portion of the support helix 1280 is additionally covered in a sheath (e.g., heatshrink tubing that may be sleeved over the relatively short unwound portion of the support helix 1280), then part of that sheath may also be similarly stripped away using typical wire stripping techniques. As previously discussed, the conductor 1299 of each of the heating wires 1290 may be sheathed within an individual insulator 1291 that is selected to be thermally resistant to the temperatures expected to be encountered during heating of the inspiratory hose 1200, but not to the temperatures expected to be encountered during soldering, thereby eliminating the need to strip each of the conductors 1299 of their individual insulators 1291 prior to soldering each of the conductors 1299 to a soldering tab of one of the electrical contacts 1199.

In separating the relatively short portion of the support helix 1280 from the inspiratory hose 1200, portions of the wall 1270 (again, not shown for purposes of visual clarity) that extend between adjacent coils of the support helix 1280 that are included in the relatively short portion thereof may be trimmed away. After being so separated, the relatively short unwound portion of the support helix 1280 may be heated to soften the flexible plastics material thereof (i.e., to relax the molecules of the flexible plastics material thereof) to aid in straightening it out from its original helical path within the inspiratory hose 1200 (i.e., causing the molecules of the flexible plastics material of the relatively short portion of the support helix 1280 to adopt a straightened path as a new resting state).

The actual length of the relatively short portion of the support helix 1280 that emerges from the undermold coupling 1800 and extends further into the interior of the inspiration inlet fitting 1100 may be based, at least in part, on the dimensions of the inspiration inlet fitting 1100. More specifically, the length may be selected based on the length needed to extend from the undermold coupling 1800 and to the electrical connector 1190, and may include a predetermined additional length needed to allow manufacturing personnel sufficient physical access to solder the conductors 1299 of the heating wires 1290 to the soldering tabs of the electrical contacts 1199, as earlier described.

Figure 6C:
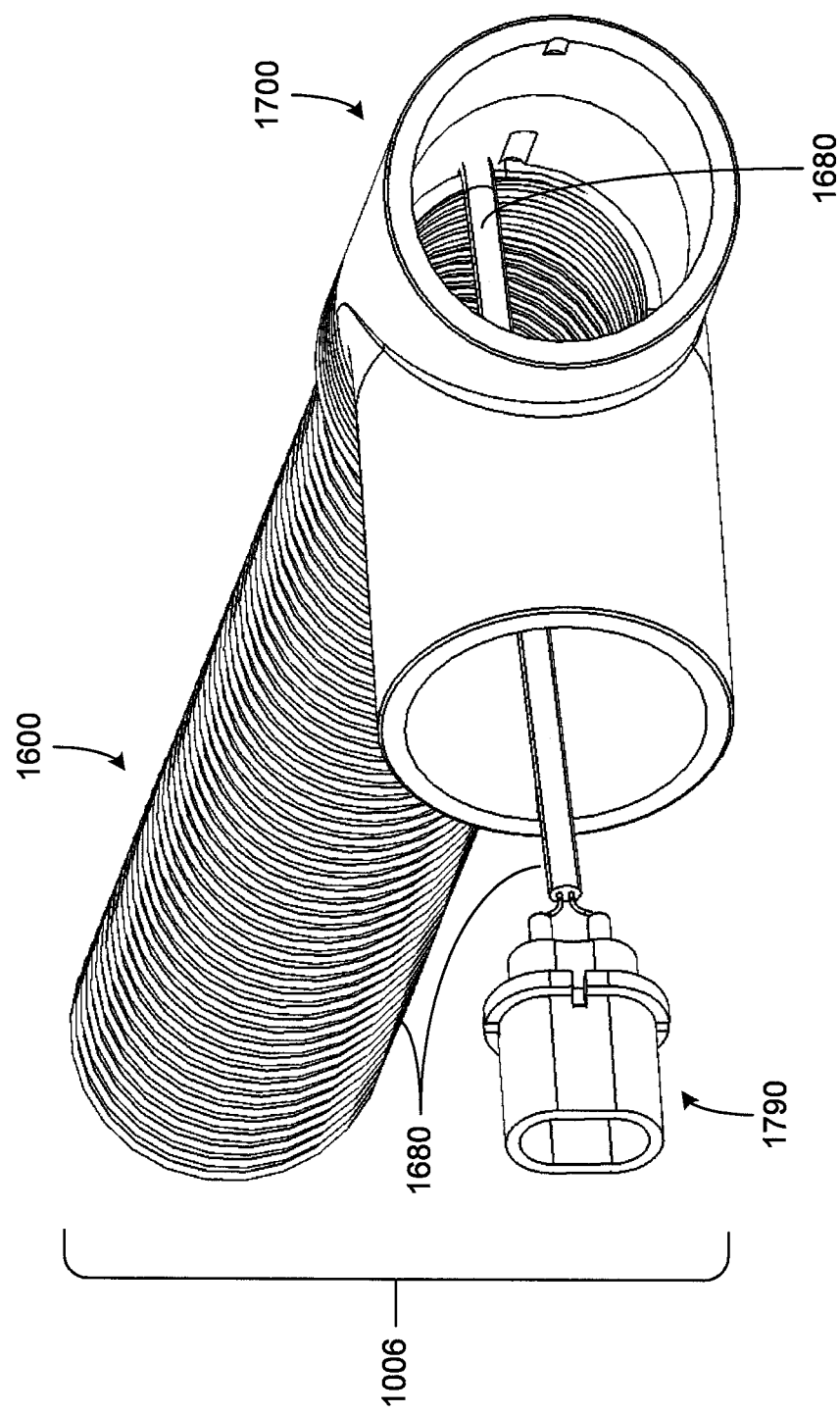
FIG. 6C is a partial perspective view of the expiratory hose assembly of the heated respiratory hose assembly of FIG. 1A showing details of the electrical connection of an unwound end of the support helix of the hose thereof to an electrical connector carried within a plug within a hose fitting thereof.

In a manner somewhat similar to FIGS. 6A and 6B, FIG. 6C depicts a subset of the components of the expiratory hose assembly 1006 toward the end thereof that is to be connected to the medical device 990. More precisely, FIG. 6C depicts the path followed by the support helix 1680 within the expiratory hose 1600 and where an end of the expiratory hose 1600 is coupled to the expiratory outlet fitting 1600. The wall 1670 of the expiratory hose 1600, the plug 1780 and the insulating shroud portion of the electrical connector 1790 have all been omitted for purposes of visual clarity. As depicted, where an end of a portion of the expiratory hose 1600 is inserted into a portion of the expiratory outlet fitting 1700, a relatively short portion of the support helix 1680 is unwound from its helical path within the expiratory hose 1600 and is employed as an electrical cable to bring the heating wires 1690 therein to the electrical connector 1790 within the plug 1780 (again, not shown).

More specifically, a relatively short portion of the support helix 1680 is pulled out of the end of the expiratory hose 1600 (i.e., unwound therefrom) where that end is inserted into the expiratory outlet fitting 1700, and straightened to at least some degree for use as an electrical cable to bring the heating wires 1690 therein directly to the electrical connector 1790. In a manner similar to what was discussed above concerning the support helix 1280, this unwinding of the relatively short portion of the support helix 1680 may be performed prior to the threading of another of the undermold couplings 1800 onto the end of the expiratory hose 1600 that is to be inserted into the expiratory outlet fitting 1700. As a result, the relatively short portion of the support helix 1680 extends beyond the end of the expiratory hose 1600 onto which the undermold coupling 1800 is threaded, thereby emerging from within the undermold coupling 1800 and extending further into the interior of the expiratory outlet fitting 1700 than the end of the expiratory hose 1600 onto which the undermold coupling 1800 is threaded.

As with the earlier discussed relatively short portion of the support helix 1280 employed as an electrical cable, the end of the relatively short unwound portion of the support helix 1680 that extends toward the electrical connector 1790 may also be partly stripped away to remove at least enough of the flexible plastics material of the support helix 1680 to expose enough of the heating wires 1690 therein to enable forming an electrical connection with the contacts 1199 of the electrical connector 1190. Again, this may also be done using typical wire stripping techniques, and again, if the stripped-away part of the unwound portion of the support helix 1680 is additionally covered in a sheath (e.g., heat-shrink tubing), part of that sheath may also be similarly stripped away using typical wire stripping techniques. Also again, in separating the relatively short portion of the support helix 1680 from the expiratory hose 1600, portions of the wall 1670 (again, not shown for purposes of visual clarity) that extend between adjacent coils of the support helix 1680 that are included in the relatively short portion thereof may be trimmed away. And again, after being so separated, the relatively short portion of the support helix 1680 may be heated to soften the flexible plastics material thereof to aid in straightening it out from its original helical path within the expiratory hose 1600.

As with the earlier discussed relatively short portion of the support helix 1280 employed as an electrical cable, the actual length of the relatively short portion of the support helix 1680 that emerges from the undermold coupling 1800 and extends further into the interior of the expiration outlet fitting 1700 may be based, at least in part, on the dimensions of the expiration outlet fitting 1700. More specifically, the length may be selected based on the length needed to extend from the undermold coupling 1800 and to the electrical connector 1790, and may include a predetermined additional length needed to allow manufacturing personnel sufficient physical access to solder the conductors 1699 of the heating wires 1690 to the soldering tabs of the electrical contacts 1799.

Such use of a portion of the support helixes 1280 and/or 1680, as if each were a conventional two-conductor electric cable, advantageously avoids the creation of electrical terminations where a transition is made between the heating wires 1290 and/or 1690 of the support helixes 1280 and/or 1680 to non-heating wires that travel a relatively short distance within the fittings 1100 and/or 1300 to electrically couple the heating wires 1290 and/or 1690 to the electrical connectors 1190 and/or 1790, respectively. Experience has shown that such electrical terminations to transition between heating and non-heating wires can be a source of potentially dangerous electrical failures. Poorly implemented electrical terminations of this type can actually have a higher resistance than the heating wires 1290, themselves, such that the terminations can become hotter than either the heating wires 1290 or 1690. This may lead to such hazards as burning through the plastics material of the inspiratory inlet fitting 1100 and/or otherwise generating toxic smokes/gases within the inspiratory inlet fitting 1100 that may be inhaled by the patient. It has been discovered through testing that such a transition between heating and non-heating wires is unnecessary, and that portions of the support helixes 1280 and 1680 can be used as multi-conductor cables, as has been described.

Figure 6D:
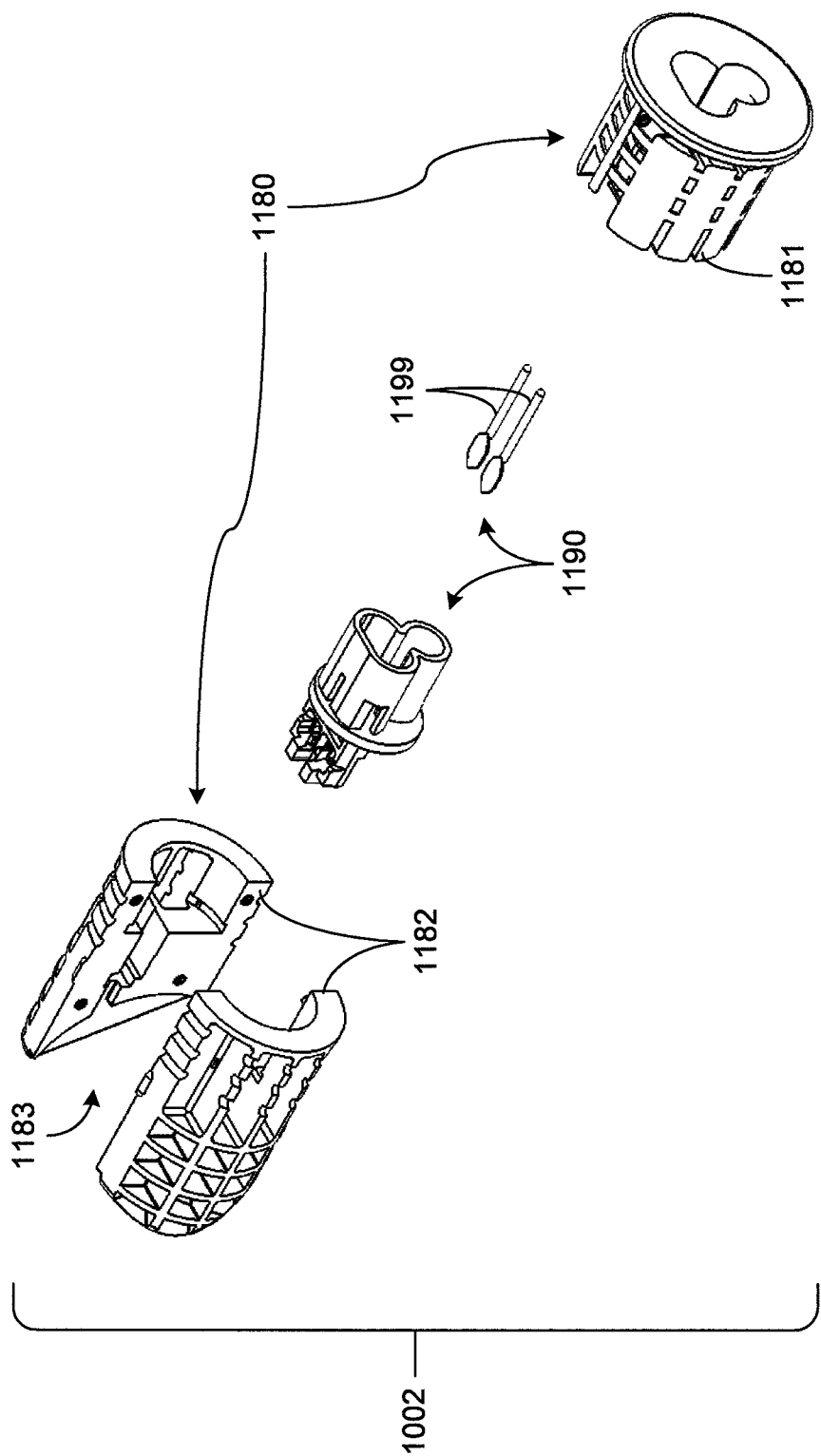
FIG. 6D is an exploded perspective view of the combination of the plug and electrical connector of the inspiratory hose assembly of FIGS. 6A and 6B showing details of the manner in which the plug may be assembled from multiple pieces around the electrical connector.
Figure 6E:
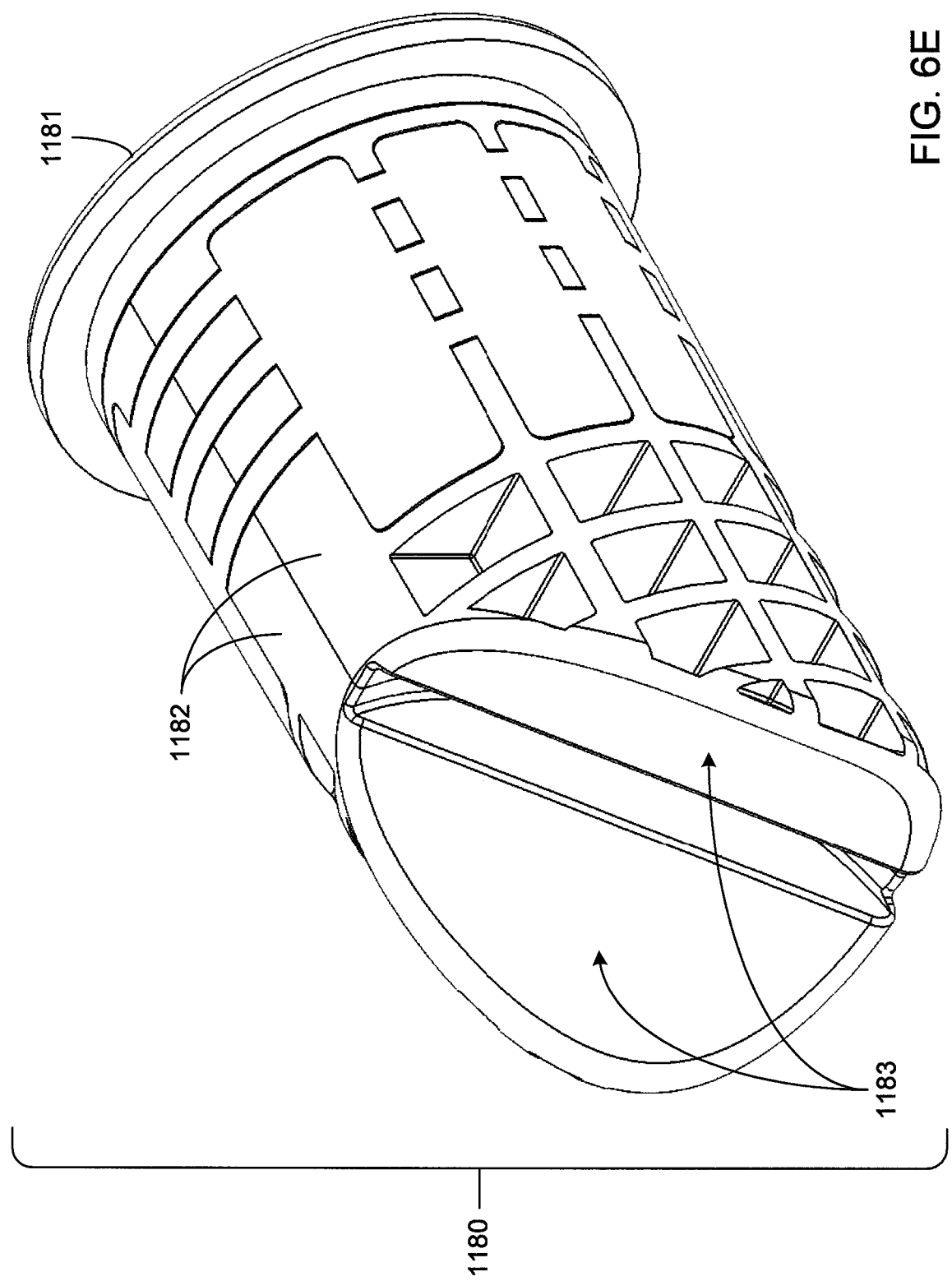
FIG. 6E is a perspective view of the plug of the inspiratory hose assembly of FIGS. 6A and 6B showing details of the shaping of the plug improve the flow of respiratory gases through the inspiratory hose assembly.

FIGS. 6D and 6E, taken together, depict various features of the plug 1180 and the electrical connector 1190 carried therein. As depicted, in some embodiments, the plug 1180 may be formed from multiple separately fabricated plastic components, including the depicted face portion 1181 and the depicted pair of "clamshell" portions 1182. In this depicted embodiment, much of the electrical connector 1190 (with its electrical contacts 1199 installed therein, and already soldered to the conductors 1299 of the heating wires 1290 of the support helix 1280) may be enclosed between the two clamshell portions 1182, which may be fastened to each other in any of a variety of ways. A portion of the support helix 1280 adjacent the electrical connector 1190 may also be enclosed between the two clamshell portions 1182. The face portion 1181 may then be molded over the assembled pair of the clamshell portions 1182 with the electrical connector 1190 enclosed between the clamshell portions 1182. In so molding the face portion 1181, portions of the plastics material of the face portion 1181, while in a molten state, may fill various convolutions formed within each of the two clamshell portions 1182 to further bond them together. In so doing, the face portion 1181 may also seal spaces between the two clamshell portions 1182 within which the electrical connector 1190 is held, as well as the portion of the support helix that is also enclosed therebetween. In so doing, the electrical connections between the conductors 1299 of the heating wires 1290 and the electrical contacts 1199 of the electrical connector 1190 may be entirely enclosed to seal and protect those connections against moisture present in the respiratory gases conveyed through the inspiratory inlet fitting 1100 to thereby prevent corrosion, etc.

Alternatively, in other embodiments, following the connection of the conductors 1299 of the heating wires 1290 of the support helix 1280 to the electrical contacts 1199 of the electrical connector 1190, the entire plug 1180 may simply be molded around the electrical connector 1190. A portion of the support helix 1280 adjacent the electrical connector 1190 may also be enclosed within such a molded form of the plug 1180.

Regardless of the exact manner in which the plug 1180 is formed and/or in which the electrical connector 1190 is caused to be enclosed within the plug 1180, the portion of the plug 1180 that extends furthest into the inspiration inlet fitting 1100 may be shaped to cooperate with interior surface portions of the inspiration inlet fitting 1100 to present a relatively unobstructed path for the flow of respiratory gases through the inspiration inlet fitting 1100 with relatively smooth surfaces encountered by the respiratory gases throughout that path. More precisely, and as best seen in FIG. 6E, as well as in FIGS. 1D, 1E and 6A, the portion of the plug 1180 that extends furthest into the inspiration inlet fitting 1100 may be provided with a concave surface 1183 that serves to define part of such a relatively unobstructed path with smooth surfaces for the flow of respiratory gases.

Figure 6F:
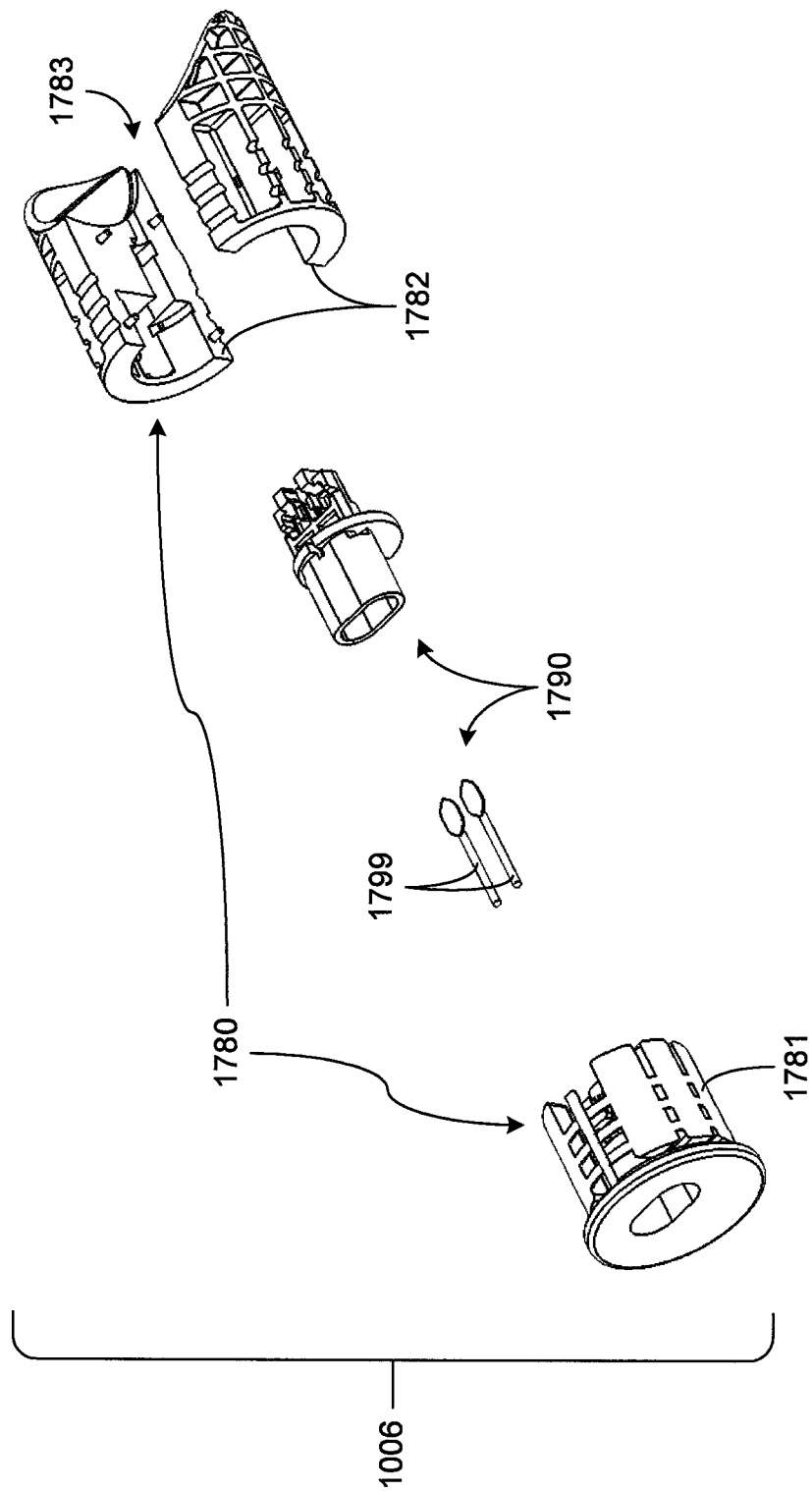
FIG. 6F is an exploded perspective view of the combination of the plug and electrical connector of the expiratory hose assembly of FIG. 6C showing details of the manner in which the plug may be assembled from multiple pieces around the electrical connector.
Figure 6G:
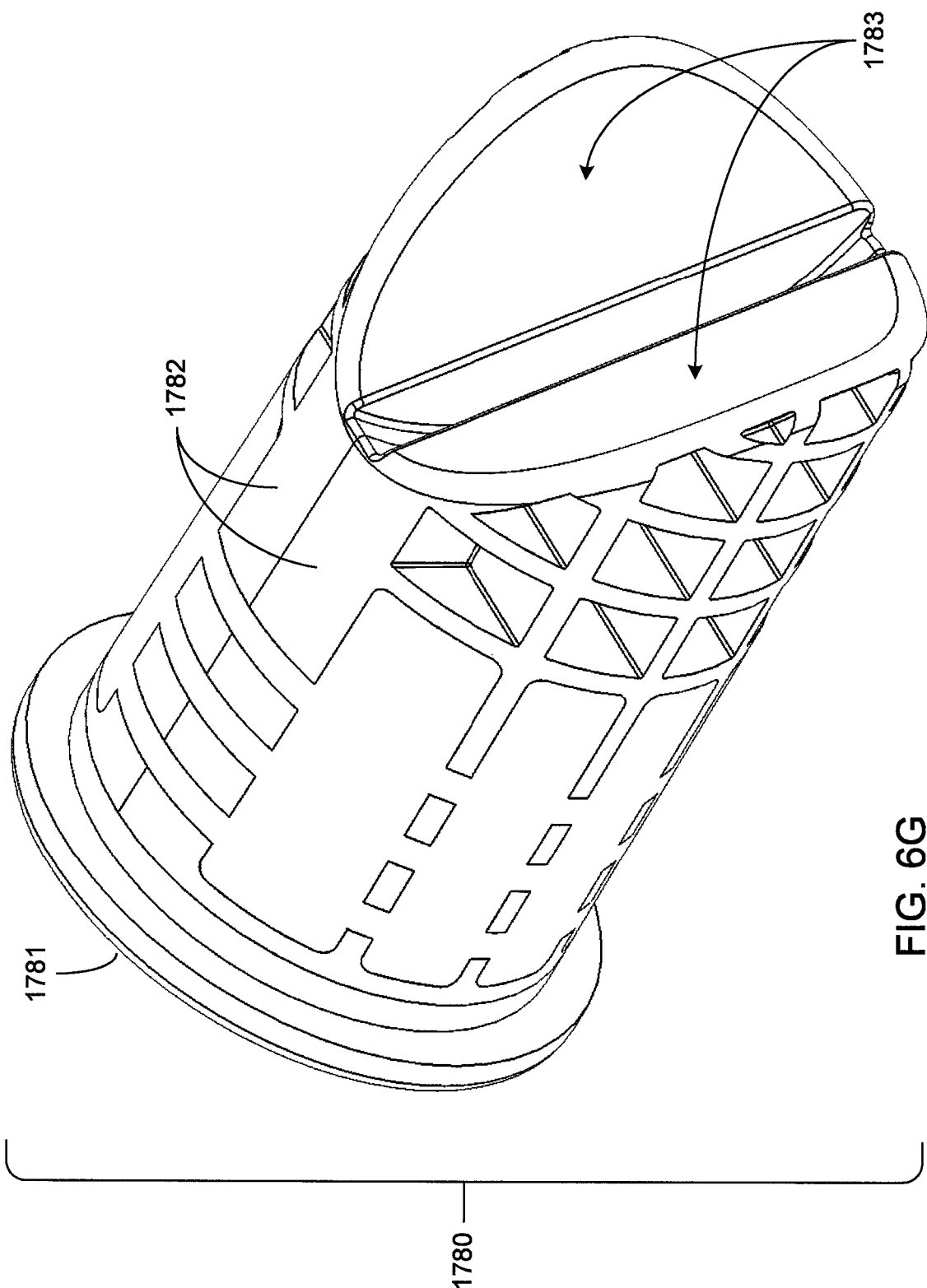
FIG. 6G is a perspective view of the plug of the expiratory hose assembly of FIG. 6C showing details of the shaping of the plug improve the flow of respiratory gases through the inspiratory hose assembly.

FIGS. 6F and 6G, taken together, depict similar features of the plug 1780 and the electrical connector 1790 carried therein. As depicted, in some embodiments, the plug 1780 may be formed from multiple separately fabricated plastic components, including the depicted face portion 1781 and the depicted pair of clamshell portions 1782. In this depicted embodiment, much of the electrical connector 1790 (with its electrical contacts 1799 installed therein, and already soldered to the conductors 1699 of the heating wires 1690 of the support helix 1680) may be enclosed between the two clamshell portions 1782, which may be fastened to each other in any of a variety of ways. A portion of the support helix 1680 adjacent the electrical connector 1790 may also be enclosed between the two clamshell portions 1782. The face portion 1781 may then be molded over the assembled pair of the claims clamshell portions 1782 to form the plug 1780 with the electrical connector 1790 sealed in place therein in a manner similar to what has been previously described in reference to the plug 1180.

Alternatively, in other embodiments, following the connection of the conductors 1699 of the heating wires 1690 of the support helix 1680 to the electrical contacts 1799 of the electrical connector 1790, the entire plug 1780 may simply be molded around the electrical connector 1790. A portion of the support helix 1680 adjacent the electrical connector 1790 may also be enclosed within such a molded form of the plug 1780.

As with the plug 1180, regardless of the exact manner in which the plug 1780 is formed and/or in which the electrical connector 1790 is caused to be enclosed within the plug 1780, the portion of the plug 1780 that extends furthest into the expiration outlet fitting 1700 may be shaped to cooperate with interior surface portions of the expiration outlet fitting 1700 to present a relatively unobstructed path for the flow of respiratory gases through the expiration outlet fitting 1700 with relatively smooth surfaces encountered by the respiratory gases throughout that path. More precisely, and as best seen in FIG. 6G, as well as in FIGS. 1D and 1E, the portion of the plug 1780 that extends furthest into the inspiration inlet fitting 1700 may be provided with a concave surface 1783 that serves to define part of such a relatively unobstructed path with smooth surfaces for the flow of respiratory gases.

It should be noted that, as depicted in FIGS. 6D and 6F, as well as throughout others of the figures in this present application, the electrical connectors 1190 and 1790 may be provided with differing physical shapes as a keying mechanism to prevent incorrect electrical connections between the medical device 990 and each of the heating wires 1290 and 1690 within the hoses 1200 and 1600, respectively. More specifically, the electrical connector 1190 is depicted as being a so-called "monkey face" connector having a shape that includes three lobes in which two of the lobes are each occupied by one of the electrical contacts 1199. In contrast, the electrical connector 1790 is depicted as having a more conventional elongate oval-like shape in which the electrical contacts 1799 are positioned toward opposite ends of the of the oval-like shape. As will be familiar to those skilled in the art of such medical devices as ventilators and CPAP devices, this depicted combination of forms of the electrical connectors 1190 and 1790 have become widely adopted for use in providing electric power for heating the hoses used with such medical devices.

As previously discussed, at the opposite end of the support helix 1280 from the end that is connected to the electrical connector 1190, the conductors 1299 of the pair of heating wires 1290 may be electrically connected to each other through crimping, soldering, etc., to form an electrical loop with the pair of heating wires 1290 through the support helix 1280 for heating the interior of the inspiration hose 1200. Similarly, at the opposite end of the support helix 1680 from the end that is connected to the electrical connector 1790, the conductors 1699 of the pair of heating wires 1690 may be similarly electrically connected to each other to form a separate electrical loop with the pair of heating wires 1690 through the support helix 1680 for separately heating the interior of the expiration hose 1600. As also previously discussed, the medical device 990 may operate each of these electrical loops separately and in different ways that may be selected to cause differing degrees of heating within each of the hoses 1200 and 1600. Indeed, as also previously discussed, the heating wires 1290 and 1690 may be selected to have different resistances in recognition of such differences in the manner in which each may be used.

Figure 7B:
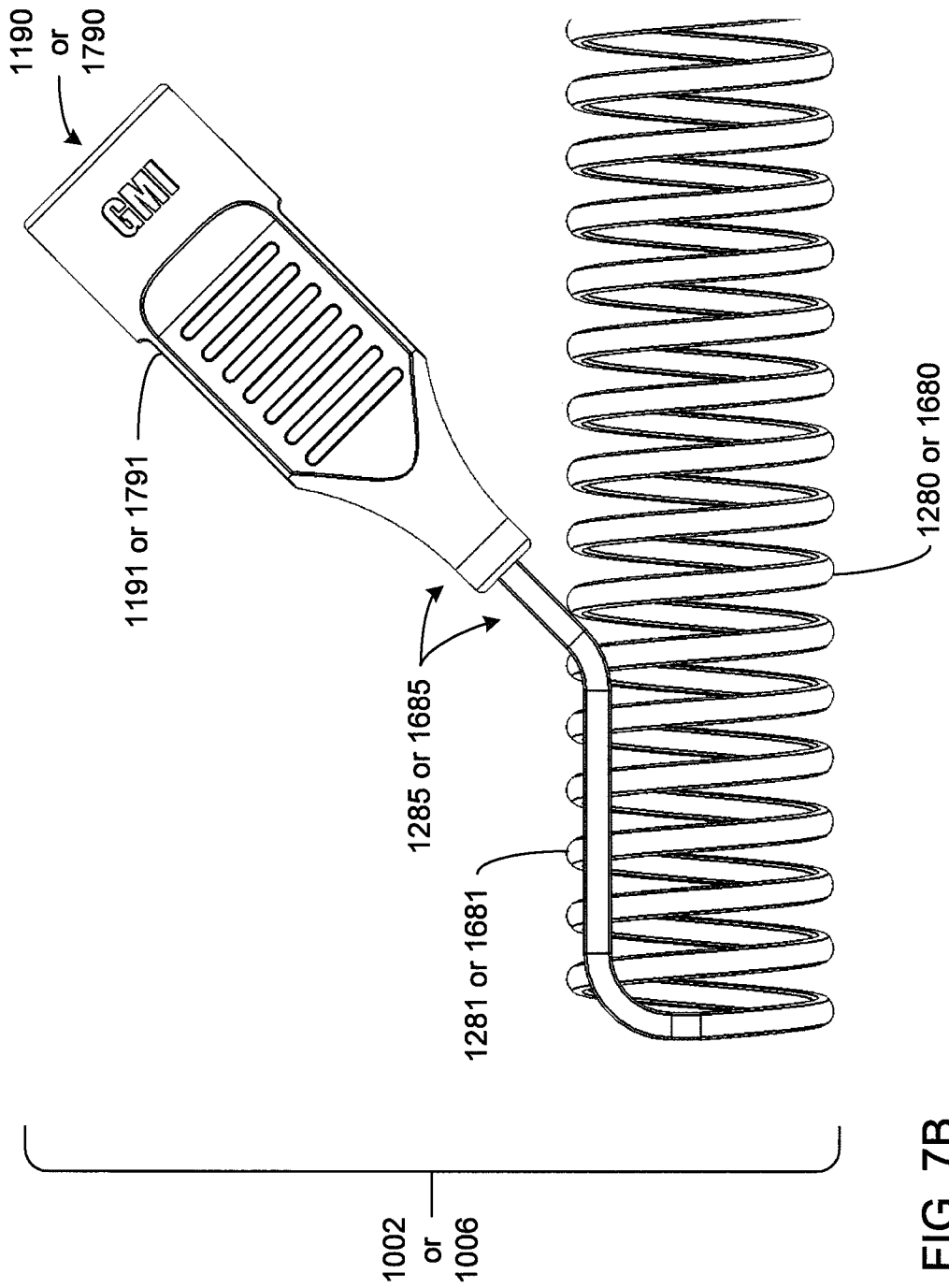
FIG. 7B is another partial elevational view of either the inspiratory hose assembly or the expiratory hose assembly of the embodiment of the heated respiratory hose assembly of FIG. 3B showing details of the manner in which the support helix is shaped and positioned within a hose fitting as part of forming a pigtail.
Figure 7C:
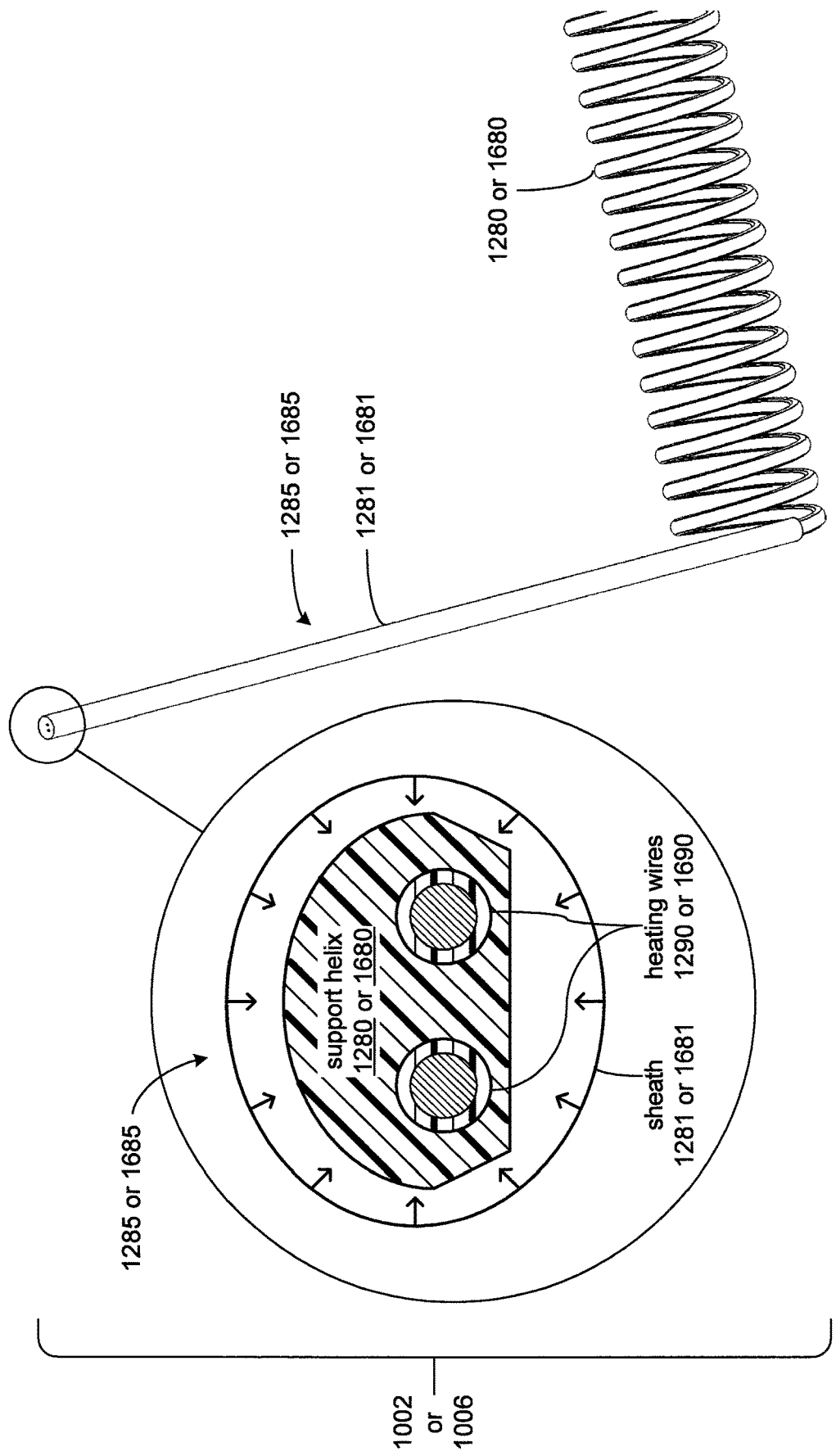
FIG. 7C is a combination of perspective and cross-sectional views of a portion of a pigtail of one of the hoses of either of the embodiments of heated respiratory hose assembly of any of FIG. 3B or 3C showing details of the formation of the pigtail from a portion of an unwound end of a support helix.

FIGS. 7A through 7C, taken together, depict various aspects of forming an electrical "pigtail" 1285 or 1685 from a portion of the support helix 1280 or 1680 for use in connecting the heating wires 1290 or 1690 to the medical device 990 to be provided with electrical power therefrom. In a manner similar to the embodiments depicted and discussed in reference to FIGS. 6A through 6G, FIGS. 7A through 7C present embodiments of the use of a portion of the support helix 1280 or 1680 as an electrical cable to advantageously avoid the creation of a electrical terminations where a transition is made between the heating wires 1290 or 1690, respectively, to non-heating wires. However, unlike the embodiments of FIGS. 6A through 6G in which the connector 1190 or 1790 is carried within the plug 1180 or 1780 installed within the fitting 1100 or 1700, respectively, in the embodiments of FIGS. 7A through 7C, the connector 1190 or 1790 is located in the environment external to the fitting 1100 or 1700 at the end of an electrical pigtail 1285 or 1685, respectively.

Each of FIGS. 7A through 7C depicts a subset of the components of either the inspiratory hose assembly 1002 or the expiratory hose assembly 1006 toward the end thereof that is to be connected to the medical device 990. More precisely, in each of FIGS. 7A through 7C, depictions of one of the undermold couplings 1800, and of the wall 1270 or 1670 of the hose 1200 or 1600 has been omitted to enable the helical path of the support helix 1280 or 1680, respectively, therein to be viewed more clearly. Additionally, in FIG. 7B, the depiction of either the inspiratory inlet fitting 1100 or the expiratory outlet fitting 1700 that is provided in FIG. 7A is also omitted to provide an uninterrupted view of the transition of the support helix 1280 or 1680 from its helical path for purposes of heating the interior of the hose 1200 or 1600 to a relatively straightened path for purposes of being used as an electrical cable to convey the heating wires 1290 or 1690 thereof to the connector 1190 or 1790.

Turning more specifically to FIGS. 7A and 7B, as depicted, where an end of a portion of the inspiratory hose 1200 is inserted into a portion of the inspiratory inlet fitting 1100, or where an end of a portion of the expiratory hose 1600 is inserted into a portion of the expiratory outlet fitting 1700, a portion of the support helix 1280 or 1680 is unwound from its helical path within the inspiratory hose 1200 or 1600 and is employed as an electrical cable to bring the heating wires 1290 or 1690 therein to the electrical connector 1190 or 1790 at an end of the electrical pigtail 1285 or 1685, respectively.

More specifically, a portion of the support helix 1280 or 1680 is pulled out of the end of the hose 1200 or 1600 (i.e., unwound therefrom) where that end is inserted into the fitting 1100 or 1700, respectively. The length of the unwound portion of the support helix 1280 or 1680 may be determined, at least in part, by the intended length of the electrical pigtail 1285 or 1685. The unwound portion of the support helix 1280 or 1680 may then be straightened to at least some degree for use as an electrical cable. This unwinding of the portion of the support helix 1280 may be performed prior to the threading of the depicted undermold coupling 1800 (again, not shown for purposes of visual clarity) onto the end of the hose 1200 or 1600 that is to be inserted into the fitting 1100 or 1700, respectively. As a result, the unwound portion of the support helix 1280 extends beyond the end of the 1200 or 1600 onto which the undermold coupling 1800 is threaded, thereby emerging from within the undermold coupling 1800 and extending further into the interior of the 1100 or 1700 than the end of the hose 1200 or 1600, respectively, onto which the undermold coupling 1800 is threaded. The unwound portion of the support helix 1280 or 1680 may then be fed through a channel and/or opening defined by a portion of the fitting 1100 or 1700 to be caused to extend into the environment external to the fitting 1100 or 1700 to serve as the core of the electrical pigtail 1285 or 1685.

Turning briefly to FIG. 7C, as depicted, the unwound portion of the support helix 1285 or 1685 may be covered in a sheath 1281 or 1681, at least where the unwound portion of the support helix 1285 or 1685 emerges from the fitting 1100 or 1700, respectively, and into the environment external thereto. Alternatively or additionally, the sheath 1281 or 1681 may cover at least part of the unwound portion of the support helix 1285 or 1685 within the fitting 1100 or 1700. In some embodiments, the sheath 1281 or 1681 may be a length of heatshrink tubing that is sleeved over the unwound portion of the support helix 1285 or 1685 (at least the length thereof that is within the environment external to the fitting 1200 or 1600), and then heated to cause the cross-section of the heatshrink tubing to shrink radially inward toward the exterior of the unwound portion of the support helix 1285 or 1685. Such an application of heat may also be used to aid in the straightening of the unwound portion of the support helix 1280 or 1680 and/or to somewhat change the shape thereof to conform to the interior surface of the heatshrink tubing as the heatshrink tubing is caused to tightly surround the unwound portion of the support helix 1285 or 1685, respectively (at least the length thereof that is within the environment external to the fitting 1200 or 1600).

Turning again more specifically to FIGS. 7A AND 7B, the end of the unwound portion of the support helix 1280 or 1680 that extends toward the electrical connector 1190 or 1790 may be partly stripped away to remove at least enough of the flexible plastics material of the support helix 1280 or 1680 (and maybe also to strip away a portion of the sheath 1281 or 1681) to expose enough of the heating wires 1290 or 1690 therein to enable forming an electrical connection with the contacts 1199 or 1799 of the electrical connector 1190 or 1790, respectively. Again, this may also be done using typical wire stripping techniques. Also again, in separating the relatively short portion of the support helix 1280 or 1680 from the hose 1200 or 1600, portions of the wall 1270 or 1670 (again, not shown for purposes of visual clarity) that extend between adjacent coils of the support helix 1280 or 1680 that are included in the unwound portion thereof may be trimmed away.

It has been discovered through testing that a transition from the heating wires 1290 or 1690 of the support helix 1280 or 1680, and to non-heating wires to form the electrical pigtail 1285 or 1685 is unnecessary, especially where the electrical pigtail 1285 or 1685 additionally includes the sheath 1281 or 1681 to provide additional insulation against the heat that may be generated within the electrical pigtail 1285 or 1685 by the heating wires 1290 or 1690, respectively, therein.

Although the invention has been described in a preferred form with a certain degree of particularity, it is understood that the present disclosure of the preferred form has been made only by way of example, and that numerous changes in the details of construction and the manner of manufacture may be resorted to without departing from the spirit and scope of the invention. It is intended to protect whatever features of patentable novelty exist in the invention disclosed.

The invention claimed is:

1. A method of forming a heated hose comprising:
   extruding a continuous web of plastics material of substantially uniform width from a first extruder of a hose making apparatus;
   helically winding the extruded web about a mandrel or at least one rotating rod of the hose making apparatus to form a wall of the heated hose about a central axis of the heated hose;
   feeding a first heating wire into a second extruder of the hose making apparatus;
   extruding a first continuous bead of plastics material around the first heating wire from the second extruder of the hose making apparatus such that the first extruded bead emerges from the second extruder with the first heating wire at a first location within a cross-section of the first extruded bead such that the first heating wire is fully surrounded by the plastics material of the first extruded bead;
   helically winding the first extruded bead onto and about an external surface of the wall of the hose formed from the helical winding of the extruded web to provide the wall a first support helix that incorporates the first heating wire; and exerting tension on the first heating wire as the first heating wire is fed into the second extruder, and as the first extruded bead is wound onto and about the external surface of the wall of the hose, to draw down the first heating wire toward the central axis of the hose such that the first heating wire migrates radially inward within the first extruded bead from the first location already within the cross-section of the first extruded bead to a second location that is still within the cross-section of the first extruded bead, and that is closer to the external surface of the wall of the hose and closer to the central axis than the first location within the cross-section of the first extruded bead.

2. The method of claim 1, wherein:
the cross-section of the extruded web include a pair of guide formations that extend radially outward from the wall of the hose after the extruded web is helically wound about the mandrel or the at least one rotating rod; and
the method further comprises using the pair of guide formations to guide the placement of the first extruded bead on the wall as the first extruded bead is helically wound about the wall.

3. The method of claim 1, further comprising helically winding the first extruded bead about the wall of the hose to provide a predetermined amount of space between adjacent coils of the first support helix to allow a fold, a curve or a convolution to be formed in stretches of the wall between the adjacent coils of the first support helix to enable the hose to bend or to be axially compressed along the central axis.

4. The method of claim 1, wherein the hose making apparatus comprises a tensioner incorporated into a spool of the first heating wire or interposed between the spool of the first heating wire and the second extruder to perform the exertion of tension on the first heating wire.

5. The method of claim 4, further comprising adjusting the tension exerted on the first heating wire as the hose is formed to vary the second location of the heating wire radially relative to the central axis within the first support helix.

6. The method of claim 1, wherein:
when the first extruded bead is helically wound onto and about the external surface of the wall of the hose, the first extruded bead is in a molten state that enables the first heating wire to migrate within the first extruded bead, and the wall of the hose is not in a molten state that would enable the first heating wire to migrate through the external surface of the wall of the hose such that the external surface of the wall is able to stop the radially inward migration of the first heating wire within the first extruded bead at the external surface of the wall; and
the method comprises:
exerting the tension on the first heating wire to cause radially inward migration of the first heating wire through the plastics material of the first extruded bead and onto the external surface of the wall; and
relying on the external surface of the wall being not in a molten state to stop the radially inward migration of the first heating wire.

7. The method of claim 1, further comprising:
feeding a second heating wire into the second extruder;
extruding the first extruded bead of plastics material around both the first heating wire and the second heating wire from the second extruder such that the first extruded bead comprises both the first heating wire at the first location within the cross-section of the first extruded bead and the second heating wire at a third location within the cross-section of the first extruded bead; and
exerting tension on the second heating wire as the second heating wire is fed into the second extruder to draw down the second heating wire toward the central axis of the hose such that the second heating wire migrates radially inward within the first extruded bead from the third location within the cross-section of the first extruded bead to a fourth location within the cross-section of the first extruded bead that is closer to the wall of the hose and closer to the central axis than the third location.

8. The method of claim 7, wherein:
the first heating wire comprises a first conductor sheathed by a first insulator; and
the second heating wire comprises a second conductor sheathed by a second insulator.

9. The method of claim 8, comprising connecting the first conductor directly to the second conductor at one end of the hose to form an electric loop by which the first heating wire and the second heating may be caused to cooperate to heat an interior of the hose by the provision of electric power to the first heating wire and the second heating wire at an opposite end of the hose.

10. The method of claim 1, further comprising:
feeding a second heating wire into a third extruder of the hose making apparatus;
extruding a second extruded bead of plastics material around the second heating wire from the third extruder such that the second extruded bead comprises the second heating wire at a third location within a cross-section of the second extruded bead;
helically winding the second extruded bead onto and about the external surface of the wall of the hose to provide the wall a second support helix that incorporates the second heating wire; and
exerting tension on the second heating wire as the second heating wire is fed into the third extruder to draw down the second heating wire toward the central axis of the hose such that the second heating wire migrates radially inward within the second extruded bead from the third location within the cross-section of the second extruded bead to a fourth location within the cross-section of the second extruded bead that is closer to the wall of the hose and closer to the central axis than the third location.

11. The method of claim 1, further comprising;
cutting the hose into multiple segments of the hose wherein each segment of the hose is cut to a length selected to be longer than needed to provide an extra length of the hose within each segment;
unwinding a portion of the first support helix from the extra length of the hose within each segment;
heating the unwound portion of each segment to straighten the unwound portion;
stripping part of an end of the unwound portion of each segment to expose the first heating wire; and
directly connecting the first heating wire of each segment to an electrical contact of an electrical connector to enable the first heating wire to be operated to heat an interior of the segment of the hose.

12. A method of forming a heated hose comprising:
extruding a continuous web of plastics material of substantially uniform width from a first extruder of a hose making apparatus;
helically winding the extruded web about a mandrel or at least one rotating rod of the hose making apparatus to form a wall of the heated hose about a central axis of the heated hose;
feeding a first heating wire and a second heating wire into a second extruder of the hose making apparatus;
extruding a continuous bead of plastics material around the first heating wire and the second heating wire from the second extruder of the hose making apparatus such that the extruded bead emerges from the second extruder with the first heating wire at a first location within a cross-section of the extruded bead and the second heating wire at a third location within a cross-section of the extruded bead such that the first heating wire and the second heating wire are both fully surrounded by the plastics material of the extruded bead;
helically winding the extruded bead onto and about an external surface of the wall of the hose formed from the helical winding of the extruded web to provide the wall a support helix that incorporates the first heating wire and the second heating wire;
exerting tension on the first heating wire as the first heating wire is fed into the second extruder, and as the extruded bead is wound onto and about the external surface of the wall of the hose, to draw down the first heating wire toward the central axis of the hose such that the first heating wire migrates radially inward within the extruded bead from the first location already within the cross-section of the extruded bead to a second location within that is still the cross-section of the extruded bead, and that is closer to the wall of the hose and closer to the central axis than the first location within the cross-section of the first extruded bead; and
exerting tension on the second heating wire as the second heating wire is fed into the second extruder and as the extruded bead is wound onto and about the external surface of the wall of the hose to draw down the second heating wire toward the central axis of the hose such that the second heating wire migrates radially inward within the extruded bead from the third location already within the cross-section of the extruded bead to a fourth location that is still within the cross-section of the extruded bead, and that is closer to the wall of the hose and closer to the central axis than the third location within the cross-section of the first extruded bead.

13. The method of claim 12, wherein:
the cross-section of the extruded web includes a pair of guide formations that extend radially outward from the wall of the hose after the extruded web is helically wound about the mandrel or the at least one rotating rod; and
the method further comprises using the pair of guide formations to guide the placement of the first extruded bead on the wall as the first extruded bead is helically wound about the wall.

14. The method of claim 12, further comprising helically winding the extruded bead about the wall of the hose to provide a predetermined amount of space between adjacent coils of the first support helix to allow a fold, a curve or a convolution to be formed in stretches of the wall between the adjacent coils of the support helix to enable the hose to bend or to be axially compressed along the central axis.

15. The method of claim 12, wherein the hose making apparatus comprises:
a first tensioner incorporated into a first spool of the first heating wire or interposed between the first spool and the second extruder to perform the exertion of tension on the first heating wire; and
a second tensioner incorporated into a second spool of the second heating wire or interposed between the second spool and the second extruder to perform the exertion of tension on the second heating wire.

16. The method of claim 15, further comprising adjusting the tension exerted on at least one of the first heating wire and the second heating wire as the hose is formed to vary at least one of the second location of the first heating wire radially relative to the central axis within the support helix and the fourth location of the second heating wire radially relative to the central axis within the support helix.

17. The method of claim 12, wherein:
when the extruded bead is helically wound onto and about the external surface of the wall of the hose, the extruded bead is in a molten state that enables the first heating wire and the second heating wire to migrate within the extruded bead, and the wall of the hose is not in a molten state that would enable the first heating wire and the second heating wire to migrate through the external surface of the wall of the hose such that the external surface of the wall is able to stop the radially inward migration of the first heating wire and the second heating wire within the extruded bead at the external surface of the wall; and
the method comprises:
exerting the tension on at least one of the first heating wire and the second heating wire to cause radially inward migration of the at least one of the first heating wire and the second heating wire fully through the plastics material of the extruded bead and onto the external surface of the wall; and
relying on the external surface of the wall being not in a molten state to stop the radially inward migration of the at least one of the first heating wire and the second heating wire.

18. The method of claim 12, wherein:
the first heating wire comprises a first conductor sheathed by a first insulator; and
the second heating wire comprises a second conductor sheathed by a second insulator.

19. The method of claim 18, comprising connecting the first conductor directly to the second conductor at one end of the hose to form an electric loop by which the first heating wire and the second heating may be caused to cooperate to heat an interior of the hose by the provision of electric power to the first heating wire and the second heating wire at an opposite end of the hose.

20. The method of claim 12, further comprising;
cutting the hose into multiple segments of the hose wherein each segment of the hose is cut to a length selected to be longer than needed to provide an extra length of the hose within each segment;
unwinding a portion of the support helix from the extra length of the hose within each segment;
heating the unwound portion of each segment to straighten the unwound portion;
stripping part of an end of the unwound portion of each segment to expose the first heating wire and the second heating wire; and
directly connecting the first heating wire of each segment to a first electrical contact of an electrical connector and directly connecting the second heating wire of each segment to a second electrical contact of the electrical connector to enable the first heating wire and the second heating wire to be operated to heat an interior of the segment of the hose.

\* \* \* \* \*